US012084512B2

(12) United States Patent
Thorn et al.

(10) Patent No.: US 12,084,512 B2
(45) Date of Patent: Sep. 10, 2024

(54) PROCOAGULANT ANTIBODIES

(71) Applicant: Novo Nordisk A/S, Bagsvaerd (DK)

(72) Inventors: Karina Thorn, Farum (DK); Bjarne Gram Hansen, Alleroed (DK); Laust Bruun Johnsen, Skodsborg (DK); Mikkel Nors Harndahl, Roskilde (DK); Zhiru Yang, Beijing (CN); Henrik Oestergaard, Oelstykke (DK); Per J. Greisen, Sammamish, WA (US); Morten Groenbech Rasch, Smoerum (DK); Jianhe Chen, Beijing (CN); Haisun Zhu, Norfolk, MA (US); Rong Zhou, Beijing (CN); Prafull S. Gandhi, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 509 days.

(21) Appl. No.: 16/481,108

(22) PCT Filed: Feb. 1, 2018

(86) PCT No.: PCT/EP2018/052550
§ 371 (c)(1),
(2) Date: Jul. 26, 2019

(87) PCT Pub. No.: WO2018/141863
PCT Pub. Date: Aug. 9, 2018

(65) Prior Publication Data
US 2021/0388114 A1    Dec. 16, 2021

(51) Int. Cl.
*C07K 16/36* (2006.01)
*A61K 39/00* (2006.01)
*A61P 7/04* (2006.01)

(52) U.S. Cl.
CPC ...... *C07K 16/36* (2013.01); *A61K 39/001154* (2018.08); *A61P 7/04* (2018.01); *A61K 2039/505* (2013.01); *C07K 2317/31* (2013.01); *C07K 2317/34* (2013.01); *C07K 2317/55* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen | A61P 31/12 435/69.6 |
| 6,624,295 B1 | 9/2003 | Adams et al. | |
| 7,279,161 B2 | 10/2007 | Scheiflinger et al. | |
| 8,062,635 B2 * | 11/2011 | Hattori | C07K 16/2866 424/136.1 |
| 9,334,331 B2 * | 5/2016 | Igawa | C07K 16/36 |
| 10,450,381 B2 | 10/2019 | Igawa et al. | |
| 10,759,870 B2 | 9/2020 | Teranishi et al. | |
| 11,220,554 B2 | 1/2022 | Thorn et al. | |
| 2002/0098188 A1 | 7/2002 | Kaibara et al. | |
| 2003/0069700 A1 | 4/2003 | Swairjo | |
| 2004/0110688 A1 | 6/2004 | Bajaj et al. | |
| 2005/0058640 A1 | 3/2005 | Kerschbaumer et al. | |
| 2005/0147618 A1 | 7/2005 | Rivera et al. | |
| 2005/0196397 A1 | 9/2005 | Scheiflinger et al. | |
| 2007/0041978 A1 | 2/2007 | Hattori et al. | |
| 2013/0266576 A1 | 10/2013 | Oestergaard et al. | |
| 2013/0330345 A1 | 12/2013 | Igawa et al. | |
| 2014/0050743 A1 | 2/2014 | Dittmer et al. | |
| 2014/0370018 A1 | 12/2014 | Igawa et al. | |
| 2016/0296602 A1 | 10/2016 | Johansen | |
| 2016/0297892 A1 | 10/2016 | Petersen et al. | |
| 2016/0362672 A1 | 12/2016 | Schellenberger et al. | |
| 2019/0185578 A1 | 6/2019 | Igawa et al. | |
| 2021/0107994 A1 | 4/2021 | Shima et al. | |
| 2021/0238306 A1 | 8/2021 | Thorn et al. | |

FOREIGN PATENT DOCUMENTS

| | | |
|---|---|---|
| CN | 103221429 A | 7/2013 |
| CN | 103396494 A | 11/2013 |
| CN | 103619883 A | 3/2014 |
| CN | 103298937 | 5/2016 |
| CN | 105705517 A | 6/2016 |
| EP | 1220923 A2 | 7/2002 |
| EP | 1660536 A2 | 5/2006 |
| EP | 2644698 A1 | 10/2013 |
| EP | 3121271 A1 | 1/2017 |
| JP | 2001523971 A | 11/2001 |
| JP | 2003509049 A | 3/2003 |

(Continued)

OTHER PUBLICATIONS

Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 2004).*
A.V. Filkenshtein et al., Protein Physics: lectures with colour anaglyphies and tasks: 4th edition, M., KDU, 2012, p. 23.

(Continued)

*Primary Examiner* — Michael Szperka
*Assistant Examiner* — Lia E Taylor
(74) *Attorney, Agent, or Firm* — Jianjie Hu

(57) ABSTRACT

The present invention relates to improved procoagulant antibodies including bispecific antibodies capable of binding to coagulation Factor IX (FIX) or the activated form thereof Factor IXa (FIXa) and optionally Factor X (FX) and the activated form thereof Factor Xa (FXa) and promoting FX activation by FIXa, antibodies binding their epitopes and methods and composition for treating subjects suffering from a coagulopathy such as haemophilia A.

5 Claims, 11 Drawing Sheets

Specification includes a Sequence Listing.

(56) References Cited

FOREIGN PATENT DOCUMENTS

| | | |
|---|---|---|
| JP | WO2006109592 A1 | 11/2008 |
| WO | 94/05692 A1 | 3/1994 |
| WO | 9850431 | 11/1998 |
| WO | 0007626 A1 | 2/2000 |
| WO | 2009/140598 A1 | 11/2009 |
| WO | 2010020423 A2 | 2/2010 |
| WO | 2010045321 A2 | 4/2010 |
| WO | 11080322 A1 | 7/2011 |
| WO | 2011088267 A1 | 7/2011 |
| WO | 2012/067176 A1 | 5/2012 |
| WO | 2013078089 A1 | 5/2013 |
| WO | 16166014 A1 | 10/2016 |
| WO | 2018098363 | 5/2018 |
| WO | 2018141863 A1 | 8/2018 |
| WO | 2018181870 A1 | 10/2018 |
| WO | 2018234575 A1 | 12/2018 |
| WO | 2019065795 | 4/2019 |
| WO | 2018021450 | 5/2019 |

OTHER PUBLICATIONS

Yarilin A.A., Introduction to immunology, M., Medicine, 1999, pp. 172-174.

Samelson-Jones et al., "Hyperactivity of factor IX Padua (R338L) depends on factor VIIIa cofactor activity," JCI Insight. Jun. 2019, vol. 5, No. 14, e128683, 14 pages.

F. Scheiflinger et al.,"Enhancement of the enzymatic activity of activated coagulation factor IX by anti-factor IX antibodies" Journal of Thrombosis and Haemostasis, 2008, vol. 6, No. 2, pp. 315-322.

Kerschbaumer et al.,"An Antibody Specific for Coagulation Factor IX Enhances the Activity of the Intrinsic Factor X-activating Complex ", Journal of Biological Chemistry, 2004, vol. 279, No. 39, pp. 40445-40450.

Kitazawa et al.,"A bispecific antibody to factors IXa and X restores factor VIII hemostatic activity in a hemophilia A model" Nature Medicine, 2012, vol. 18, No. 10, pp. 1570-1574.

Kitazawa et al., "Factor VIIIa-mimetic cofactor activity of a bispecific antibody to factors IX/IXa and X/Xa, emicizumab, depends on its ability to bridge the antigens", Thrombosis and Haemostasis, 2017, vol. 117, No. 7, pp. 1348-1357.

Kolkman et al.,"Insertion Loop 256-268 in Coagulation Factor IX Restricts Enzymatic Activity in the Absence but Not in the Presence of Factor VIII" Biochemistry, 2000, vol. 39, pp. 7398-7405.

Sampei et al.,"Identification and Multidimensional Optimization of an Asymmetric Bispecific IgG Antibody Mimicking the Function of Factor VIII Cofactor Activity" PLoS One, 2013, vol. 8, No. 2, p. e57479.

Uchida et al., "Plenary Paper Clinical Trials and Observations A first-in-human phase 1 study of ACE910, a novel factor VIII-mimetic bispecific antibody, in healthy subjects", 2015, Retrieved from the Internet: URL:http://www.bloodjournal.org/content/bloodjournal/127/13/1633.full.pdf?sso-checked=true, Retrieved on Apr. 19, 2018.

Zogg et al.,"Activation mechanisms of coagulation factor IX" Biol. Chem.,2009, vol. 390, pp. 391-400.

Lu et.al., "Acquired antagonistic activity of a bispecific diabody directed against two different epitopes on vascular endothelial growth factor receptor 2", Journal of Immunological Methods, Nov. 1999, vol. 230, pp. 159-171.

Zenzo et.al., "The Intracellular and Extracellular Domains of BP180 Antigen Comprise Novel Epitopes Targeted by Pemphigoid Gestationis Autoantibodies", Journal of Investigative Dermatology, Oct. 2006, vol. 127, pp. 864-873.

Comoglio et.al., "Drug development of MET inhibitors: targeting oncogene addiction and expedience", Nature Publishing Group, Jun. 2008, vol. 7, pp. 504-516.

Jakubke H.-D et al., "Amino acids, peptides, proteins: Translation from German.-M .: Mir," 1985.-456 p., illustrations; pp. 356-363.

Kreuz et al., "Inhibitors in patients with haemophilia A", Thrombosis Research, Apr. 18, 2014, vol. 134, pp. S22-S26.

"Anti-Factor IX Antibody, Mouse Monoclonal Clone HIX-1, Purified from Hybridma Cell Culture," Sigma-Aldrich, http://www.sigmaaldrich.com/catalog/product/sigma/f2645?lang=en&region=DK, accessed Jan. 19, 2018.

"Anti-Human Factor IX," Haematologic Technologies, Inc., https://www.haemtech.com/products/antibodies/anti-human-factor-ix, accessed Jan. 19, 2018.

Affinity Biologicals Antibodies to Factor IX http://www.affinitybiologicals.com/factor-ix-polyclonal-antibody/, accessed May 21, 2019.

Anonymous: Assessment report Hemlibra (International nonproprietary name: emicizumab Procedure No. Emea/H/C/004406/0000), European Medicines Agency, Jan. 25, 2018, pp. 1-126, XP002780260, Retrieved from the Internet: URL:http://www.ema.europa.eu/docs/en_GB/document_library/EPAR_-_public_assessment_report/human/004406/WC500244745.pdf [retrieved on Apr. 19, 2018].

Bajaj et al., "A monoclonal antibody to factor IX that inhibits the factor VIII: CA potentiation of factor X activation," Journal of Biological Chemistry, 1985, vol. 260, No. 1, pp. 11574-11580.

CaptureSelect™ Biotin Anti-FIX Conjugate https://www.thermofisher.com/order/catalog/product/7103002100, accessed May 21, 2019.

Ganesan R. et al., "Structural and mechanistic insight into how antibodies inhibit serine proteases", Biochem. J., 2010, vol. 430, pp. 179-189.

Kolkman et al., "Insertion Loop 256-268 in Coagulation Factor IX Restricts Enzymatic Activity in the Absence but Not in the Presence of Factor VIII," Biochemistry, 2000, vol. 39, No. 25, pp. 7398-7405.

Lin S, et al., "Identification of functionally important residues in the protease domain of Factor IX that are critical for binding factor XIa, TFPI and antibodies", Blood, 2002, vol. 100, Issue 11, pp. 263A-263A.

Norris et al., "Synthetic, switchable enzymes," J Mol Microbiol Biotechnol, 2017, vol. 27, No. 2, pp. 117-127.

Other Anti-FIX Antibody Products http://www.biocompare.com/pfu/110447/soids/35803/Antibodies/FIX, accessed May 21, 2019.

Safari S. et al., "Use of a Bacterially Expressed Human Factor IX Light Chain to Develop Polyclonal Antibody Anti nFIX", Appl Biochem Biotechnol, 2009, vol. 159, pp. 404-414.

Sampei et al., "Identification and Multidimensional Optimization of an Asymmetric Bispecific IgG Antibody Mimicking the Function of Factor VIII Cofactor Activity," PLoS One, 2013, vol. 8, No. 2, e57479.

Scheiflinger et al., "Enhancement of the enzymatic activity of activated coagulation factor IX by anti-factor IX antibodies," J Thromb Haemost, 2008, vol. 6, pp. 315-322.

Uchida et al., "Plenary paper Clinical Trials and Observations A first-in-human phase 1 study of ACE910, a novel factor VIII-mimetic bispecific antibody, in health subjects," Dec. 1, 2015, vol. 127, pp. 1663-1641, XP055468638, Retrieved from the Internet: URL:http://www.bloodjournal.org/content/bloodjournal/127/13/1633.full.pdf?sso-checked=true (retrieved on Apr. 19, 2018).

Zögg T, "Activation mechanisms of coagulation factor IX," Biol Chem, 2009, vol. 390, Nos. 5-6, pp. 391-400.

\* cited by examiner

Sequence alignment showing CDRs in boxes

Sequence alignment of anti-FIX VH domain sequences of 1-1307 lineage:

FIGURE 1F

Sequence alignment of anti-FIX VL domain sequences of 1-1307 lineage:

FIGURE 1G

Sequence alignment of anti-FIX VH domain sequences of other lineage:

[Sequence alignment figure - illegible at this resolution]

Sequence alignment of anti-FIX VL domain sequences of other lineage:

[Sequence alignment figure - illegible at this resolution]

Exp. A

Exp. B

Exp. C

Exp. D

Exp. E

PROCOAGULANT ANTIBODIES

INCORPORATION BY REFERENCE OF THE SEQUENCE LISTING

The Sequence Listing, entitled "160163WO02_ST25", is 198 kilobytes and was created on 30 Jan. 2018 and is incorporated herein by reference.

BACKGROUND

In patients with a coagulopathy, such as in human beings with haemophilia A and B, various steps of the coagulation cascade are rendered dysfunctional due to, for example, the absence or insufficient presence of a functional coagulation factor. Such dysfunction of one part of the coagulation cascade results in insufficient blood coagulation and potentially life-threatening bleeding, or damage to internal organs, such as the joints.

Coagulation Factor VIII (FVIII) deficiency, commonly referred to as haemophilia A, is a congenital bleeding disorder affecting approximately 420,000 people worldwide, of which around 105,000 are currently diagnosed.

Patients with haemophilia A may receive coagulation factor replacement therapy such as exogenous FVIII. Conventional treatment consists of replacement therapy, provided as prophylaxis or on demand treatment of bleeding episodes. Until recently prophylactic treatment for a patient with severe haemophilia A was up to three intravenous injections/week with either plasma derived FVIII or recombinant FVIII or long-acting variants thereof.

However, such patients are at risk of developing neutralizing antibodies, so-called inhibitors, to such exogenous factors, rendering formerly efficient therapy ineffective. Haemophilia A patients with inhibitors is a non-limiting example of a coagulopathy that is partly congenital and partly acquired. Patients that have developed inhibitors to FVIII cannot be treated with conventional replacement therapy. Recently, a new drug, Hemlibra, has been approved for subcutaneous prophylactic treatment of Haemophilia A with inhibitors. Exogenous coagulation factors may only be administered intravenously, which is of considerable inconvenience and discomfort to patients. For example, infants and toddlers may have to have intravenous catheters surgically inserted into a chest vein, in order for venous access to be guaranteed. This leaves them at great risk of developing bacterial infections. Thus, even with the entry of Hemlibra there is a need for alternative subcutaneous treatment in haemophilia with inhibitors.

In a bleeding individual, coagulation is initiated by formation of the Tissue Factor/Factor VIIa (TF/FVIIa) complex when extravascular TF is exposed to activated FVII (FVIIa) in the blood. TF/FVIIa complex formation leads to the activation of coagulation Factor X (FX) to activated coagulation Factor Xa (FXa) which, together with activated coagulation Factor V (FVa), generates a limited amount of thrombin, which in turn activates blood platelets. Activated platelets support the assembly of the tenase complex composed of activated Factor VIII (FVIIIa) and activated coagulation Factor IX (FIXa). The tenase complex is a very efficient catalyst of FX activation and FXa generated in this second step serves as the active protease in the FVa/FXa pro-thrombinase complex which is responsible for the final thrombin burst. Thrombin cleaves fibrinogen to generate fibrin monomers, which polymerise to form a fibrin network which seals the leaking vessel and stops the bleeding. The rapid and extensive thrombin burst is a prerequisite for the formation of a solid and stable fibrin clot.

An inadequate FXa formation and decreased thrombin generation caused by reduced or absent FVIII activity is the reason underlying the bleeding diathesis in haemophilia A patients.

As mentioned, proteolytic conversion of FX into its enzymatically active form FXa can be achieved by the intrinsic FX-activating complex comprising FIXa and its cofactor FVIIIa. Cofactor binding increases the enzymatic activity of FIXa by about five orders of magnitude and is believed to result through multiple mechanisms as outlined by Scheiflinger et al. (2008) *J Thromb Haemost,* 6:315-322. Notably, FVIIIa has been found to stabilize a conformation of FIXa that has increased proteolytic activity towards FX (Kolkman J A, Mertens K (2000) *Biochemistry,* 39:7398-7405, Zögg T, Brandstetter H (2009) *Biol Chem,* 390:391-400). Based on this observation and realizing that antibodies are versatile binding proteins capable of mimicking a variety of protein-protein interactions, Scheiflinger et al. performed a screen for agonistic anti-FIXa antibodies characterized by an ability to enhance FX activation by FIXa in the presence of a phospholipid surface and calcium, but in the absence of the natural cofactor FVIIIa. From a screen of 5280 hybridoma supernatants, 88 were found to produce antibodies exhibiting various degrees of FIXa agonistic activity, cf. EP1220923 B1 and EP1660536 B1. With respect to the kinetics of FX activation and ability to stimulate thrombin generation in FVIII-deficient human plasma, EP1660536 B1 consistently points to 224F3 as the most efficient antibody (cf. e.g. sections 0060 and 0062). ACE910 or Emicizumab (trade name Hemlibra®) is a humanized, bispecific anti-FIX(a)/anti-FX(a) monoclonal antibody developed by Chugai Pharmaceutical for the treatment of haemophilia A. ACE910 is designed to mimic FVIII cofactor function (see Sampei et al.: (2013) *PLoS One,* 8, e57479 and WO2012067176).

There are still many unmet medical needs in the haemophilia community, in particular, and in subjects with coagulopathies, in general and the present invention relates to improved compounds capable of substituting for FVIII and thus being useful for the treatment of a coagulopathy such as haemophilia A.

SUMMARY

The present invention relates to compounds, which serve as a substitute for coagulation Factor VIII (FVIII) in patients suffering from a coagulopathy and in particular patients lacking functional FVIII, such as haemophilia A patients including haemophilia A patients with inhibitors.

Hence, one aspect of the present invention relates to compounds capable of enhancing the generation of FXa and thus partially or completely restore coagulation in patients lacking FVIII.

In one aspect, the compound is an antibody. In one such aspect, the compound is a multispecific antibody such as a bispecific antibody.

In one particular aspect, the invention relates to procoagulant antibodies which serve as a substitute for FVIII in patients lacking FVIII, such as haemophilia A patients.

In one such aspect, the antibody binds to and increases the enzymatic activity of FIXa towards FX, optionally also binding FX.

In one aspect, the invention relates to a procoagulant antibody that binds FX, including bispecific procoagulant antibodies which increase the enzymatic activity of FIXa towards FX and binding FX.

In one aspect, the invention relates to a procoagulant bispecific antibody that is capable of binding to coagulation FIX/FIXa and FX/FXa.

In one aspect, the antibody is human or humanised.

A further aspect of the invention relates to the individual antibodies or antigen-binding fragment thereof that are part of a procoagulant antibody, such as a particular anti-FIX or anti-FIXa antibody or antigen-binding fragment thereof. A further aspect of the invention relates to the individual antibodies or antigen-binding fragment thereof that are part of a procoagulant antibody, such as a particular anti-FX or anti-FXa antibody or antigen-binding fragment thereof.

A further aspect of the invention relates to the manufacture of the antibodies—and intermediates thereof—as disclosed herein.

A further aspect of the invention relates to an antibody that competes with a procoagulant antibody or antigen-binding fragment hereof, as disclosed herein, for binding to FIX/FIXa.

A further aspect of the invention relates to a procoagulant antibody that competes with an antibody or antigen-binding fragment hereof, as disclosed herein, for binding to FX/FXa.

A still further aspect of the invention relates to a pharmaceutical composition comprising a procoagulant antibody as disclosed herein formulated for the delivery of said antibody for the prevention and/or treatment of a coagulopathy.

A further aspect of the invention is directed to the procoagulant antibodies disclosed herein for prevention and/or treatment of a coagulopathy, a disease accompanying coagulopathy, or a disease caused by coagulopathy.

The invention may also solve further problems that will be apparent from the disclosure of the exemplary embodiments.

BRIEF DESCRIPTION OF THE FIGURES

Figure 1A:
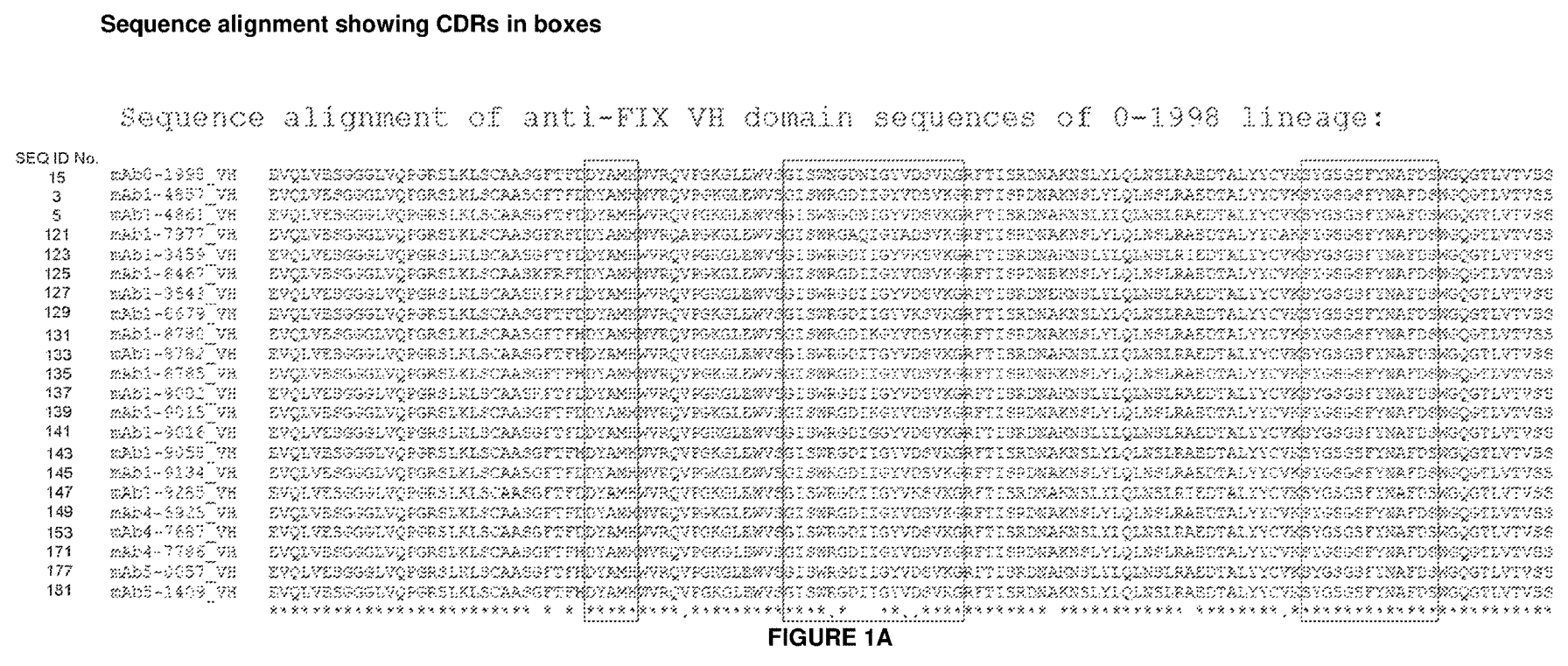
Figure 1B:
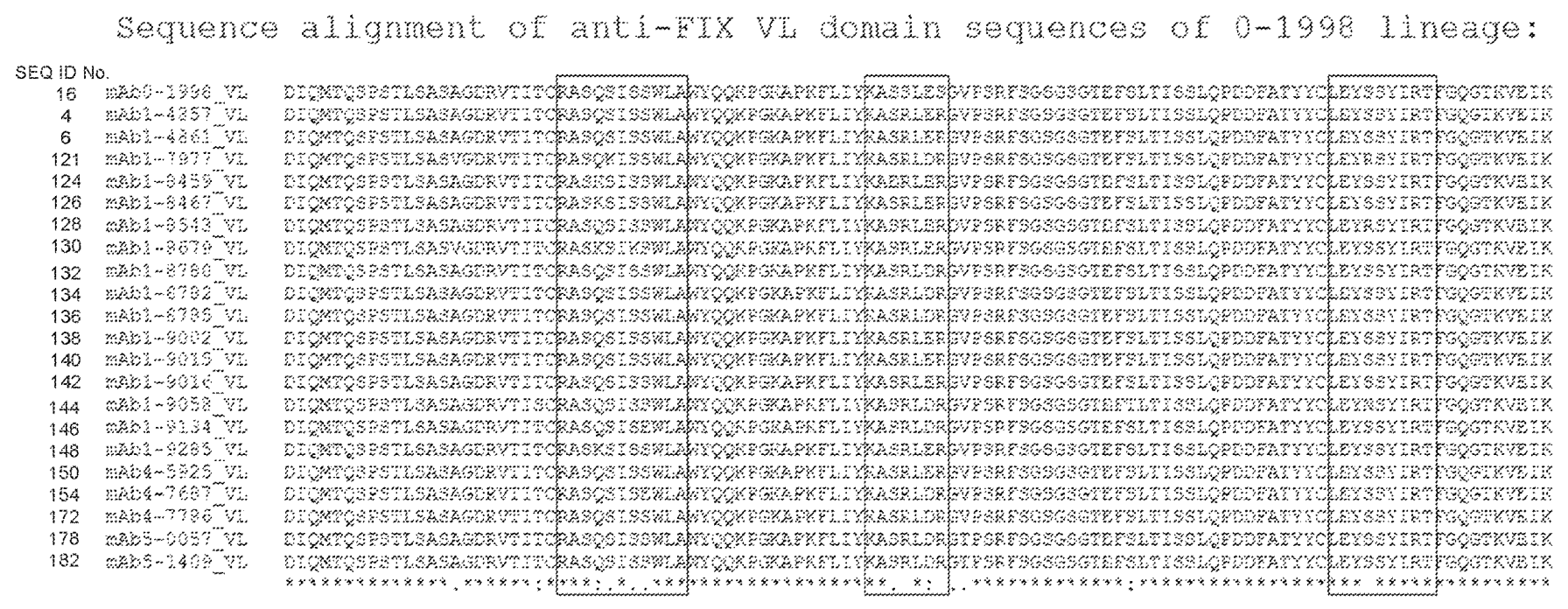
Figure 1C:
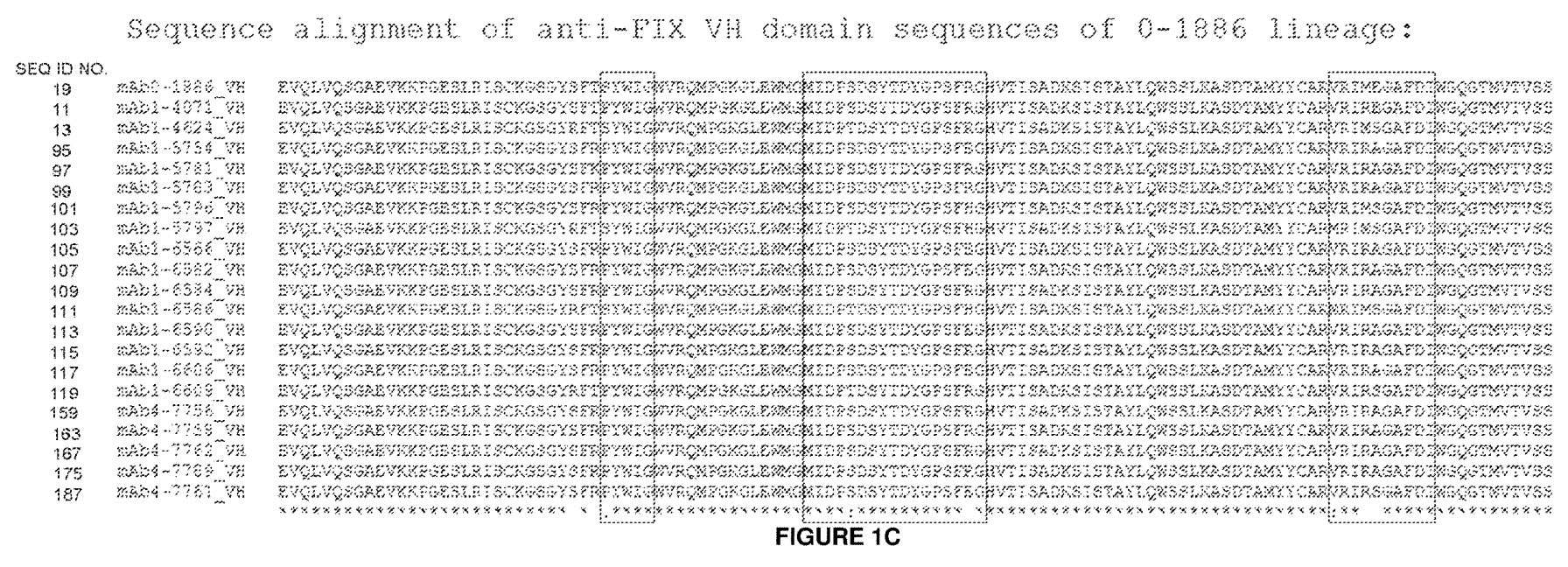
Figure 1D:
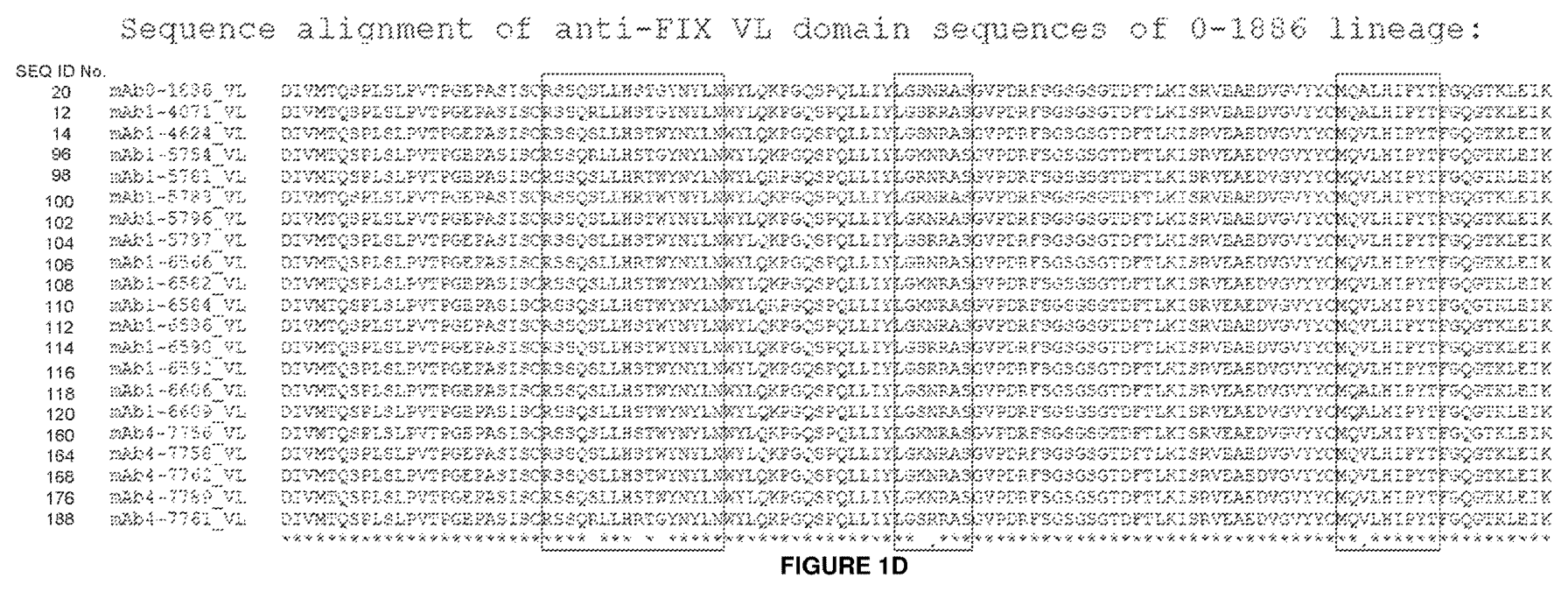
Figure 1I:
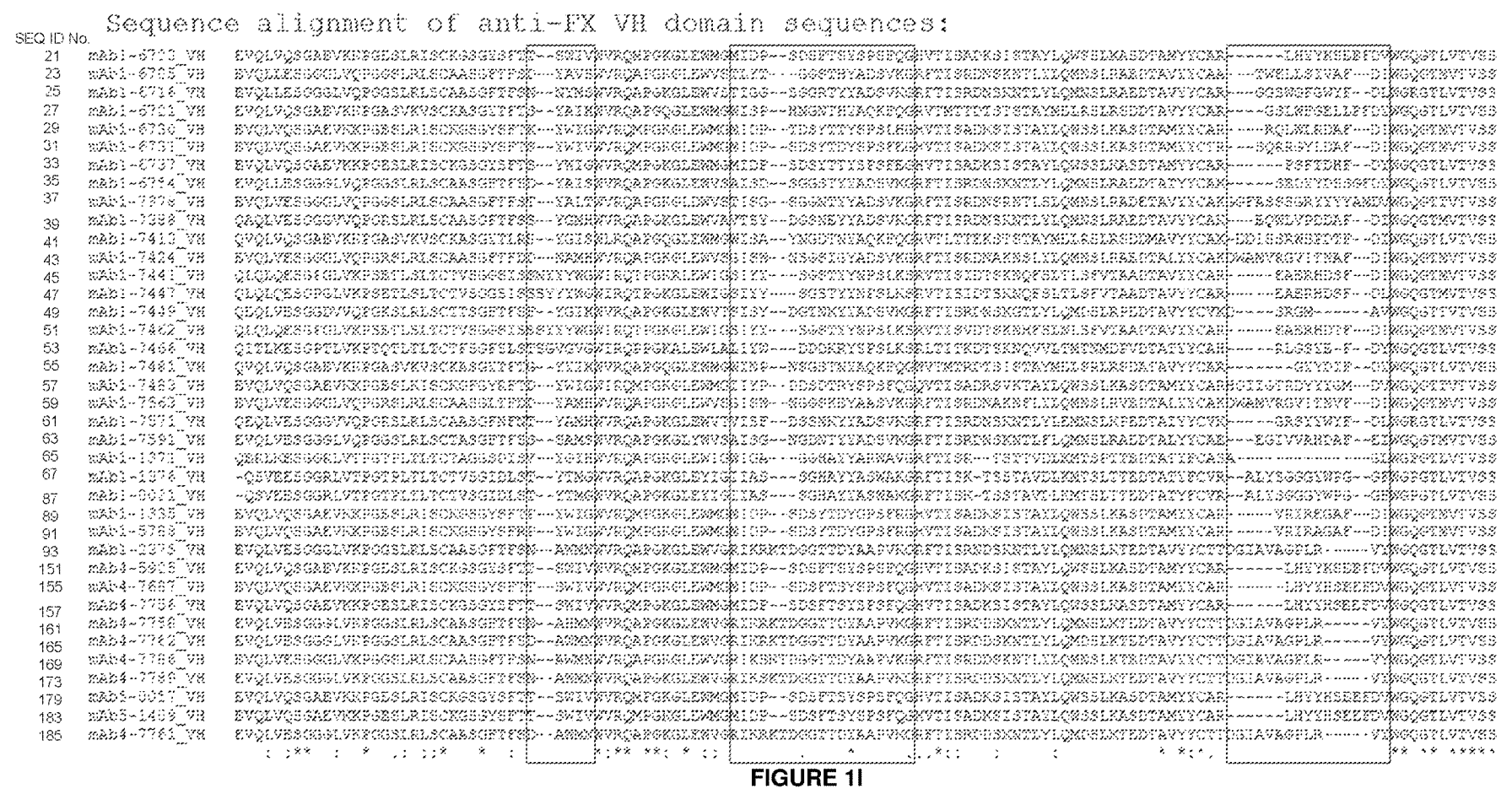
Figure 1J:
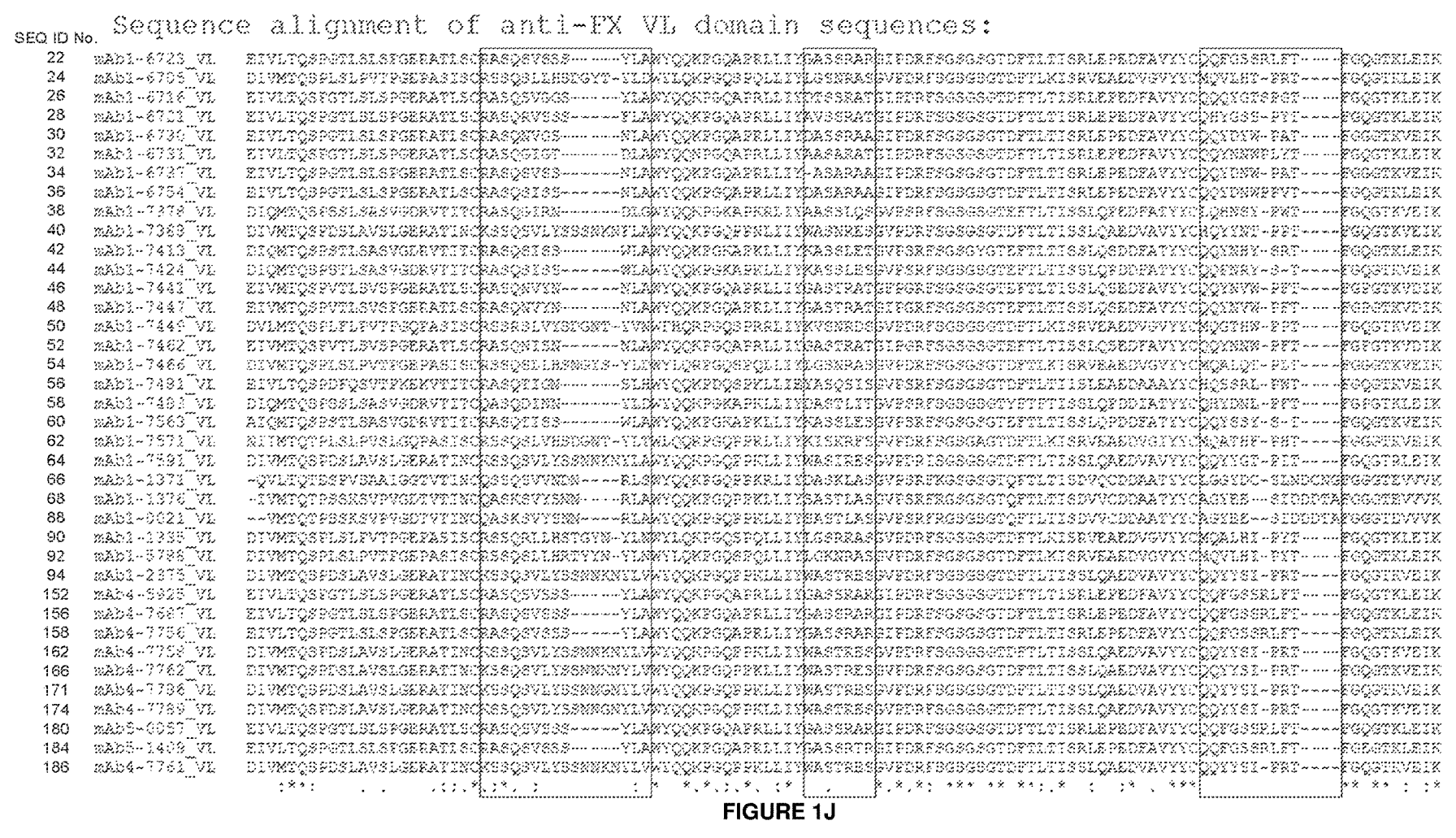

FIG. 1 shows aligned sequences of SEQ ID NOs:3-188 wherein Complementarity Determining Region 1, 2 and 3 (CDR1, CDR2 and CDR3) of the heavy chain and light chain variable domains have been highlighted consecutively in boxes. FIG. 1A shows sequence alignment of anti-FIX VH domain sequenes of 0-1998 lineage. FIG. 1B shows sequence alignment of anti-FIX VL domain sequenes of 0-1998 lineage. FIG. 1C shows sequence alignment of anti-FIX VH domain sequenes of 0-1886 lineage. FIG. 1D shows sequence alignment of anti-FIX VL domain sequenes of 0-1886 lineage. FIG. 1E shows sequence alignment of anti-FIX VH domain sequenes of 1-1307 lineage. FIG. 1F shows sequence alignment of anti-FIX VL domain sequenes of 1-1307 lineage. FIG. 1G shows sequence alignment of anti-FIX VH domain sequenes of other lineage. FIG. 1H shows sequence alignment of anti-FIX VL domain sequenes of other lineage. FIG. 1I shows sequence alignment of anti-FX VH domain sequenes. FIG. 1J shows sequence alignment of anti-FX VL domain sequenes.

BRIEF DESCRIPTION OF THE SEQUENCES

Figure 2:
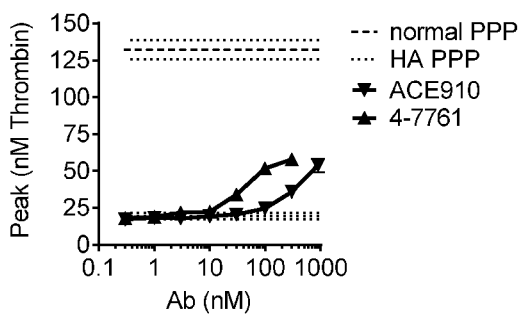
FIG. 2 shows Thrombin generation test (TGT) data from the bispecific antibodies mAb4-7761, mAb4-7762, mAb4-7789, mAb5-0057, mAb5-1409 and ACE910 in human tissue factor activated haemophilia A platelet-poor plasma (HA-PPP). The experiment was performed as described in Example 17. Dotted and stippled lines indicate the peak thrombin level (nM) observed in the absence of anti-FVIII antibody in HA-PPP and normal PPP, respectively, and with their standard deviation indicated by dotted lines. The profiles of mAb4-7761, mAb4-7762, mAb4-7789, mAb5-0057, and mAb5-1409 are indicated by up-pointing triangles, whereas that of ACE910 is indicated by down-pointing triangles. Exp. A-E refer to independent experiments; within each of these experiments the peak thrombin level at each antibody concentration represents the mean±standard deviation of at least three independent runs.
Figure 2:
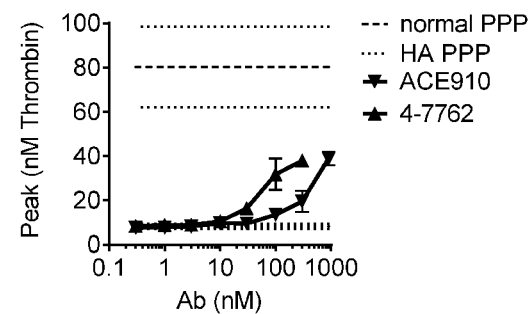
Figure 2:
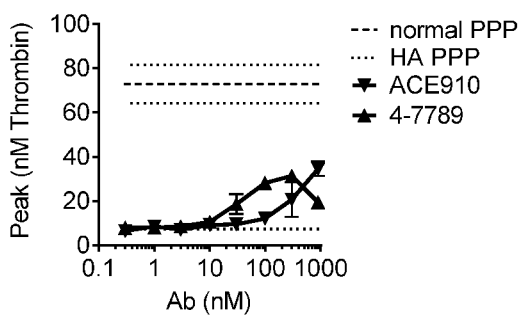
Figure 2:
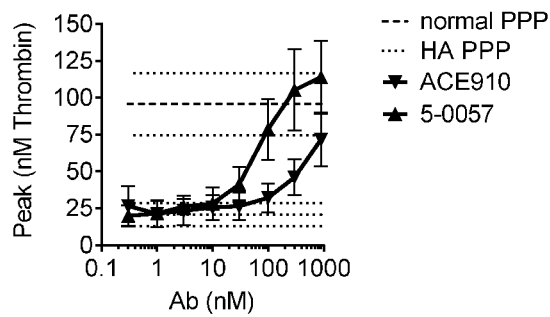
Figure 2:
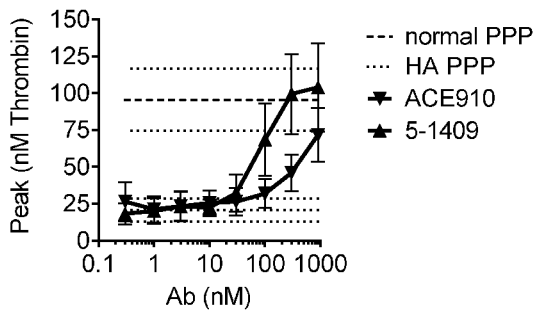

SEQ ID NO:1 is the amino acid sequence of human coagulation Factor IX.

SEQ ID NO:2 is the amino acid sequence of human coagulation Factor X.

SEQ ID NO:3-188 are the sequences of the heavy chain variable domains ($V_H$) and light chain variable domains ($V_L$) of anti-FIX and anti-FX monoclonal antibodies (mAbs) described herein. IDs for corresponding one-armed (OA) antibodies as well as certain bispecific antibodies are also shown in the table. CDR1-3 sequences are highlighted in boxes in FIG. 1.

Overview of antibody abbreviations, target and SEQ ID NOs for corresponding $V_H$ and $V_L$ sequences:

| OA or bispecific antibody ID | mAb ID | Target | SEQ ID NO ($V_H$) | SEQ ID NO ($V_L$) |
|---|---|---|---|---|
| | 1-4857 | FIX | 3 | 4 |
| | 1-4861 | FIX | 5 | 6 |
| | 1-4707 | FIX | 7 | 8 |
| | 1-4763 | FIX | 9 | 10 |
| | 1-4071 | FIX | 11 | 12 |
| | 1-4624 | FIX | 13 | 14 |
| 4-0004 | 0-1998 | FIX | 15 | 16 |
| 3-3279 | 1-1307 | FIX | 17 | 18 |
| 4-0673 | 0-1886 | FIX | 19 | 20 |
| 4-6934 | 1-6723 | FX | 21 | 22 |
| | 1-6705 | FX | 23 | 24 |
| | 1-6716 | FX | 25 | 26 |
| | 1-6721 | FX | 27 | 28 |
| | 1-6730 | FX | 29 | 30 |
| | 1-6731 | FX | 31 | 32 |
| | 1-6737 | FX | 33 | 34 |
| | 1-6754 | FX | 35 | 36 |
| | 1-7378 | FX | 37 | 38 |
| | 1-7388 | FX | 39 | 40 |
| | 1-7413 | FX | 41 | 42 |

-continued

| OA or bispecific antibody ID | mAb ID | Target | SEQ ID NO (V_H) | SEQ ID NO (V_L) |
|---|---|---|---|---|
|  | 1-7424 | FX | 43 | 44 |
|  | 1-7441 | FX | 45 | 46 |
|  | 1-7447 | FX | 47 | 48 |
|  | 1-7449 | FX | 49 | 50 |
|  | 1-7462 | FX | 51 | 52 |
|  | 1-7466 | FX | 53 | 54 |
|  | 1-7481 | FX | 55 | 56 |
|  | 1-7483 | FX | 57 | 58 |
|  | 1-7563 | FX | 59 | 60 |
|  | 1-7571 | FX | 61 | 62 |
|  | 1-7591 | FX | 63 | 64 |
|  | 1-1371 | FX | 65 | 66 |
|  | 1-1376 | FX | 67 | 68 |
|  | 0-2000 | FIX | 69 | 70 |
|  | 0-2001 | FIX | 71 | 72 |
|  | 0-2003 | FIX | 73 | 74 |
|  | 1-0072 | FIX | 75 | 76 |
|  | 1-0073 | FIX | 77 | 78 |
|  | 1-0970 | FIX | 79 | 80 |
|  | 1-0982 | FIX | 81 | 82 |
|  | 1-0985 | FIX | 83 | 84 |
|  | 0-1448 | FIX | 85 | 86 |
|  | 1-0021 | FX | 87 | 88 |
|  | 1-1335 | FIX | 89 | 90 |
|  | 1-5788 | FIX | 91 | 92 |
|  | 1-2375 | FX | 93 | 94 |
| 4-3461 | 1-5754 | FIX | 95 | 96 |
| 4-3486 | 1-5781 | FIX | 97 | 98 |
| 4-3490 | 1-5783 | FIX | 99 | 100 |
| 4-3503 | 1-5796 | FIX | 101 | 102 |
| 4-3505 | 1-5797 | FIX | 103 | 104 |
| 4-5337 | 1-6566 | FIX | 105 | 106 |
| 4-5347 | 1-6582 | FIX | 107 | 108 |
| 4-5355 | 1-6584 | FIX | 109 | 110 |
| 4-5342 | 1-6586 | FIX | 111 | 112 |
| 4-5357 | 1-6590 | FIX | 113 | 114 |
| 4-5344 | 1-6592 | FIX | 115 | 116 |
| 4-5368 | 1-6606 | FIX | 117 | 118 |
| 4-5375 | 1-6609 | FIX | 119 | 120 |
| 4-9578 | 1-7977 | FIX | 121 | 122 |
| 5-0900 | 1-8459 | FIX | 123 | 124 |
| 5-0908 | 1-8467 | FIX | 125 | 126 |
| 5-0514 | 1-8543 | FIX | 127 | 128 |
| 5-0658 | 1-8679 | FIX | 129 | 130 |
| 5-0144 | 1-8780 | FIX | 131 | 132 |
| 5-0152 | 1-8782 | FIX | 133 | 134 |
| 5-0161 | 1-8785 | FIX | 135 | 136 |
| 5-1257 | 1-9002 | FIX | 137 | 138 |
| 5-1263 | 1-9015 | FIX | 139 | 140 |
| 5-1270 | 1-9016 | FIX | 141 | 142 |
| 5-1528 | 1-9058 | FIX | 143 | 144 |
| 5-1695 | 1-9134 | FIX | 145 | 146 |
| 5-2035 | 1-9285 | FIX | 147 | 148 |
| 4-5925 | 1-4857/1-6723 | FIX/FX | 149, 151 | 150, 152 |
| 4-7687 | 1-6037/1-6723 | FIX/FX | 153, 155 | 154, 156 |
| 4-7756 | 1-6584/1-6723 | FIX/FX | 159, 157 | 160, 158 |
| 4-7758 | 1-6584/1-6097 | FIX/FX | 163, 161 | 164, 162 |
| 4-7762 | 1-6584/1-6738 | FIX/FX | 167, 165 | 168, 166 |
| 4-7786 | 1-6081/1-6463 | FIX/FX | 171, 169 | 172, 170 |
| 4-7789 | 1-6584/1-6463 | FIX/FX | 175, 173 | 176, 174 |
| 5-0057 | 1-8768/1-6723 | FIX/FX | 177, 179 | 178, 180 |
| 5-1409 | 1-8768/1-7503 | FIX/FX | 181, 183 | 182, 184 |
| 4-7761 | 1-5743/1-6738 | FIX/FX | 187, 185 | 188, 186 |

The first column ("OA or bispecific antibody ID") contains abbreviations for monovalent one-armed (OA) antibodies and/or bispecific antibodies. The second column ("mAb ID") represents abbreviations for corresponding component antibodies (for bispecific antibodies, the first mentioned antibody in the second column is an anti-FIX/FIXa antibody and the second is an anti-FX/FXa antibody). Fourth ("SEQ ID NO (V_H)") and fifths ("SEQ ID NO (V_L)") columns represent SEQ ID NOs for V_H and V_L sequences, respectively, with the first SEQ ID NO in each column representing the anti-FIX/FIXa antibody and the second the anti-FX/FXa antibody.

DESCRIPTION

In subjects with a coagulopathy, such as in human beings with haemophilia A, the coagulation cascade is rendered dysfunctional due to the absence or insufficient presence of functional FVIII. Such dysfunction of one part of the coagulation cascade results in insufficient blood coagulation and potentially life-threatening bleeding, or damage to internal organs, such as the joints. The present invention relates to compounds, which serve as a substitute for coagulation Factor VIII (FVIII) in patients suffering from a coagulopathy and in particular patients lacking functional FVIII, such as haemophilia A patients including haemophilia A patients with inhibitors. In one aspect, such compound is an antibody.

In particular the inventors of the present invention have surprisingly identified antibodies which mimic FVIII cofactor activity with high potency and efficacy.

In one particular aspect, the invention relates to procoagulant antibodies which serve as a substitute for FVIII in patients lacking functional FVIII, such as haemophilia A patients.

In one such aspect, the procoagulant antibodies bind to and increase the enzymatic activity of coagulation Factor IXa (FIXa) towards coagulation Factor X (FX), optionally also binding FX. In one such aspect the antibodies of the invention are bispecific antibodies capable of binding to FIX/FIXa and FX.

Coagulation Factor IX

FIX is a vitamin K-dependent coagulation factor with structural similarities to Factor VII, prothrombin, Factor X, and Protein C. The circulating zymogen form consists of 415 amino acids divided into four distinct domains comprising an N-terminal γ-carboxyglutamic acid-rich (Gla) domain, two EGF domains and a C-terminal trypsin-like serine protease domain. FIX circulates in plasma as a single-chain zymogen (SEQ ID NO:1). Activation of FIX occurs by limited proteolysis at Arg145 and Arg180 to release the activation peptide (residues 146 to 180 of SEQ ID NO:1). Thus, activated FIX (FIXa) is composed of residues 1-145 of SEQ ID NO:1 (light chain) and residues 181-415 of SEQ ID NO:1 (heavy chain).

Circulating FIX molecules thus comprise the FIX zymogen and the activated form of FIX which are herein generally referred to as FIX and FIXa with reference to SEQ ID NO:1.

Activated Factor IX is referred to as Factor IXa or FIXa. The term "FIX (SEQ ID NO:1) and/or the activated form thereof (FIXa)" may also be referred to as "FIX/FIXa" or "FIX(a)".

FIXa is a trypsin-like serine protease that serves a key role in haemostasis by generating, as part of the tenase complex, most of the Factor Xa required to support proper thrombin formation during coagulation.

FIX is herein represented by SEQ ID NO:1 corresponding to the Ala148 allelic form of human FIX (Anson et al. EMBO J. 1984 3:1053-1060; McGraw et al., Proc Natl Acad Sci USA. 1985 82:2847-2851; Graham et al. Am. J. Hum. Genet. 1988 42:573-580). In the present invention FIX is intended to cover all natural variants of FIX, such as the T148 variant (Uniprot ID P00740).

Coagulation Factor X

FX is a vitamin K-dependent coagulation factor with structural similarities to Factor VII, prothrombin, FIX, and protein C. Human FX zymogen comprises four distinct domains comprising an N-terminal gamma-carboxyglutamic acid rich (Gla) domain, two EGF domains, and a C-terminal trypsin-like serine protease domain. FX circulates in plasma as a two-chain zymogen including residues 1-139 of SEQ ID NO:2 (light chain) and residues 143-448 of SEQ ID NO:2 (heavy chain). Activation of FX occurs by limited proteolysis at Arg194, which results in the release of the activation peptide (Aa143-194). Thus, activated FX (FXa) is composed of residues 1-139 of SEQ ID NO:2 (light chain) and residues 195-448 of SEQ ID NO:2 (activated heavy chain). Circulating FX molecules thus comprises the FX zymogen and the activated form of FX which are herein referred to as FX and FXa, respectively, with reference to SEQ ID NO:2. In the present invention FX is intended to cover all natural variants of FX. The term "FX (SEQ ID NO:2) and/or the activated form thereof (FXa)" may also be referred to as "FX/FXa" or "FX(a)".

Antibodies

The term "antibody" herein refers to a protein, derived from an immunoglobulin sequence, which is capable of binding to an antigen or a portion thereof. The term antibody includes, but is not limited to, full length antibodies of any class (or isotype), that is, IgA, IgD, IgE, IgG, IgM and/or IgY. The term antibody includes—but is not limited to— antibodies that are bivalent, such as bispecific antibodies.

Natural full-length antibodies comprise at least four polypeptide chains: two heavy chains (HC) and two light chains (LC) that are connected by disulfide bonds. In some cases, natural antibodies comprise less than four chains, as in the case of the IgNARs found in Chondrichthyes. One class of immunoglobulins of particular pharmaceutical interest is the IgGs. In humans, the IgG class may be divided into four sub-classes IgG1, IgG2, IgG3 and IgG4, based on the sequence of their heavy chain constant regions. The light chains can be divided into two types, kappa and lambda chains, based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable domain ($V_H$) and up to three heavy chain constant ($C_H$) domains: $C_H1$, $C_H2$ and $C_H3$. A light chain may comprise a light chain variable domain ($V_L$) and a light chain constant domain ($C_L$). $V_H$ and $V_L$ regions can be further subdivided into regions of hypervariability, termed complementarity determining regions (CDRs) or hypervariable regions (HvRs), interspersed with regions that are more conserved, termed framework regions (FR). $V_H$ and $V_L$ domains are typically composed of three CDRs and four FRs, arranged from amino-terminus to carboxy-terminus in the following order: FR1, CDR1, FR2, CDR2, FR3, CDR3, FR4. The heavy and light chain variable domains containing the hypervariable regions (CDRs) form a structure that is capable of interacting with an antigen, whilst the constant region of an antibody may mediate binding of the immunoglobulin to host tissues or factors, including, but not limited to various cells of the immune system (effector cells), Fc receptors and the first component, C1q, of the C1 complex of the classical complement system.

Antibodies of the invention may be monoclonal antibodies (mAbs), in the sense that they represent a set of unique heavy and light chain variable domain sequences as expressed from a single B-cell or by a clonal population of B cells. Antibodies of the invention may be produced and purified using various methods that are known to the person skilled in the art.

For example, antibodies may be produced from hybridoma cells. Antibodies may be produced by B-cell expansion. Antibodies or fragment thereof may be recombinantly expressed in mammalian or microbial expression systems, or by in vitro translation.

Antibodies or fragment thereof may also be recombinantly expressed as cell surface bound molecules, by means of e.g. phage display, bacterial display, yeast display, mammalian cell display or ribosome or mRNA display.

Antibodies of the current invention may be isolated. The term "isolated antibody" refers to an antibody that has been separated and/or recovered from (an)other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain(s) the ability to specifically bind to or recognise an antigen, such as FIX/FIXa, FX/FXa or another target molecule, as described herein. Examples of antigen-binding fragments include (but is not limited to) Fab, Fab', $Fab_2$, $Fab'_2$, Fv (typically the combination of $V_L$ and $V_H$ domains of a single arm of an antibody), single-chain Fv (scFv); see e.g. Bird et al. Science 1988; 242:423-426; and Huston et al. PNAS 1988; 85:5879-5883), dsFv, Fd (typically the $V_H$ and $C_H1$ domain), monovalent molecules comprising both a single $V_H$ and a single $V_L$ domain; minibodies, diabodies, triabodies, tetrabodies, and kappa bodies (see, e.g. III et al (1997) Protein Eng 10: 949-57); as well as one or more isolated CDRs or a functional paratope, where the isolated CDRs or antigen-binding residues or polypeptides can be associated or linked together so as to form a functional antibody fragment. These antibody fragments may be obtained using conventional techniques known to those skilled in the art, and the fragments may be screened for utility in the same manner as intact antibodies.

"Fab fragments" of an antibody, including "Fab" and "Fab'$_2$" fragments, can be derived from an antibody by cleavage of the heavy chain in the hinge region on the N-terminal or C-terminal side, respectively, of the hinge cysteine residues connecting the heavy chains of the antibody. A "Fab" fragment includes the variable and constant domains of the light chain and the variable domain and $C_H1$ domain of the heavy chain. "Fab'$_2$" fragments comprise a pair of "Fab'" fragments that are generally covalently linked by their hinge cysteines. A Fab' is formally derived from a Fab'$_2$ fragment by cleavage of the hinge disulfide bonds connecting the heavy chains in the Fab'$_2$. Other chemical couplings than disulfide linkages of antibody fragments are also known in the art. A Fab fragment retains the ability of the parent antibody to bind to its antigen, potentially with a lower affinity. Fab'$_2$ fragments are capable of bivalent binding, whereas Fab and Fab' fragments can only bind monovalently. Generally, Fab fragments lack the constant $C_H2$ and $C_H3$ domains, i.e. the Fc part, where interaction with the Fc receptors and C1q would occur. Thus, Fab fragments are in general devoid of effector functions. Fab fragments may be produced by methods known in the art, either by enzymatic cleavage of an antibody, e.g. using papain to obtain the Fab or pepsin to obtain the Fab'$_2$, Fab fragments including Fab, Fab', Fab'$_2$ may be produced recombinantly using techniques that are well known to the person skilled in the art.

An "Fv" (fragment variable) fragment is an antibody fragment that contains a complete antigen recognition and binding site, and generally comprises one heavy and one light chain variable domain in association that can be covalent in nature, for example in a single chain variable domain fragment (scFv). It is in this configuration that the three hypervariable regions of each variable domain interact to define an antigen-binding site on the surface of the $V_H$-$V_L$ dimer. Collectively, the six hypervariable regions or a subset thereof confer antigen binding specificity to the antibody.

"Single-chain Fv" or "scFv" antibody comprise the $V_H$ and $V_L$ domains of antibody, where these domains are present in a single polypeptide chain. Generally, the Fv polypeptide further comprises a polypeptide linker between the $V_H$ and $V_L$ domains that enables the scFv to form the desired structure for antigen binding. For a review of scFv, see Pluckthun, 1994, In: *The Pharmacology of Monoclonal Antibodies*, Vol. 113, Rosenburg and Moore eds. Springer-Verlag, New York, pp. 269-315.

"Single-chain Fab" or "scFab" antibody comprise the $V_H$, $C_H1$, $V_L$ and $C_L$ domains of an antibody, where these domains are present in a single polypeptide chain. Generally, the Fab polypeptide further comprises a polypeptide linker between either $V_H$ and $C_L$ or $V_L$ and $C_H1$ domains that enables the scFab to form the desired structure for antigen binding (Koerber et al. (2015) *J Mol Biol.* 427:576-86).

The term "diabodies" refers to small antibody fragments with two antigen-binding sites, in which fragments comprise a heavy chain variable domain ($V_H$) connected to a light chain variable domain ($V_L$) in the same polypeptide chain ($V_H$ and $V_L$). By using a linker that is too short to allow pairing between the two variable domains on the same chain, the variable domains are forced to pair with complementary domains of another chain, creating two antigen-binding sites.

The expression "linear antibodies" refers to antibodies as described in Zapata et al. (1995) *Protein Eng.* 8: 1057-1062. Briefly, these antibodies contain a pair of tandem Fd segments ($V_H$—$C_H1$-$V_H$-$C_H1$) that, together with complementary light chain polypeptides, form a pair of antigen binding regions. Linear antibodies can be bispecific or monospecific.

Antibody fragments may be obtained using conventional recombinant or protein engineering techniques and the fragments can be screened for binding to FIX and the activated form thereof, FX or another function, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of the antibody, or a variant of any one of the antibodies disclosed herein. An antibody of the invention may be, or may comprise, an antigen binding portion of one of these antibodies, or variants thereof. For example, an antibody of the invention may be a Fab fragment of one of these antibodies or variants thereof, or it may be a single chain antibody derived from one of these antibodies, or a variant thereof. Also, an antibody of the invention may be a combination of a full length antibody and fragment thereof.

The term "one-armed" as used herein, refers to a particular type of monovalent antibody constituted by an antibody heavy chain, a truncated heavy chain lacking the Fab region, and a single light chain.

The term "monospecific" antibody as used herein, refers to an antibody which is capable of binding to one particular epitope (including but not limited to bivalent antibodies).

The term "bispecific" antibody as used herein, refers to an antibody which is capable of binding to two different antigens or two different epitopes on the same antigen.

The term "trispecific" antibody as used herein, refers to an antibody which is capable of binding to three different antigens or three different epitopes on the same antigen or three different epitopes present on two different antigens.

The term "multispecific" antibody as used herein, refers to an antibody which is capable of binding to two or more different antigens or two or more different epitopes on the same antigen. Multispecific antibodies thus comprise bi- and trispecific antibodies.

Bispecific antibodies in full length IgG format can be generated by fusion of two individual hybridomas to form a hybrid quadroma which produces a mixture of antibodies including a fraction of bispecific heterodimerising antibodies (Chelius D. et al.; *MAbs.* 2010 May-June; 2(3): 309-319). Bispecific heterodimerising antibodies may alternatively be produced by using recombinant technologies. Heterodimerisation can also be achieved by engineering the dimerisation interface of the Fc region to promote heterodimerisation. One example hereof is the so-called knob-in-hole mutations where sterically bulky side chains (knobs) are introduced in one Fc matched by sterically small side chains (holes) on the opposite Fc thereby creating steric complementarity promoting heterodimerisation. Other methods for engineered heterodimerisation Fc interfaces are electrostatic complementarity, fusion to non-IgG heterodimerisation domains or utilising the natural Fab-arm exchange phenomenon of human IgG4 to control heterodimerisation. Examples of heterodimerised bispecific antibodies are well described in the literature, e.g. (Klein C, et al.; *MAbs.* 2012 November-December; 4(6): 653-663). Special attention has to be paid to the light chains in heterodimeric antibodies. Correct pairing of LCs and HCs can be accomplished by the use of a common light chain. Again engineering of the LC/HC interface can be used to promote heterodimerisation or light chain cross-over engineering as in CrossMabs. In vitro re-assembly under mildly reducing conditions of antibodies from two individual IgGs containing appropriate mutations can also be used to generate bispecific antibodies (e.g. Labrijn et al., *PNAS,* 110, 5145-5150 (2013)). Also the natural Fab-arm exchange method is reported to ensure correct light chains paring. Multispecific antibody-based molecules may also be expressed recombinantly as fusion proteins combining the natural modules of IgGs to form multispecific and multivalent antibody derivatives as described in the literature. Examples of fusion antibodies are DVD-Igs, IgG-scFV, Diabodies, DARTs etc. Specific detection or purification tags, half-life extension moieties or other components can be incorporated in the fusion proteins. Additional non-IgG modalities may also be incorporated in the fusion proteins. Bispecific full length antibodies based on Fc heterodimerisation are commonly referred to as asymmetic IgGs, irrespective of the LC paring methodology.

Generally, bispecific antibodies may be produced in a variety of molecular formats as reviewed by Brinkmann et al. (Brinkmann et al. The making of bispecific antibodies. *Mabs* 9, 182-212 (2017)).

Multispecific antibody-based molecules may also be produced by chemical conjugation or coupling of individual full length IgGs or coupling of fragments of IgGs to form multispecific and multivalent antibody derivatives as described in the literature. Examples are chemically coupled Fab fragments, IgG-dimer etc. Specific detection or purification tags, half-life extension molecules or other components can be incorporated in the conjugate proteins. Additional non-IgG polypeptide may also be incorporated in the fusion proteins. Multispecific molecules may also be produced by combining recombinant and chemical methods including those described above.

In one aspect, an antibody of the invention is a chimeric antibody, a human antibody or a humanised antibody. Such antibody can be generated by using, for example, suitable antibody display or immunization platforms or other suitable platforms or methods known in the field. The term "human antibody", as used herein, is intended to include antibodies having variable domains in which at least a portion of a framework region and/or at least a portion of a CDR region are derived from human germline immunoglobulin sequences. For example, a human antibody may have variable domains in which both the framework and CDR regions are derived from human germline immunoglobulin sequences. Furthermore, if the antibody contains a constant region, the constant region or a portion thereof is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalised cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

Human antibodies may be produced by recombinant methods known in the art.

The term "human antibody derivative" refers to any modified form of the human antibody, such as a conjugate of the antibody and another agent or antibody.

The term "humanised antibody", as used herein, refers to a human/non-human antibody that contains a sequence (CDR regions or parts thereof) derived from a non-human immunoglobulin. A humanised antibody is, thus, a human immunoglobulin (recipient antibody) in which residues from at least a hypervariable region of the recipient are replaced by residues from a hypervariable region of an antibody from a non-human species (donor antibody) such as from a mouse, rat, rabbit or non-human primate, which have the desired specificity, affinity, sequence composition and functionality. In some instances, framework (FR) residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (back-mutation) of the amino acid residue from the donor antibody has beneficial impact on the properties of the humanised antibody. In addition to donor antibody derived back-mutations, the humanised antibody can be engineered by introduction of germline residues in the CDR or framework regions, elimination of immunogenic epitopes, site-directed mutagenesis, affinity maturation, etc. Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and a chemical agent or a conjugate of the antibody with another antibody.

The term "chimeric antibody", as used herein, refers to an antibody comprising portions of antibodies derived from two or more species. For example, the genes encoding such antibody comprise genes encoding variable domains and genes encoding constant domains originated from two different species. For example, the genes encoding variable domains of a mouse monoclonal antibody may be joined to the genes encoding the constant domains of an antibody of human origin.

The fragment crystallisable region ("Fc region"/"Fc domain") of an antibody is the C-terminal region of an antibody, which comprises the hinge and the constant $C_H2$ and $C_H3$ domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprising one or more, and perhaps all of the following mutations that will result in decreased affinity to certain Fc-gamma receptors (L234A, L235E, and G237A) and in reduced C1q-mediated complement fixation (A330S and P331 S), respectively (residue numbering according to the EU index). Alternatively, other amino acid substitutions, and combinations thereof and combinations with the above mentioned, known in the art to lead to altered (reduced or increased) Fc-gamma receptor binding may be used.

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed. In one embodiment the hinge region of the antibody is modified such that the number of cysteine residues in the hinge region is altered, e.g., increased or decreased. This approach is described further for instance in U.S. Pat. No. 5,677,425 by Bodmer et al.

The constant region may be modified to stabilise the antibody, e.g., to reduce the risk of a bivalent antibody separating into half antibodies. For example, in an IgG4 constant region, residue S228 (according to the EU numbering index and S241 according to Kabat) may be mutated to a proline (P) residue to stabilise inter heavy chain disulphide bridge formation at the hinge (see, e.g., Angal et al. Mol Immunol. 1993; 30:105-8).

Antibodies or fragment thereof may be defined in terms of their complementarity-determining regions (CDRs). The term "complementarity-determining region" or "hypervariable region", when used herein, refers to the regions of an antibody in which amino acid residues involved in antigen-binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al. 1991; Sequences of Proteins of Immunological Interest, Fifth Edition, U.S. Department of Health and Human Services, NIH Publication No. 91-3242) Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol. 1987; 196:901-917). Typically, the numbering of amino acid residues in this region is performed by the method described in Kabat et al. supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those $V_H$ or $V_L$ amino acid residues that are not within the CDRs, as defined herein.

An antibody of the invention may comprise a CDR region from one or more of the specific antibodies disclosed herein.

The term "procoagulant antibody" refers to an antibody which potentiates blood coagulation for example by accelerating the process of blood coagulation and/or increasing the enzymatic activity of one or more coagulation factors.

The term "procoagulant activity" refers to the ability of a compound, such as an antibody, to potentiate blood coagulation for example by accelerating the process of blood coagulation and/or increasing the enzymatic activity of one or more coagulation factors.

The term "antigen" (Ag) refers to the molecular entity used for immunisation of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunisation process, or other process, e.g. phage display, used for generating the Ab.

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab binds, i.e. the area or region in physical contact with the Ab. Physical contact may be defined using various criteria (e.g. a distance cut-off of 2-6 Å, such as 3 Å, such as 3.5 Å such as 4 Å, such as 4.5 Å, such as 5 Å; or solvent accessibility) for atoms in the Ab and Ag molecules.

FIX/FIXa and FX/FXa may comprise a number of different epitopes, which may include, without limitation, (1) linear peptide epitopes (2) conformational epitopes which consist of one or more non-contiguous amino acids located near each other in the mature FIX/FIXa or FX/FXa conformation; and (3) epitopes which consist, either in whole or part, of molecular structures covalently attached to FIX/FIXa or FX/FXa, such as carbohydrate groups.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen Deuterium eXchange Mass Spectrometry (HDX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

In the context of an X-ray derived crystal structure defined by spatial coordinates of a complex between an Ab, e.g. a Fab fragment, and its Ag, the term epitope is herein, unless otherwise specified or contradicted by context, specifically defined as FIX/FIXa or FX residues characterized by having a heavy atom (i.e. a non-hydrogen atom) within a distance of 3.5 Å, from a heavy atom in the Ab.

Epitopes described at the amino acid level, e.g. determined from an X-ray structure, are said to be identical if they contain the same set of amino acid residues. Epitopes are said to overlap if at least one amino acid residue is shared by the epitopes. Epitopes are said to be separate (unique) if no amino acid residue is shared by the epitopes.

The definition of the term "paratope" is derived from the above definition of "epitope" by reversing the perspective. Thus, the term "paratope" refers to the area or region on the Ab to which an Ag binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ab residues characterized by having a heavy atom (i.e. a non-hydrogen atom) within a distance of 3.5 Å from a heavy atom in FIX/FIXa or FX.

The epitope and paratope for a given antibody (Ab)/antigen (Ag) pair may be identified by routine methods. For example, the general location of an epitope may be determined by assessing the ability of an antibody to bind to different fragments or variants of FIX/FIXa or FX. The specific amino acids within FIX/FIXa or FX that make contact with an antibody (epitope) and the specific amino acids in an antibody that make contact with FIX/FIXa or FX (paratope) may also be determined using routine methods. For example, the antibody and target molecule may be combined and the Ab:Ag complex may be crystallised. The crystal structure of the complex may be determined and used to identify specific sites of interaction between the antibody and its target.

Epitopes on an antigen may comprise one or more hot-spot residues, i.e. residues which are particularly important for the interaction with the cognate antibody, and where interactions mediated by the side chain of said hot-spot residue contribute significantly to the binding energy for the antibody/antigen interaction (Peng et al. (2014) *PNAS* 111, E2656-E2665). Hot-spot residues can be identified by testing variants of the antigen (here FIX/FIXa and FX), where single epitope residues have been substituted by e.g. alanine, for binding to the cognate antibody. If substitution of an epitope residue with alanine has a strong impact on binding to the antibody, said epitope residue is considered a hot-spot residue, and therefore of particular importance for binding of the antibody to the antigen.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope.

Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes. Thus, in some embodiments antibodies of the invention will bind to the same epitope as at least one of the antibodies specifically disclosed herein.

Competition assays for determining whether an antibody competes for binding with, an anti-FIX/FIXa or anti-X antibody disclosed herein are known in the art. Exemplary competition assays include immunoassays (e.g., ELISA assays, RIA assays), surface plasmon resonance analysis (e.g. using a BIAcore™ instrument), biolayer interferometry (ForteBio®) and flow cytometry.

Typically, a competition assay involves the use of an antigen bound to a solid surface or expressed on a cell surface, a test FIX- or FIXa binding antibody and a reference antibody. The reference antibody is labelled and the test antibody is unlabelled. Competitive inhibition is measured by determining the amount of labelled reference antibody bound to the solid surface or cells in the presence of the test antibody. Usually the test antibody is present in excess (e.g., 1, 5, 10, 20, 100, 1000, 10000 or 100000-fold). Antibodies identified as being competitive in the competition assay (i.e., competing antibodies) include antibodies binding to the same epitope, or overlapping epitopes, as the reference antibody, and antibodies binding to an adjacent epitope sufficiently proximal to the epitope bound by the reference antibody for steric hindrance to occur.

In an exemplary competition assay, a reference anti-FIX or anti-FIXa antibody is biotinylated using commercially available reagents. The biotinylated reference antibody is mixed with serial dilutions of the test antibody or unlabelled reference antibody (self-competition control) resulting in a mixture of various molar ratios (e.g., 1, 5, 10, 20, 100, 1000, 10000 or 100000-fold) of test antibody (or unlabelled reference antibody) to labelled reference antibody. The antibody mixture is added to a FIX or FIXa polypeptide coated-ELISA plate. The plate is then washed, and horseradish peroxidase (HRP)-strepavidin is added to the plate as the detection reagent. The amount of labelled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are made using a spectrometer (e.g. SpectraMax® M2 spectrometer (Molecular Devices)). The response (OD units) corresponding to zero percent inhibition is determined from wells without any competing antibody. The response (OD units) corresponding to 100% inhibition, i.e. the assay background, is determined from wells without any labelled reference antibody or test antibody. Percent inhibition of labelled reference antibody to FIX or FIXa by the test antibody (or the unlabelled reference antibody) at each concentration is calculated as follows: % inhibition=(1−(OD units−100% inhibition)/(0% inhibition−100% inhibition))*100.

The person skilled in the art will understand that similar assays may be performed to determine if two or more anti-FX/FXa antibodies shares a binding region, a bin and/or competitively binds the antigen. Persons skilled in the art will also appreciate that the competition assay can be performed using various detection systems known in the art.

A test antibody competes with the reference antibody for binding to the antigen if an excess of one antibody (e.g., 1, 5, 10, 20, 100, 1000, 10000 or 100000-fold) inhibits binding of the other antibody, e.g., by at least 50%, 75%, 90%, 95% or 99%, as measured in a competitive binding assay.

Unless otherwise indicated competition is determined using a competitive ELISA assay as described above.

The term "binding affinity" is herein used as a measure of the strength of a non-covalent interaction between two molecules, e.g. an antibody, or fragment thereof, and an antigen. The term "binding affinity" is used to describe monovalent interactions.

Binding affinity between two molecules, e.g. an antibody, or fragment thereof, and an antigen, through a monovalent interaction may be quantified by determining the equilibrium dissociation constant ($K_D$). $K_D$ can be determined by measurement of the kinetics of complex formation and dissociation, e.g. by the Surface Plasmon Resonance (SPR) method or the Isothermal Titration Calorimetry (ITC) method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D = k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

The value of the dissociation constant can be determined directly by well-known methods. Standard assays to evaluate the binding ability of ligands such as antibodies towards targets are known in the art and include, for example, ELISAs, Western blots, RIAs, and flow cytometry analysis. The binding kinetics and binding affinity of the antibody also can be assessed by standard assays known in the art, such as SPR. Preferably, however, isothermal titration calorimetry (ITC) may be used to measure affinities for an antibody/target interaction as well as to derive thermodynamic parameters for the interaction.

A competitive binding assay can be conducted in which the binding of the antibody to the target is compared to the binding of the target by another ligand of that target, such as another antibody.

An antibody of the invention may have a $K_D$ for its target of $1 \times 10^{-4}$M or less, $1 \times 10^{-5}$M or less, $1 \times 10^{-6}$M or less, $1 \times 10^{-7}$M or less, $1 \times 10^{-8}$M or less, or $1 \times 10^{-9}$M or less, or $1 \times 10^{-10}$M or less, $1 \times 10^{-11}$M or less, $1 \times 10^{-12}$M or less, $1 \times 10^{-13}$M or less or $1 \times 10^{-14}$M or less.

The $K_D$ of an antibody of the invention may be less than 100 µM such as less than 10 µM, such as less than 1 µM, such as less than 0.9 µM, such as less than 0.8 µM, such as less than 0.7 µM, such as less than 0.6 µM, such as less than 0.5 µM, such as less than 0.4 µM, such as less than 0.3 µM, such as less than 0.2 µM, such as less than 0.1 µM.

In one such embodiment the antibody is a bispecific antibody comprising an anti-FX arm with a $K_D$ towards FX of less than 100 µM such as less than 10 µM, such as less than 1 µM, such as less than 0.9 µM, such as less than 0.8 µM, such as less than 0.7 µM, such as less than 0.6 µM, such as less than 0.5 µM, such as less than 0.4 µM, such as less than 0.3 µM, such as less than 0.2 µM, such as less than 0.1 µM, such as less than 0.09 µM, such as less than 0.08 µM, such as less than 0.07 µM, such as less than 0.06 µM, such as less than 0.05 µM, such as less than 0.04 µM, such as less than 0.03 µM, such as less than 0.02 µM, such as less than 0.01 µM, such as less than 9 nM, such as less than 8 nM, such as less than 7 nM, such as less than 6 nM, such as less than 5 nM, such as less than 4 nM, such as less than 3 nM, such as less than 2 nM, such as less than 1 nM such as less than 0.5 nM.

The antibodies and antibody fragment thereof as described herein may be combined with other antibodies and antibody fragments known in the art creating bispecific, trispecific or multispecific antibody molecules. Compounds mimicking FVIII cofactor function have previously been created using other FIX/IXa and FX/Xa binding domains, which may potentially each substitute for the FIX/IXa and/or FX/Xa binding domains described herein. It is thus clear that the FIX/IXa and FX/Xa binding domains of the present invention are of separate interest as individual molecules, as well as "intermediates" as part of a bi-, tri- or multispecific antibody comprising at least one FIX/IXa and/or FX/Xa binding domain.

The activity of procoagulant antibodies including bi-, tri and multispecific antibodies may be determined by methods known in the art. Standard assays include whole blood-Thrombin-Generation Test (TGT), measuring of clotting time by thrombelastography (TEG) and FXa generation assays.

Identity

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al. SIAM J. Applied Math. 1988; 48:1073. Preferred methods for determining identity are designed to give the largest match between the sequences tested. Methods of determining identity are described in publicly available computer programs. Preferred computer program methods for determining identity between two sequences include the GCG program package, including GAP (Devereux et al. Nucl. Acid. Res. 1984; 12:387); Genetics Computer Group, University of Wisconsin, Madison, Wis.), BLASTP, BLASTN, and FASTA (Altschul et al. J. Mol. Biol. 1990; 215:403-410). The BLASTX program is publicly available from the National Center for Biotechnology Information (NCBI) and other sources (BLAST Manual, Altschul et al. NCB/NLM/NIH Bethesda, Md. 20894; Altschul et al. supra). The well-known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al. 1978; Atlas of Protein Sequence and Structure, vol. 5, supp. 3 for the PAM 250 comparison matrix; Henikoff et al. PNAS 1992; 89:10915-10919 for the BLOSUM 62 comparison matrix) is also used by the algorithm. Preferred parameters for a peptide sequence comparison include the following: Algorithm:

Needleman et al. J. Mol. Biol. 1970; 48:443-453; Comparison matrix: BLOSUM 62 from Henikoff et al. PNAS 1992; 89:10915-10919; Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

The term "similarity" is a related concept, but in contrast to "identity", refers to a sequence relationship that includes both identical matches and conservative substitution matches. If two polypeptide sequences have, for example, (fraction (10/20)) identical amino acids, and the remainder are all non-conservative substitutions, then the percent identity and similarity would both be 50%. If, in the same example, there are 5 more positions where there are conservative substitutions, then the percent identity is 25% and the percent similarity would be 75% ((fraction (15/20))). Therefore, in cases where there are conservative substitutions, the degree of similarity between two polypeptides will be higher than the percent identity between those two polypeptides.

Pharmaceutical Formulations

In another aspect, the present invention provides compositions and formulations comprising compounds of the invention, such as the antibodies described herein. For example, the invention provides a pharmaceutical composition that comprises one or more antibodies of the invention, formulated together with a pharmaceutically acceptable carrier.

Accordingly, one object of the invention is to provide a pharmaceutical formulation comprising such an antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabilizer, or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19$^{th}$ edition, 1995.

In one embodiment the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

Administration

A compound of the invention, such as an antibody, may be administered parenterally, such as intravenously, such as intramuscularly, such as subcutaneously. Alternatively, an antibody of the invention may be administered via a non-parenteral route, such as periorally or topically. An antibody of the invention may be administered prophylactically. An antibody of the invention may be administered therapeutically (on demand).

Dosages

The dose of the compounds to be delivered may be from about 0.01 mg to 500 mg of the compound per day, preferably from about 0.1 mg to 250 mg per day, and more preferably from about 0.5 mg to about 250 mg per day, per week, per second week or per month as loading and maintenance doses, depending on the severity of the condition. A suitable dose may also be adjusted for a particular compound based on the properties of that compound, including its in vivo half-life or mean residence time and its biological activity. For example, compounds to be delivered could in one embodiment be administered once weekly, or in another embodiment once every second week or in another embodiment one monthly and in either of said embodiments in a dose of for example 0.25, 0.5, 1, 1.5, 2, 2.5, 3, 3.5, 4, 4.5, 5, 5.5, 6, 6.5, 7, 7.5, 8, 8.5, 9, 9.5 or 10 mg per kg body weight.

The compositions containing the compounds as disclosed herein can be administered for prophylactic and/or in some embodiments therapeutic treatments. In therapeutic applications, compositions are administered to a subject already suffering from a disease, such as any bleeding disorder as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject.

EMBODIMENTS

In one embodiment an antibody of the invention is capable of binding an epitope comprising residue H256 of FIX (SEQ ID NO:1) or the activated form thereof (FIXa).

In one embodiment an antibody of the invention is capable of binding an epitope comprising residue H257 of FIX (SEQ ID NO:1) or the activated form thereof FIXa.

In one embodiment an antibody of the invention is capable of binding an epitope comprising residue N258 of FIX (SEQ ID NO:1) or the activated form thereof (FIXa).

In one embodiment an antibody of the invention is capable of binding an epitope comprising residue K293 of FIX (SEQ ID NO:1) or the activated form thereof (FIXa).

In one embodiment an antibody of the invention is capable of binding an epitope comprising residue K301 of FIX (SEQ ID NO:1) or the activated form thereof (FIXa).

In one embodiment an antibody of the invention is capable of binding an epitope comprising residue D332 of FIX (SEQ ID NO:1) or the activated form thereof (FIXa).

In one embodiment an antibody of the invention is capable of binding an epitope comprising residue R333 of FIX (SEQ ID NO:1) or the activated form thereof (FIXa).

In one embodiment an antibody of the invention is capable of binding an epitope comprising residue A334 of FIX (SEQ ID NO:1) or the activated form thereof (FIXa).

In one embodiment an antibody of the invention is capable of binding an epitope comprising residue T335 of FIX (SEQ ID NO:1) or the activated form thereof (FIXa).

In one embodiment an antibody of the invention is capable of binding an epitope comprising residue L337 of FIX (SEQ ID NO:1) or the activated form thereof (FIXa).

In one embodiment an antibody of the invention is capable of binding an epitope comprising residue R338 of FIX (SEQ ID NO:1) or the activated form thereof (FIXa).

In one embodiment an antibody of the invention is capable of binding an epitope comprising residue S339 of FIX (SEQ ID NO:1) or the activated form thereof (FIXa).

In one embodiment an antibody of the invention is capable of binding an epitope comprising residue T340 of FIX (SEQ ID NO:1) or the activated form thereof (FIXa).

In one embodiment an antibody of the invention is capable of binding an epitope comprising residue K341 of FIX (SEQ ID NO:1) or the activated form thereof (FIXa).

In one embodiment an antibody of the invention is capable of binding an epitope comprising residue T343 of FIX (SEQ ID NO:1) or the activated form thereof (FIXa).

In one embodiment an antibody of the invention is capable of binding an epitope comprising residue N346 of FIX (SEQ ID NO:1) or the activated form thereof (FIXa).

In one embodiment an antibody of the invention is capable of binding an epitope comprising residue R403 of FIX (SEQ ID NO:1) or the activated form thereof (FIXa).

In one embodiment an antibody of the invention is capable of binding an epitope comprising residue Y404 of FIX (SEQ ID NO:1) or the activated form thereof (FIXa).

In one embodiment an antibody of the invention is capable of binding an epitope comprising residue N406 of FIX (SEQ ID NO:1) or the activated form thereof (FIXa).

In one embodiment an antibody of the invention is capable of binding an epitope comprising residue W407 of FIX (SEQ ID NO:1) or the activated form thereof (FIXa).

In one embodiment an antibody of the invention is capable of binding an epitope comprising residue E410 of FIX (SEQ ID NO:1) or the activated form thereof (FIXa).

In one embodiment an antibody of the invention is capable of binding an epitope comprising residue K411 of FIX (SEQ ID NO:1) or the activated form thereof (FIXa).

In one embodiment an antibody of the invention is capable of binding an epitope comprising residues L337, R338, S339, T340, K341, and T343 of FIX (SEQ ID NO:1) or the activated form thereof (FIXa).

In one embodiment an antibody of the invention is capable of binding an epitope comprising residues K301, D332, R333, A334, T335, R338, and N346 of FIX (SEQ ID NO:1) or the activated form thereof (FIXa).

In one embodiment an antibody of the invention is capable of binding an epitope comprising residues H256, H257, N258, K293, R403, Y404, N406, W407, E410, and K411 of FIX (SEQ ID NO:1) or the activated form thereof (FIXa).

In one embodiment an antibody of the invention is capable of binding FIX (SEQ ID NO:1) or the activated form thereof (FIXa), wherein the antibody competes with Fab7236 for binding to FIX.

In one embodiment an antibody of the invention is capable of binding FIX (SEQ ID NO:1) or the activated form thereof (FIXa), wherein the antibody competes with Fab7237 for binding to FIX.

In one embodiment an antibody of the invention is capable of binding FIX (SEQ ID NO:1) or the activated form thereof (FIXa), wherein the antibody competes with Fab7238 for binding to FIX.

In one embodiment an antibody of the invention binds FIX (SEQ ID NO:1) or the activated form thereof (FIXa), wherein the antibody belongs to the same "bin" as Fab7236.

In one embodiment an antibody of the invention binds FIX (SEQ ID NO:1) or the activated form thereof (FIXa), wherein the antibody belongs to the same "bin" as Fab7237.

In one embodiment an antibody of the invention binds FIX (SEQ ID NO:1) or the activated form thereof (FIXa), wherein the antibody belongs to the same "bin" as Fab7238.

In one embodiment an antibody of the invention is capable of binding FX (SEQ ID NO:2) or the activated form thereof FXa, wherein the antibody competes with an antibody comprising the CDRs of mAb1-6723.

In one embodiment an antibody of the invention is capable of binding FX/FXa, wherein the antibody comprises the variable domains of mAb1-6723 according to SEQ ID NO:21 and SEQ ID NO:22.

In one embodiment an antibody of the invention is capable of specifically binding FX/FXa, wherein the antibody comprises the CDRs of mAb1-6723 according to SEQ ID NO:21 and SEQ ID NO:22.

In one embodiment an antibody of the invention is capable of binding FX/FXa, wherein the antibody belongs to the same "bin" as a Fab of comprising the variable domains of mAb1-6723 according to SEQ ID NO:21 and SEQ ID NO:22.

In one embodiment an antibody of the invention is capable of specifically binding FX/FXa, wherein the antibody belongs to the same "bin" as mAb1-6723 according to SEQ ID NO:21 and SEQ ID NO:22.

In one embodiment an antibody of the invention is capable of specifically binding FX/FXa, wherein the antibody belongs to the same "bin" as an antibody or Fab comprising the antigen binding domain according to SEQ ID NO:21 and SEQ ID NO:22.

In one embodiment an antibody of the invention is capable of binding FX/FXa, wherein the antibody competes with an antibody comprising the CDRs of mAb1-1371.

In one embodiment an antibody of the invention is capable of binding FX/FXa, wherein the antibody comprises the variable domains of mAb1-1371 according to SEQ ID NO:65 and SEQ ID NO:66.

In one embodiment an antibody of the invention is capable of binding FX/FXa, wherein the antibody comprises the CDRs of mAb1-1371 according to SEQ ID NO:65 and SEQ ID NO:66.

In one embodiment an antibody of the invention is capable of binding FX/FXa, wherein the antibody belongs to the same "bin", herein referred to as "Bin A", as a Fab of comprising the variable domains of mAb1-1371 according to SEQ ID NO:65 and SEQ ID NO:66.

In one embodiment an antibody of the invention is capable of binding FX/FXa, wherein the antibody belongs to the same "bin" as mAb1-1371 according to SEQ ID NO:65 and SEQ ID NO:66.

In one embodiment an antibody of the invention is capable of binding FX/FXa, wherein the antibody belongs to the same "bin" as an antibody or Fab comprising the antigen binding domain according to SEQ ID NO:65 and SEQ ID NO:66.

In one embodiment an antibody of the invention is capable of specifically binding FX/FXa, wherein the antibody competes with an antibody comprising the CDRs of mAb1-1376, mAb1-6705, mAb1-7388 or mAb1-7563. Such antibodies are herein referred to as belonging to Bin B.

In one embodiment an antibody of the invention is capable of binding FX/FXa, wherein the antibody comprises the variable domains of mAb1-1376, mAb1-6705, mAb1-7388 or mAb1-7563 as identified by SEQ ID NO:67 and 68, SEQ ID NO:23 and 24, SEQ ID NO:39 and 40, and SEQ ID NO:59 and 60, respectively.

In one embodiment an antibody of the invention is capable of binding FX/FXa, wherein the antibody comprises the CDRs of mAb1-1376, mAb1-6705, mAb1-7388 or mAb1-7563 as identified by SEQ ID NO:67 and 68, SEQ ID NO:23 and 24, SEQ ID NO:39 and 40, and SEQ ID NO:59 and 60, respectively.

In one embodiment an antibody of the invention is capable of binding FX/FXa, wherein the antibody belongs to the same "bin" as a Fab of comprising the variable domains of mAb1-1376, mAb1-6705, mAb1-7388 or mAb1-7563 as identified by SEQ ID NO:67 and 68, SEQ ID NO:23 and 24, SEQ ID NO:39 and 40, and SEQ ID NO:59 and 60, respectively.

In one embodiment an antibody of the invention capable of binding FX/FXa, wherein the antibody belongs to the same "bin" as mAb1-1376, mAb1-6705, mAb1-7388 or mAb1-7563 as identified by SEQ ID NO:67 and 68, SEQ ID NO:23 and 24, SEQ ID NO:39 and 40, and SEQ ID NO:59 and 60, respectively.

In one embodiment an antibody of the invention is capable of binding FX/FXa, wherein the antibody belongs to the same "bin" as an antibody or Fab comprising the antigen binding domain according to SEQ ID NO:67 and 68, SEQ ID NO:23 and 24, SEQ ID NO:39 and 40, or SEQ ID NO:59 and 60.

In one embodiment an antibody of the invention is capable of binding FX/FXa, wherein the antibody comprises the CDRs or variable domains of an antibody selected from the group consisting of: mAb1-6723, 1-6716, 1-6721, 1-6730, 1-6731, 1-6737, 1-6754, 1-7378, 1-7413, 1-7424, 1-7466, 1-7481, 1-7483 and mAb1-7591.

In one embodiment an antibody of the invention is capable of binding FX/FXa, wherein the antibody comprises the CDRs or variable domains of an antibody selected from the group consisting of: mAb1-6723, 1-6716, 1-6721, 1-6730, 1-6731, 1-6737, 1-6754, 1-7378, 1-7413, 1-7424, 1-7466, 1-7481, 1-7483, 1-7591, 1-7388, 1-7563, 1-7462 and mAb1-7571.

In one embodiment an antibody of the invention is capable of binding FX/FXa, wherein the antibody belongs to the same "bin" as a mAb selected from the group of mAbs comprising the variables sequences or the CDRs thereof selected from: SEQ ID NO:21 and 22, SEQ ID NO:25 and 26, SEQ ID NO:27 and 28, SEQ ID NO:29 and 30, SEQ ID NO:31 and 32, SEQ ID NO:33 and 34, SEQ ID NO:35 and 36, SEQ ID NO:37 and 38, SEQ ID NO:39 and 40, SEQ ID NO:41 and 42, SEQ ID NO:43 and 44, SEQ ID NO:45 and 46, SEQ ID NO:51 and 52, SEQ ID NO:53 and 54, SEQ ID NO:55 and 56, SEQ ID NO:57 and 58, SEQ ID NO:59 and 60, SEQ ID NO:61 and 62, and SEQ ID NO:63 and 64. This "bin" of antibodies have herein been referred to as Bin C and exemplified with a large number of individual antibodies, such as mAb1-6723, 1-6716, 1-6721, 1-6730, 1-6731, 1-6737, 1-6754, 1-7378, 1-7413, 1-7424, 1-7466, 1-7481, 1-7483, 1-7591, 1-7388, 1-7563, 1-7462 and mAb1-7571.

In one embodiment an antibody of the invention is capable of binding FX/FXa, wherein the antibody competes for binding to FX, FX zymogen or FXa with a reference antibody selected from the group of antibodies consisting of mAbs comprising the variables sequences or the CDRs thereof selected from: SEQ ID NO:21 and 22, SEQ ID NO:25 and 26, SEQ ID NO:27 and 28, SEQ ID NO:29 and 30, SEQ ID NO:31 and 32, SEQ ID NO:33 and 34, SEQ ID NO:35 and 36, SEQ ID NO:37 and 38, SEQ ID NO:41 and 42, SEQ ID NO:43 and 44, SEQ ID NO:53 and 54, SEQ ID NO:55 and 56, SEQ ID NO:57 and 58, and SEQ ID NO:63 and 64.

In one embodiment the antibody or antigen-binding fragment thereof according to the invention competes for binding to FX/FXa with an antigen-binding fragment comprising the CDRs of SEQ ID NO:21 and 22, SEQ ID NO:25 and 26, SEQ ID NO:27 and 28, SEQ ID NO:29 and 30, SEQ ID NO:31 and 32, SEQ ID NO:33 and 34, SEQ ID NO:35 and 36, SEQ ID NO:37 and 38, SEQ ID NO:41 and 42, SEQ ID NO:43 and 44, SEQ ID NO:53 and 54, SEQ ID NO:55 and 56, SEQ ID NO:57 and 58, or SEQ ID NO:63 and 64.

In one embodiment an antibody of the invention is capable of binding FX/FXa, wherein the antibody competes with an antibody comprising the CDRs of mAb1-7447, 1-7441, 1-7571 or 1-7462. These are herein referred to as antibodies of Bin D.

In one embodiment an antibody of the invention is capable of binding FX/FXa, wherein the antibody comprises the variable domains of mAb1-7447, 1-7441, 1-7571 or 1-7462 according to SEQ ID NO:47 and 48, SEQ ID NO:45 and 46, SEQ ID NO:51 and 53 or SEQ ID NO:61 and 62, respectively.

In one embodiment an antibody of the invention is capable of binding FX/FXa, wherein the antibody comprises the variable domains of mAb1-7447 or 1-7441, according to SEQ ID NO:47 and 48, SEQ ID NO:45 and 46, respectively.

In one embodiment an antibody of the invention is capable of binding FX/FXa, wherein the antibody comprises the CDRs of mAb1-7447, 1-7441, 1-7571 or 1-7462 according to SEQ ID NO:47 and 48, SEQ ID NO:45 and 46, SEQ ID NO:51 and 53 or SEQ ID NO:61 and 62, respectively.

In one embodiment an antibody of the invention is capable of binding FX/FXa according to SEQ ID NO:2, wherein the antibody belongs to the same "bin" as a Fab comprising the variable domains of mAb1-7447, 1-7441, 1-7571 or mAb1-7462 according to SEQ ID NO:47 and 48, SEQ ID NO:45 and 46, SEQ ID NO:51 and 53 or SEQ ID NO:61 and 62, respectively.

In one embodiment an antibody of the invention is capable of binding FX/FXa, wherein the antibody belongs to the same "bin" as mAb1-7447, 1-7441, 1-7571 or mAb1-7462 according to SEQ ID NO:47 and 48, SEQ ID NO:45 and 46, SEQ ID NO:51 and 53 or SEQ ID NO:61 and 62 respectively.

In one embodiment an antibody of the invention is capable of binding FX/FXa, wherein the antibody belongs to the same "bin" as an antibody or Fab comprising the antigen-binding domain according to SEQ ID NO:47 and 48, SEQ ID NO:45 and 46, SEQ ID NO:51 and 53 or SEQ ID NO:61 and 62.

In one embodiment an antibody of the invention is an antibody according to any of the previous embodiments, wherein the antibody specifically binds the FX zymogen.

In such embodiment the antibody specifically binds the FX zymogen according to amino acid residues 1-139, 143-448 of SEQ ID NO:2.

In one embodiment an antibody of the invention is an antibody according to any of the previous embodiments, wherein the antibody binds FX.

In one embodiment an antibody of the invention is an antibody according to any of the previous embodiments, wherein the antibody binds FXa.

In one such embodiment the antibody specifically binds FXa according to amino acid residues 1-139, 195-448 of SEQ ID NO:2.

In one embodiment the antibody is a monospecific antibody. In one embodiment the antibody is a multispecific antibody. In one such embodiment the antibody is a bispecific antibody. In one such embodiment the bispecific antibody is capable of binding to FIX or the activated form thereof (FIXa) and FX/FXa. In one such embodiment the bispecific antibody is capable of specifically binding to FIX/FIXa and FX/FXa.

In one embodiment the antibody is a bispecific antibody capable of binding FIX/FIXa and FX/FXa, wherein the FIX/FIXa binding domain is derived from an antibody of Bin 1 and the FX/FXa binding domain is derived from an antibody of Bin A.

In one embodiment the antibody is a bispecific antibody binding FIX/FIXa and FX/FXa, wherein the FIX/FIXa binding domain is derived from an antibody of Bin 2 and the FX/FXa binding domain is derived from an antibody of Bin A.

In one embodiment the antibody is a bispecific antibody binding FIX/FIXa and FX/FXa, wherein the FIX/FIXa binding domain is derived from an antibody of Bin 2 and the FX/FXa binding domain is derived from an antibody of Bin B.

In one embodiment the antibody is a bispecific antibody binding FIX/FIXa and FX/FXa, wherein the FIX/FIXa binding domain is derived from an antibody of Bin 2 and the FX/FXa binding domain is derived from an antibody of Bin B.

In one embodiment the antibody is a bispecific antibody binding FIX/FIXa and FX/FXa, wherein the FIX/FIXa binding domain is derived from an antibody of Bin 1 and the FX/FXa binding domain is derived from an antibody of Bin C or D.

In one embodiment the antibody is a bispecific antibody binding FIX/FIXa and FX/FXa, wherein the binding domains are derived from the mAb pairs consisting of: mAb1-1371/mAb1-1307, mAb1-6705/mAb1-1307, mAb1-1371/mAb0-1886, mAb1-7441/mAb0-1886, mAb1-7447/mAb0-1886, mAb1-7481/mAb0-1886, mAb1-1371/mAb0-1998, mAb1-6716/mAb0-1998, mAb1-6723/mAb0-1998, mAb1-6730/mAb0-1998, mAb1-6731/mAb0-1998, mAb1-6737/mAb0-1998, mAb1-6754/mAb0-1998, mAb1-7378/mAb0-1998, mAb1-7441/mAb0-1998, mAb1-7447/mAb0-1998, mAb1-7481/mAb0-1998, mAb1-1371/mAb1-4707, mAb1-6705/mAb1-4707, mAb1-1371/mAb1-4071, mAb1-7441/mAb1-5788, mAb1-7447/mAb1-5788, mAb1-7481/mAb1-5788, mAb1-1371/mAb1-4857, mAb1-6716/mAb1-4857, mAb1-6723/mAb1-4857, mAb1-6730/mAb1-4857, mAb1-6731/mAb1-4857, mAb1-6737/mAb1-4857, mAb1-6754/mAb1-4857, mAb1-7378/mAb1-4857, mAb1-7441/mAb1-4857, mAb1-7447/mAb1-4857 or mAb1-7481/mAb1-4857.

In one embodiment a bispecific antibody of the invention comprises an antibody arm binding to FX and an antibody arm binding to FIX/FIXa. In one such embodiment the antibody arm binding to FX binds to an epitope comprising one or more residues in the activation peptide of FX and the antibody arm binding FIX/FIXa binds to an epitope comprising one or more residues in the FIX protease domain.

In one embodiment an antibody of the invention is a multispecific antibody, such as bi- or trispecific antibody.

In one embodiment an antibody of the invention is in IgG format such as full length IgG4.

In one embodiment an antibody of the invention is a chemical conjugate of two antibody fragments, such as a conjugate of two Fab fragments or scFv fragments, or combinations thereof.

In one embodiment an antibody of the invention is a human or humanised antibody.

In one embodiment the antibodies disclosed herein are intermediates for use in the manufacture of a bispecific antibody.

In one embodiment the invention includes antibodies competing for binding to FIX/FIXa with the antibodies disclosed herein.

An antibody of the current invention can be used to treat a subject with a coagulopathy and in particular haemophilia A. Thus, the invention also relates to the use of a monoclonal antibody, that is capable of binding the protease domain of FIX/FIXa, for the treatment of a subject in need thereof; as well as use of said antibody for the manufacture of a medicament for the treatment of a subject in need thereof. Furthermore, the invention includes a method of treating a subject in need thereof with a monoclonal antibody that is capable of binding to the protease domain of FIX/FIXa.

In one embodiment an antibody of the invention is capable of binding FIXa with a higher affinity than that with which it binds FIX.

In one embodiment an antibody of the invention is capable of increasing the enzymatic activity of FIXa towards FX.

In one such embodiment an antibody of the invention is capable of increasing the enzymatic activity of FIXa towards FX as measured in a FXa generation assay using monovalent one-armed antibodies as described herein.

In one embodiment an antibody of the invention is capable of increasing the enzymatic activity of FIXa towards FX as measured in a FXa generation assay using bivalent antibodies as described herein.

In one embodiment an antibody of the invention is not the anti-FIX antibody CLB-FIX 13 as described in Rohlena et al. (2003) J. Biol. Chem. 278(11):9394-9401. In one embodiment an antibody of the invention is not the anti-FIX antibody HIX-1 (IgG1 murine) (Merck KGaA, SigmaAldrich). In one embodiment an antibody of the invention is not the anti-FIX antibody AHIX-5041 (IgG1) (Haematologic Technologies, Inc.).

In one embodiment an antibody of the invention has reduced immunogenicity as compared to procoagulant antibodies of the art.

In one embodiment a bispecific antibody or antigen-binding fragment thereof comprises a first antigen-binding site recognizing FIX (SEQ ID NO:1) or the activated form thereof (FIXa), and a second antigen-binding site recognizing FX (SEQ ID NO:2) or the activated form thereof (FXa) wherein a) the first antigen-binding site comprises the following CDR sequences:

$V_H$-CDR1: DYAMH $V_H$-CDR2: GISWRGDIIGYVDSVKG $V_H$-CDR3: SYGSGSFYNAFDS $V_L$-CDR1: RASQSISSWLA $V_L$-CDR2: KASRLDR $V_L$-CDR3: LEYSSYIRT and
b) the second antigen-binding site comprises the following CDR sequences:

$V_H$-CDR1: TSWIV $V_H$-CDR2: MIDPSDSFTSYSPSFQG

-continued

```
V_H-CDR3: LHYYHSEEFDV
V_L-CDR1: RASQSVSSSYLA
V_L-CDR2: GASSRAR
V_L-CDR3: QQFGSSRLFT
```

In one embodiment a bispecific antibody or antigen-binding fragment thereof comprises a first antigen-binding site recognizing FIX (SEQ ID NO:1) or the activated form thereof (FIXa), and a second antigen-binding site recognizing FX (SEQ ID NO:2) or the activated form thereof (FXa) wherein
  a) the first antigen-binding site comprises the following CDR sequences:

```
V_H-CDR1: DYAMH
V_H-CDR2: GISWRGDIIGYVDSVKG
V_H-CDR3: SYGSGSFYNAFDS
V_L-CDR1: RASQSISSWLA
V_L-CDR2: KASRLDR
V_L-CDR3: LEYSSYIRT
``` and
b) the second antigen-binding site comprises the following CDR sequences:

```
V_H-CDR1: TSWIV
V_H-CDR2: MIDPSDSFTSYSPSFQG
V_H-CDR3: LHYYHSEEFDV
V_L-CDR1: RASQSVSSSYLA
V_L-CDR2: GASSRTR
V_L-CDR3: QQFGSSRLFT
```

The invention is further described by the following embodiments:
1. An antibody or antigen-binding fragment thereof capable of binding to Factor IX (FIX) according to SEQ ID NO:1 or the activated form hereof (FIXa).
2. The antibody or antigen-binding fragment thereof according to embodiment 1, wherein the antibody or antigen-binding fragment thereof is part of "Bin1".
3. The antibody or antigen-binding fragment thereof according to embodiment 1, wherein the antibody or antigen-binding fragment thereof competes with a reference antibody wherein the reference antibody comprises
    a. a heavy chain variable domain identified by SEQ ID NO:15 and a light chain variable domain identified by SEQ ID NO:16 or
    b. a heavy chain variable domain identified by SEQ ID NO:19 and a light chain variable domain identified by SEQ ID NO:20.
4. The antibody according to the previous embodiment, wherein the reference antibody is a Fab.
5. The antibody or antigen-binding fragment thereof according to any of the previous embodiments, wherein the antibody or antigen-binding fragment thereof comprises
    a. a heavy chain variable domain at least 90% identical to the sequence identified by SEQ ID NO:15 and a light chain variable domain at least 90% identical to the sequence identified by SEQ ID NO:16,
    b. a heavy chain variable domain at least 90% identical to the sequence identified by SEQ ID NO:19 and a light chain variable domain at least 90% identical to the sequence identified by SEQ ID NO:20,
    c. a heavy chain variable domain at least 90% identical to the sequence identified by SEQ ID NO:69 and a light chain variable domain at least 90% identical to the sequence identified by SEQ ID NO:70,
    d. a heavy chain variable domain at least 90% identical to the sequence identified by SEQ ID NO:71 and a light chain variable domain at least 90% identical to the sequence identified by SEQ ID NO:72,
    e. a heavy chain variable domain at least 90% identical to the sequence identified by SEQ ID NO:73 and a light chain variable domain at least 90% identical to the sequence identified by SEQ ID NO:74,
    f. a heavy chain variable domain at least 90% identical to the sequence identified by SEQ ID NO:83 and a light chain variable domain at least 90% identical to the sequence identified by SEQ ID NO:84,
    g. a heavy chain variable domain at least 90% identical to the sequence identified by SEQ ID NO:81 and a light chain variable domain at least 90% identical to the sequence identified by SEQ ID NO:82,
    h. a heavy chain variable domain at least 90% identical to the sequence identified by SEQ ID NO:75 and a light chain variable domain at least 90% identical to the sequence identified by SEQ ID NO:76,
    i. a heavy chain variable domain at least 90% identical to the sequence identified by SEQ ID NO:77 and a light chain variable domain at least 90% identical to the sequence identified by SEQ ID NO:78, or
    j. heavy chain variable domain at least 90% identical to the sequence identified by SEQ ID NO:177 and a light chain variable domain at least 90% identical to the sequence identified by SEQ ID NO:178.
6. The antibody or antigen-binding fragment thereof according to embodiment 5, wherein in the heavy chain variable domain is at least 92, 94, 96 or 98% identical to the identified SEQ IDs.
7. The antibody or antigen-binding fragment thereof according to embodiment 5, wherein in the light chain variable domain is at least 92, 94, 96 or 98% identical to the identified SEQ IDs.
8. The antibody or antigen-binding fragment thereof according to embodiment 6 and 7, wherein both the heavy chain variable domain and the light chain variable domain are at least 92, 94, 96 or 98% identical to the identified SEQ IDs.
9. The antibody or antigen-binding fragment thereof according to any of the previous embodiments, wherein the antibody or antigen-binding fragment thereof comprises
    a.
        i. three heavy chain CDR sequences with at most 10 amino acid changes compared to the CDR sequences of the heavy chain variable domain identified by SEQ ID NO:15 and
        ii. three light chain CDR sequences with at most 10 amino acid changes compared to the CDR sequences of the light chain variable domain identified by SEQ ID NO:16, b.
- i. three heavy chain CDR sequences with at most 10 amino acid changes compared to the CDR sequences of the heavy chain variable domain identified by SEQ ID NO:19 and
- ii. three light chain CDR sequences with at most 10 amino acid changes compared to the CDR sequences of the light chain variable domain identified by SEQ ID NO:20 c.
- i. three heavy chain CDR sequences with at most 10 amino acid changes compared to the CDR sequences of the heavy chain variable domain identified by SEQ ID NO:69 and
- ii. three light chain CDR sequences with at most 10 amino acid changes compared to the CDR sequences of the light chain variable domain identified by SEQ ID NO:70, d.
- i. three heavy chain CDR sequences with at most 10 amino acid changes compared to the CDR sequences of the heavy chain variable domain identified by SEQ ID NO:71 and
- ii. three light chain CDR sequences with at most 10 amino acid changes compared to the CDR sequences of the light chain variable domain identified by SEQ ID NO:72, e.
- i. three heavy chain CDR sequences with at most 10 amino acid changes compared to the CDR sequences of the heavy chain variable domain identified by SEQ ID NO:73 and
- ii. three light chain CDR sequences with at most 10 amino acid changes compared to the CDR sequences of the light chain variable domain identified by SEQ ID NO:74, f.
- i. three heavy chain CDR sequences with at most 10 amino acid changes compared to the CDR sequences of the heavy chain variable domain identified by SEQ ID NO:83 and
- ii. three light chain CDR sequences with at most 10 amino acid changes compared to the CDR sequences of the light chain variable domain identified by SEQ ID NO:84, g.
- i. three heavy chain CDR sequences with at most 10 amino acid changes compared to the CDR sequences of the heavy chain variable domain identified by SEQ ID NO:81 and
- ii. three light chain CDR sequences with at most 10 amino acid changes compared to the CDR sequences of the light chain variable domain identified by SEQ ID NO:82, h.
- i. three heavy chain CDR sequences with at most 10 amino acid changes compared to the CDR sequences of the heavy chain variable domain identified by SEQ ID NO:75 and
- ii. three light chain CDR sequences with at most 10 amino acid changes compared to the CDR sequences of the light chain variable domain identified by SEQ ID NO:76 or i.
- i. three heavy chain CDR sequences with at most 10 amino acid changes compared to the CDR sequences of the heavy chain variable domain identified by SEQ ID NO:77 and
- ii. three light chain CDR sequences with at most 10 amino acid changes compared to the CDR sequences of the light chain variable domain identified by SEQ ID NO:78 or j.
- i. three heavy chain CDR sequences with at most 10 amino acid changes compared to the CDR sequences of the heavy chain variable domain identified by SEQ ID NO:177 and
- ii. three light chain CDR sequences with at most 10 amino acid changes compared to the CDR sequences of the light chain variable domain identified by SEQ ID NO:178.

10. The antibody or antigen-binding fragment thereof according to embodiment 9, wherein the three heavy chain CDR sequences have at most 9, such as 8, such as 7 or such as 6 amino acid changes compared to the CDRs of the identified SEQ IDs.

11. The antibody or antigen-binding fragment thereof according to embodiment 9, wherein the three heavy chain CDR sequences have at most 5, such as 4, such as 3, such as 2 or at most 1 amino acid changes compared to the CDRs of the identified SEQ IDs.

12. The antibody or antigen-binding fragment thereof according to embodiment 9, wherein the three light chain CDR sequences have at most 9, such as 8, such as 7 or such as 6 amino acid changes compared to the CDRs of the identified SEQ IDs.

13. The antibody or antigen-binding fragment thereof according to embodiment 9, wherein the three light chain CDR sequences have at most 5, such as 4, such as 3, such as 2 or at most 1 amino acid changes compared to the CDRs of the identified SEQ IDs.

14. The antibody or antigen-binding fragment thereof according to any of the previous embodiments, wherein the antibody or antigen-binding fragment thereof comprises
- a. the CDR sequences of the heavy chain variable domain identified by SEQ ID NO:15 and the CDR sequences of the light chain variable domain identified by SEQ ID NO:16, or
- b. the CDR sequences of the heavy chain variable domain identified by SEQ ID NO:19 and the CDR sequences of the light chain variable domain identified by SEQ ID NO:20, or
- c. the CDR sequences of the heavy chain variable domain identified by SEQ ID NO:3 and the CDR sequences of the light chain variable domain identified by SEQ ID NO:4, or
- d. the CDR sequences of the heavy chain variable domain identified by SEQ ID NO:109 and the CDR sequences of the light chain variable domain identified by SEQ ID NO:110, or
- e. the CDR sequences of the heavy chain variable domain identified by SEQ ID NO:153 and the CDR sequences of the light chain variable domain identified by SEQ ID NO:154, or
- f. the CDR sequences of the heavy chain variable domain identified by SEQ ID NO:171 and the CDR sequences of the light chain variable domain identified by SEQ ID NO:172, or
- g. the CDR sequences of the heavy chain variable domain identified by SEQ ID NO:177 and the CDR sequences of the light chain variable domain identified by SEQ ID NO:178, or h. the CDR sequences of the heavy chain variable domain identified by SEQ ID NO:187 and the CDR sequences of the light chain variable domain identified by SEQ ID NO:188.

15. The antibody or antigen-binding fragment thereof according to any of the previous embodiments, wherein the antibody or antigen-binding fragment thereof comprises
   a. a heavy chain variable domain identified by SEQ ID NO:15 and a light chain variable domain identified by SEQ ID NO:16, or
   b. a heavy chain variable domain identified by SEQ ID NO:19 and a light chain variable domain identified by SEQ ID NO:20, or
   c. a heavy chain variable domain identified by SEQ ID NO:3 and a light chain variable domain identified by SEQ ID NO:4, or
   d. a heavy chain variable domain identified by SEQ ID NO:109 and a light chain variable domain identified by SEQ ID NO:110, or
   e. a heavy chain variable domain identified by SEQ ID NO:153 and a light chain variable domain identified by SEQ ID NO:154, or
   f. a heavy chain variable domain identified by SEQ ID NO:171 and a light chain variable domain identified by SEQ ID NO:172, or
   g. a heavy chain variable domain identified by SEQ ID NO:177 and a light chain variable domain identified by SEQ ID NO:178, or
   h. a heavy chain variable domain identified by SEQ ID NO:187 and a light chain variable domain identified by SEQ ID NO:188.

16. The antibody or antigen-binding fragment thereof according to any of the previous embodiments, wherein the antibody or antigen-binding fragment thereof is capable of binding an epitope comprising one or more of the amino acid residues L337, R338, S339, T340, K341 and T343 of SEQ ID NO:1.

17. The antibody or antigen-binding fragment thereof according to any of the previous embodiments, wherein the antibody or antigen-binding fragment thereof is capable of binding an epitope comprising amino acid residue R338 of SEQ ID NO:1.

18. The antibody or antigen-binding fragment thereof according to any of the previous embodiments, wherein the antibody or antigen-binding fragment thereof is capable of binding an epitope comprising amino acid residues R338 and K341 of SEQ ID NO:1.

19. The antibody or antigen-binding fragment thereof according to any of the previous embodiments, wherein the antibody or antigen-binding fragment thereof is capable of binding an epitope comprising two or three of the amino acid residues L337, R338, S339, T340, K341 and T343 of SEQ ID NO:1.

20. The antibody or antigen-binding fragment thereof according to any of the previous embodiments, wherein the antibody or antigen-binding fragment thereof is capable of binding an epitope comprising four or five of the amino acid residues L337, R338, S339, T340, K341 and T343 of SEQ ID NO:1.

21. The antibody or antigen-binding fragment thereof according to any of the previous embodiments, wherein the antibody or antigen-binding fragment thereof is capable of binding an epitope comprising
   a. R338, S339, T340, K341 and T343,
   b. L337, S339, T340, K341 and T343,
   c. L337, R338, T340, K341 and T343,
   d. L337, R338, S339, K341 and T343,
   e. L337, R338, S339, T340 and T343 or
   f. L337, R338, S339, T340 and K341
   of SEQ ID NO:1.

22. The antibody or antigen-binding fragment thereof according to any of the previous embodiments, wherein the antibody or antigen-binding fragment thereof is capable of binding an epitope comprising amino acid residues L337, R338, S339, T340, K341 and T343 of SEQ ID NO:1.

23. The antibody or antigen-binding fragment thereof according to any of the previous embodiments, wherein the antibody or antigen-binding fragment thereof is capable of binding an epitope comprising one or more of the amino acid residues K301, D332, R333, A334, T335, R338, and N346 of SEQ ID NO:1.

24. The antibody or antigen-binding fragment thereof according to any of the previous embodiments, wherein the antibody or antigen-binding fragment thereof is capable of binding an epitope comprising amino acid residues L337, R338, S339, T340, K341 and T343 of SEQ ID NO:1.

25. The antibody or antigen-binding fragment thereof according to any of the previous embodiments, wherein the antibody or antigen-binding fragment thereof is capable of binding an epitope comprising two or three of the amino acid residues K301, D332, R333, A334, T335, R338, and N346 of SEQ ID NO:1.

26. The antibody or antigen-binding fragment thereof according to any of the previous embodiments, wherein the antibody or antigen-binding fragment thereof is capable of binding an epitope comprising four or five of the amino acid residues K301, D332, R333, A334, T335, R338, and N346 of SEQ ID NO:1.

27. The antibody or antigen-binding fragment thereof according to any of the previous embodiments, wherein the antibody or antigen-binding fragment thereof is capable of binding an epitope comprising five or six of the amino acid residues K301, D332, R333, A334, T335, R338, and N346 of SEQ ID NO:1.

28. The antibody or antigen-binding fragment thereof according to any of the previous embodiments, wherein the antibody or antigen-binding fragment thereof is capable of binding an epitope comprising
   a. D332, R333, A334, T335, R338 and N346
   b. K301, R333, A334, T335, R338 and N346
   c. K301, D332, A334, T335, R338 and N346
   d. K301, D332, R333, T335, R338 and N346
   e. K301, D332, R333, A334, R338 and N346
   f. K301, D332, R333, A334, T335 and N346 or
   g. K301, D332, R333, A334, T335 and R338
   of SEQ ID NO:1.

29. The antibody or antigen-binding fragment thereof according to any of the previous embodiments, wherein the antibody or antigen-binding fragment thereof is capable of binding an epitope comprising the amino acid residues D332, R333, L337 and R338 of SEQ ID NO:1.

30. The antibody or antigen-binding fragment thereof according to any of the previous embodiments, wherein the antibody or antigen-binding fragment thereof is capable of binding an epitope comprising the amino acid residues K301, D332, R333, A334, T335, R338, and N346 of SEQ ID NO:1.

31. The antibody or antigen-binding fragment thereof according to embodiment 1, wherein the antibody or antigen-binding fragment thereof belongs to "Bin2".

32. The antibody or antigen-binding fragment thereof according to embodiment 1, wherein the antibody or antigen-binding fragment thereof competes with a reference antibody wherein the reference antibody comprises a heavy chain variable domain identified by the sequence of SEQ ID NO:17 and a light chain variable domain identified by the sequence of SEQ ID NO:18.

33. The antibody according to the previous embodiment, wherein the reference antibody is a Fab.

34. The antibody or antigen-binding fragment thereof according to any of the previous embodiments, wherein the antibody or antigen-binding fragment thereof comprises
   a. a heavy chain variable domain at least 90% identical to the sequence identified by SEQ ID NO:17 and a light chain variable domain at least 90% identical to the sequence identified by SEQ ID NO:18.
   b. a heavy chain variable domain at least 90% identical to the sequence identified by SEQ ID NO:85 and a light chain variable domain at least 90% identical to the sequence identified by SEQ ID NO:86 or
   c. a heavy chain variable domain at least 90% identical to the sequence identified by SEQ ID NO:79 and a light chain variable domain at least 90% identical to the sequence identified by SEQ ID NO:80.

35. The antibody or antigen-binding fragment thereof according to embodiment 34, wherein in the heavy chain variable domain is at least 92, 94, 96 or 98% identical to the identified SEQ IDs.

36. The antibody or antigen-binding fragment thereof according to embodiment 34, wherein in the light chain variable domain is at least 92, 94, 96 or 98% identical to the identified SEQ IDs.

37. The antibody or antigen-binding fragment thereof according to embodiment 35 and 36, wherein both the heavy chain variable domain and the light chain variable domain are at least 92, 94, 96 or 98% identical to the identified SEQ IDs.

38. The antibody or antigen-binding fragment thereof according to any of the previous embodiments, wherein the antibody or antigen-binding fragment thereof comprises
   a.
      i. three heavy chain CDR sequences with at most 10 amino acid changes compared to the CDR sequences of the heavy chain variable domain identified by SEQ ID NO:17 and
      ii. three light chain CDR sequences with at most 10 amino acid changes compared to the CDR sequences of the light chain variable domain identified by SEQ ID NO:18,
   b.
      i. three heavy chain CDR sequences with at most 10 amino acid changes compared to the CDR sequences of the heavy chain variable domain identified by SEQ ID NO:85 and
      ii. three light chain CDR sequences with at most 10 amino acid changes compared to the CDR sequences of the light chain variable domain identified by SEQ ID NO:86 or
   c.
      i. three heavy chain CDR sequences with at most 10 amino acid changes compared to the CDR sequences of the heavy chain variable domain identified by SEQ ID NO:79 and
      ii. three light chain CDR sequences with at most 10 amino acid changes compared to the CDR sequences of the light chain variable domain identified by SEQ ID NO:80.

39. The antibody or antigen-binding fragment thereof according to embodiment 38, wherein the three heavy chain CDR sequences have at most 9, such as 8, such as 7 or such as 6 amino acid changes compared to the CDRs of the identified SEQ IDs.

40. The antibody or antigen-binding fragment thereof according to embodiment 38, wherein the three heavy chain CDR sequences have at most 5, such as 4, such as 3, such as 2 or at most 1 amino acid changes compared to the CDRs of the identified SEQ IDs.

41. The antibody or antigen-binding fragment thereof according to embodiment 38, wherein the three light chain CDR sequences have at most 9, such as 8, such as 7 or such as 6 amino acid changes compared to the CDRs of the identified SEQ IDs.

42. The antibody or antigen-binding fragment thereof according to embodiment 38, wherein the three light chain CDR sequences have at most 5, such as 4, such as 3, such as 2 or at most 1 amino acid changes compared to the CDRs of the identified SEQ IDs.

43. The antibody or antigen-binding fragment thereof according to any of the previous embodiments, wherein the antibody or antigen-binding fragment thereof comprises
   a. the CDR sequences of the heavy chain variable domain identified by SEQ ID NO:17 and
   the CDR sequences of the light chain variable domain identified by SEQ ID NO:18.

44. The antibody or antigen-binding fragment thereof according to any of the previous embodiments, wherein the antibody or antigen-binding fragment thereof comprises
   a. a heavy chain variable domain identified by SEQ ID NO:17 and a light chain variable domain identified by SEQ ID NO:18.

45. The antibody or antigen-binding fragment thereof according to any of the previous embodiments, wherein the antibody or antigen-binding fragment thereof is capable of binding an epitope comprising one or more of the amino acid residues H256, H257, N258, K293, R403, Y404, N406, W407, E410, and K411 of SEQ ID NO:1.

46. The antibody or antigen-binding fragment thereof according to any of the previous embodiments, wherein the antibody or antigen-binding fragment thereof is capable of binding an epitope comprising the amino acid residues H256, H257, N258, K293, R403, Y404, N406, W407, E410, and K411 SEQ ID NO:1.

47. The antibody or antigen-binding fragment thereof according to any of the previous embodiments, wherein the antibody or antigen-binding fragment thereof is capable of binding an epitope comprising two, three or four of the amino acid residues H256, H257, N258, K293, R403, Y404, N406, W407, E410, and K411 of SEQ ID NO:1.

48. The antibody or antigen-binding fragment thereof according to any of the previous embodiments, wherein the antibody or antigen-binding fragment thereof is capable of binding an epitope comprising five, six or seven of the amino acid residues H256, H257, N258, K293, R403, Y404, N406, W407, E410, and K411 of SEQ ID NO:1.

49. The antibody or antigen-binding fragment thereof according to any of the previous embodiments, wherein the antibody or antigen-binding fragment thereof is capable of binding an epitope comprising eight, nine or ten of the amino acid residues H256, H257, N258, K293, R403, Y404, N406, W407, E410, and K411 of SEQ ID NO:1.

50. The antibody or antigen-binding fragment thereof according to any of the previous embodiments, wherein the antibody or antigen-binding fragment thereof is capable of binding an epitope comprising the amino acid residues
    a. H257, N258, K293, R403, Y404, N406, W407, E410 and K411,
    b. H256, N258, K293, R403, Y404, N406, W407, E410 and K411,
    c. H256, H257, K293, R403, Y404, N406, W407, E410 and K411,
    d. H256, H257, N258, R403, Y404, N406, W407, E410 and K411,
    e. H256, H257, N258, K293, Y404, N406, W407, E410 and K411,
    f. H256, H257, N258, K293, R403, N406, W407, E410 and K411,
    g. H256, H257, N258, K293, R403, Y404, W407, E410 and K411,
    h. H256, H257, N258, K293, R403, Y404, N406, E410 and K411,
    i. H256, H257, N258, K293, R403, Y404, N406, W407 and K411 or
    j. H256, H257, N258, K293, R403, Y404, N406, W407 and E410
    of SEQ ID NO:1.

51. The antibody or antigen-binding fragment thereof according to any of the previous embodiments, wherein the antibody or antigen-binding fragment thereof is capable of binding an epitope comprising the amino acid residues H256, H257, N258, K293, R403, Y404, N406, W407, E410, and K411 of SEQ ID NO:1.

52. The antibody or antigen-binding fragment thereof according to any of the previous embodiments, wherein the antibody or antigen-binding fragment thereof is capable of binding an epitope comprising the amino acid residues H257, K293 and N406 of SEQ ID NO:1.

53. The antibody or antigen-binding fragment thereof according to any one of the previous embodiments wherein the antibody is a procoagulant antibody.

54. The antibody or antigen-binding fragment thereof according to any one of the previous embodiments wherein the antibody or antigen-binding fragment thereof is capable of increasing the procoagulant activity of FIXa.

55. The antibody or antigen-binding fragment thereof according to any one of the previous embodiments wherein the antibody is capable of increasing the enzymatic activity of FIXa towards FX.

56. The antibody or antigen-binding fragment thereof according to any one of the previous embodiments wherein the antibody is capable of functionally substituting for FVIII and/or FVIIIa.

57. An antibody or antigen-binding fragment thereof capable of binding to FX (SEQ ID NO:2) or the activated form thereof (FXa).

58. The antibody or antigen-binding fragment thereof according to embodiment 57, wherein the antibody or antigen-binding fragment thereof is part of "Bin A".

59. The antibody or antigen-binding fragment thereof according to embodiment 57, wherein the antibody or antigen-binding fragment thereof competes with a reference antibody wherein the reference antibody comprises a heavy chain variable domain identified by SEQ ID NO:65 and a light chain variable domain identified by SEQ ID NO:66.

60. The antibody according to the previous embodiment, wherein the reference antibody is a Fab.

61. The antibody or antigen-binding fragment thereof according to any of the previous embodiments, wherein the antibody or antigen-binding fragment thereof is capable of binding an epitope comprising one or more of the amino acid residues H101, E103, R113, T116, L117, A118, T127, S227, E228, F229, Y230, E266, R287, L303, P304, E305, L419, K420, D423, R424, M426, K427 and T428 of FX/FXa.

62. The antibody or antigen-binding fragment thereof according to any of the previous embodiments, wherein the antibody or antigen-binding fragment thereof is capable of binding an epitope comprising the amino acid residues H101, E103, R113, T116, L117, A118, T127, S227, E228, F229, Y230, E266, R287, P304, L303, P304, E305, L419, K420, D423, R424, M426, K427 and T428 of FX/FXa.

63. The antibody or antigen-binding fragment thereof according to any of the previous embodiments, wherein the antibody or antigen-binding fragment thereof is capable of binding an epitope comprising one or more of the amino acid residues R113, Y230, K420 D423, R424 and K427 of FX/FXa.

64. The antibody or antigen-binding fragment thereof according to any of the previous embodiments, wherein the antibody or antigen-binding fragment thereof is capable of binding an epitope comprising the amino acid residues R113, Y230, K420, D423, R424 and K427 of FX/FXa.

65. The antibody or antigen-binding fragment thereof according to any of the previous embodiments, wherein the antibody or antigen-binding fragment thereof comprises a heavy chain variable domain at least 90% identical to the sequence identified by SEQ ID NO:65 and a light chain variable domain at least 90% identical to the sequence identified by SEQ ID NO:66.

66. The antibody or antigen-binding fragment thereof according to embodiment 65, wherein in the heavy chain variable domain is at least 92, 94, 96 or 98% identical to the identified SEQ IDs.

67. The antibody or antigen-binding fragment thereof according to embodiment 65, wherein in the light chain variable domain is at least 92, 94, 96 or 98% identical to the identified SEQ IDs.

68. The antibody or antigen-binding fragment thereof according to embodiment 66 and 67, wherein both the heavy chain variable domain and the light chain variable domain are at least 92, 94, 96 or 98% identical to the identified SEQ IDs.

69. The antibody or antigen-binding fragment thereof according to any of the previous embodiments, wherein the antibody or antigen-binding fragment thereof comprises
    a. three heavy chain CDR sequences with at most 10 amino acid changes compared to the CDR sequences of the heavy chain variable domain identified by SEQ ID NO:65 and
    b. three light chain CDR sequences with at most 10 amino acid changes compared to the CDR sequences of the light chain variable domain identified by SEQ ID NO:66.

70. The antibody or antigen-binding fragment thereof according to embodiment 69, wherein the three heavy chain CDR sequences have at most 9, such as 8, such as 7 or such as 6 amino acid changes compared to the CDRs of the identified SEQ IDs.
71. The antibody or antigen-binding fragment thereof according to embodiment 69, wherein the three heavy chain CDR sequences have at most 5, such as 4, such as 3, such as 2 or at most 1 amino acid changes compared to the CDRs of the identified SEQ IDs.
72. The antibody or antigen-binding fragment thereof according to embodiment 69, wherein the three light chain CDR sequences have at most 9, such as 8, such as 7 or such as 6 amino acid changes compared to the CDRs of the identified SEQ IDs.
73. The antibody or antigen-binding fragment thereof according to embodiment 69, wherein the three light chain CDR sequences have at most 5, such as 4, such as 3, such as 2 or at most 1 amino acid changes compared to the CDRs of the identified SEQ IDs.
74. The antibody or antigen-binding fragment thereof according to any of the previous embodiments, wherein the antibody or antigen-binding fragment thereof comprises the CDR sequences of the heavy chain variable domain identified by SEQ ID NO:65 and the CDR sequences of the light chain variable domain identified by SEQ ID NO:66.
75. The antibody or antigen-binding fragment thereof according to any of the previous embodiments, wherein the antibody or antigen-binding fragment thereof comprises a heavy chain variable domain identified by SEQ ID NO:65 and a light chain variable domain identified by SEQ ID NO:66.
76. The antibody or antigen-binding fragment thereof according to embodiment 57, wherein the antibody or antigen-binding fragment thereof is part of "Bin B".
77. The antibody or antigen-binding fragment thereof according to embodiment 57, wherein the antibody or antigen-binding fragment thereof competes with a reference antibody wherein the reference antibody comprises a heavy chain variable domain identified by SEQ ID NO:67 and a light chain variable domain identified by SEQ ID NO:68.
78. The antibody or antigen-binding fragment thereof according to the previous embodiment, wherein the reference antibody is a Fab.
79. The antibody or antigen-binding fragment thereof according to any of the previous embodiments, wherein the antibody or antigen-binding fragment thereof comprises
  a. a heavy chain variable domain at least 90% identical to the sequence identified by SEQ ID NO:67 and a light chain variable domain at least 90% identical to the sequence identified by SEQ ID NO:68,
  b. a heavy chain variable domain at least 90% identical to the sequence identified by SEQ ID NO:23 and a light chain variable domain at least 90% identical to the sequence identified by SEQ ID NO:24,
  c. a heavy chain variable domain at least 90% identical to the sequence identified by SEQ ID NO:39 and a light chain variable domain at least 90% identical to the sequence identified by SEQ ID NO:40 or
  d. a heavy chain variable domain at least 90% identical to the sequence identified by SEQ ID NO:59 and a light chain variable domain at least 90% identical to the sequence identified by SEQ ID NO:60.
80. The antibody or antigen-binding fragment thereof according to embodiment 79, wherein in the heavy chain variable domain is at least 92, 94, 96 or 98% identical to the identified SEQ IDs.
81. The antibody or antigen-binding fragment thereof according to embodiment 79, wherein in the light chain variable domain is at least 92, 94, 96 or 98% identical to the identified SEQ IDs.
82. The antibody or antigen-binding fragment thereof according to embodiment 80 and 81, wherein both the heavy chain variable domain and the light chain variable domain are at least 92, 94, 96 or 98% identical to the identified SEQ IDs.
83. The antibody or antigen-binding fragment thereof according to any of the previous embodiments, wherein the antibody or antigen-binding fragment thereof comprises
  a.
    i. three heavy chain CDR sequences with at most 10 amino acid changes compared to the CDR sequences of the heavy chain variable domain identified by SEQ ID NO:67 and
    ii. three light chain CDR sequences with at most 10 amino acid changes compared to the CDR sequences of the light chain variable domain identified by SEQ ID NO:68,
  b.
    i. three heavy chain CDR sequences with at most 10 amino acid changes compared to the CDR sequences of the heavy chain variable domain identified by SEQ ID NO:23 and
    ii. three light chain CDR sequences with at most 10 amino acid changes compared to the CDR sequences of the light chain variable domain identified by SEQ ID NO:24,
  c.
    i. three heavy chain CDR sequences with at most 10 amino acid changes compared to the CDR sequences of the heavy chain variable domain identified by SEQ ID NO:39 and
    ii. three light chain CDR sequences with at most 10 amino acid changes compared to the CDR sequences of the light chain variable domain identified by SEQ ID NO:40 or
  d.
    i. three heavy chain CDR sequences with at most 10 amino acid changes compared to the CDR sequences of the heavy chain variable domain identified by SEQ ID NO:59 and
    ii. three light chain CDR sequences with at most 10 amino acid changes compared to the CDR sequences of the light chain variable domain identified by SEQ ID NO:60.
84. The antibody or antigen-binding fragment thereof according to embodiment 83, wherein the three heavy chain CDR sequences have at most 9, such as 8, such as 7 or such as 6 amino acid changes compared to the CDRs of the identified SEQ IDs.
85. The antibody or antigen-binding fragment thereof according to embodiment 83, wherein the three heavy chain CDR sequences have at most 5, such as 4, such as 3, such as 2 or at most 1 amino acid changes compared to the CDRs of the identified SEQ IDs.
86. The antibody or antigen-binding fragment thereof according to embodiment 83, wherein the three light chain CDR sequences have at most 9, such as 8, such as 7 or such as 6 amino acid changes compared to the CDRs of the identified SEQ IDs.

87. The antibody or antigen-binding fragment thereof according to embodiment 83, wherein the three light chain CDR sequences have at most 5, such as 4, such as 3, such as 2 or at most 1 amino acid changes compared to the CDRs of the identified SEQ IDs.

88. The antibody or antigen-binding fragment thereof according to any of the previous embodiments, wherein the antibody or antigen-binding fragment thereof comprises
    a. the CDR sequences of the heavy chain variable domain identified by SEQ ID NO:67 and the CDR sequences of the light chain variable domain identified by SEQ ID NO:68,
    b. the CDR sequences of the heavy chain variable domain identified by SEQ ID NO:23 and the CDR sequences of the light chain variable domain identified by SEQ ID NO:24,
    c. the CDR sequences of the heavy chain variable domain identified by SEQ ID NO:39 and the CDR sequences of the light chain variable domain identified by SEQ ID NO:40 or
    d. the CDR sequences of the heavy chain variable domain identified by SEQ ID NO:59 and the CDR sequences of the light chain variable domain identified by SEQ ID NO:60.

89. The antibody or antigen-binding fragment thereof according to any of the previous embodiments, wherein the antibody or antigen-binding fragment thereof comprises
    a. a heavy chain variable domain identified by SEQ ID NO:67 and a light chain variable domain identified by SEQ ID NO:68,
    b. a heavy chain variable domain identified by SEQ ID NO:23 and a light chain variable domain identified by SEQ ID NO:24,
    c. a heavy chain variable domain identified by SEQ ID NO:39 and a light chain variable domain identified by SEQ ID NO:40 or
    d. a heavy chain variable domain identified by SEQ ID NO:59 and a light chain variable domain identified by SEQ ID NO:60.

90. The antibody or antigen-binding fragment thereof according to embodiment 57, wherein the antibody or antigen-binding fragment thereof is part of "Bin C".

91. The antibody or antigen-binding fragment thereof according to embodiment 57, wherein the antibody or antigen-binding fragment thereof competes with a reference antibody wherein the reference antibody comprises a heavy chain variable domain identified by SEQ ID NO:21 and a light chain variable domain identified by SEQ ID NO:22.

92. The antibody or antigen-binding fragment thereof according to the previous embodiment, wherein the reference antibody is a Fab.

93. The antibody or antigen-binding fragment thereof according to any of the previous embodiments, wherein the antibody or antigen-binding fragment thereof comprises
    a. a heavy chain variable domain at least 90% identical to the sequence identified by SEQ ID NO:21 and a light chain variable domain at least 90% identical to the sequence identified by SEQ ID NO:22,
    b. a heavy chain variable domain at least 90% identical to the sequence identified by SEQ ID NO:25 and a light chain variable domain at least 90% identical to the sequence identified by SEQ ID NO:26.
    c. a heavy chain variable domain at least 90% identical to the sequence identified by SEQ ID NO:27 and a light chain variable domain at least 90% identical to the sequence identified by SEQ ID NO:28,
    d. a heavy chain variable domain at least 90% identical to the sequence identified by SEQ ID NO:29 and a light chain variable domain at least 90% identical to the sequence identified by SEQ ID NO:30,
    e. a heavy chain variable domain at least 90% identical to the sequence identified by SEQ ID NO:31 and a light chain variable domain at least 90% identical to the sequence identified by SEQ ID NO:32,
    f. a heavy chain variable domain at least 90% identical to the sequence identified by SEQ ID NO:33 and a light chain variable domain at least 90% identical to the sequence identified by SEQ ID NO:34.
    g. a heavy chain variable domain at least 90% identical to the sequence identified by SEQ ID NO:35 and a light chain variable domain at least 90% identical to the sequence identified by SEQ ID NO:36,
    h. a heavy chain variable domain at least 90% identical to the sequence identified by SEQ ID NO:37 and a light chain variable domain at least 90% identical to the sequence identified by SEQ ID NO:38,
    i. a heavy chain variable domain at least 90% identical to the sequence identified by SEQ ID NO:39 and a light chain variable domain at least 90% identical to the sequence identified by SEQ ID NO:40,
    j. a heavy chain variable domain at least 90% identical to the sequence identified by SEQ ID NO:41 and a light chain variable domain at least 90% identical to the sequence identified by SEQ ID NO:42,
    k. a heavy chain variable domain at least 90% identical to the sequence identified by SEQ ID NO:43 and a light chain variable domain at least 90% identical to the sequence identified by SEQ ID NO:44,
    l. a heavy chain variable domain at least 90% identical to the sequence a heavy chain variable domain at least 90% identical to the sequence identified by SEQ ID NO:51 and a light chain variable domain at least 90% identical to the sequence identified by SEQ ID NO:52,
    m. a heavy chain variable domain at least 90% identical to the sequence identified by SEQ ID NO:53 and a light chain variable domain at least 90% identical to the sequence identified by SEQ ID NO:54,
    n. a heavy chain variable domain at least 90% identical to the sequence identified by SEQ ID NO:55 and a light chain variable domain at least 90% identical to the sequence identified by SEQ ID NO:56,
    o. a heavy chain variable domain at least 90% identical to the sequence identified by SEQ ID NO:57 and a light chain variable domain at least 90% identical to the sequence identified by SEQ ID NO:58,
    p. a heavy chain variable domain at least 90% identical to the sequence identified by SEQ ID NO:59 and a light chain variable domain at least 90% identical to the sequence identified by SEQ ID NO:60,
    q. a heavy chain variable domain at least 90% identical to the sequence identified by SEQ ID NO:61 and a light chain variable domain at least 90% identical to the sequence identified by SEQ ID NO:62 or
    r. a heavy chain variable domain at least 90% identical to the sequence identified by SEQ ID NO:63 and a light chain variable domain at least 90% identical to the sequence identified by SEQ ID NO:64.

94. The antibody or antigen-binding fragment thereof according to embodiment 93, wherein in the heavy chain variable domain is at least 92, 94, 96 or 98% identical to the identified SEQ IDs.
95. The antibody or antigen-binding fragment thereof according to embodiment 93, wherein in the light chain variable domain is at least 92, 94, 96 or 98% identical to the identified SEQ IDs.
96. The antibody or antigen-binding fragment thereof according to embodiment 94 and 95, wherein both the heavy chain variable domain and the light chain variable domain are at least 92, 94, 96 or 98% identical to the identified SEQ IDs.
97. The antibody or antigen-binding fragment thereof according to any of the previous embodiments, wherein the antibody or antigen-binding fragment thereof comprises
  a.
    i. three heavy chain CDR sequences with at most 10 amino acid changes compared to the CDR sequences of the heavy chain variable domain identified by SEQ ID NO:21 and
    ii. three light chain CDR sequences with at most 10 amino acid changes compared to the CDR sequences of the light chain variable domain identified by SEQ ID NO:22,
  b.
    i. three heavy chain CDR sequences with at most 10 amino acid changes compared to the CDR sequences of the heavy chain variable domain identified by SEQ ID NO:25 and
    ii. three light chain CDR sequences with at most 10 amino acid changes compared to the CDR sequences of the light chain variable domain identified by SEQ ID NO:26,
  c.
    i. three heavy chain CDR sequences with at most 10 amino acid changes compared to the CDR sequences of the heavy chain variable domain identified by SEQ ID NO:27 and
    ii. three light chain CDR sequences with at most 10 amino acid changes compared to the CDR sequences of the light chain variable domain identified by SEQ ID NO:28 or
  d.
    i. three heavy chain CDR sequences with at most 10 amino acid changes compared to the CDR sequences of the heavy chain variable domain identified by SEQ ID NO:29 and
    ii. three light chain CDR sequences with at most 10 amino acid changes compared to the CDR sequences of the light chain variable domain identified by SEQ ID NO:30,
  e.
    i. three heavy chain CDR sequences with at most 10 amino acid changes compared to the CDR sequences of the heavy chain variable domain identified by SEQ ID NO:31 and
    ii. three light chain CDR sequences with at most 10 amino acid changes compared to the CDR sequences of the light chain variable domain identified by SEQ ID NO:32,
  f.
    i. three heavy chain CDR sequences with at most 10 amino acid changes compared to the CDR sequences of the heavy chain variable domain identified by SEQ ID NO:33 and
    ii. three light chain CDR sequences with at most 10 amino acid changes compared to the CDR sequences of the light chain variable domain identified by SEQ ID NO:34,
  g.
    i. three heavy chain CDR sequences with at most 10 amino acid changes compared to the CDR sequences of the heavy chain variable domain identified by SEQ ID NO:35 and
    ii. three light chain CDR sequences with at most 10 amino acid changes compared to the CDR sequences of the light chain variable domain identified by SEQ ID NO:36 or
  h.
    i. three heavy chain CDR sequences with at most 10 amino acid changes compared to the CDR sequences of the heavy chain variable domain identified by SEQ ID NO:37 and
    ii. three light chain CDR sequences with at most 10 amino acid changes compared to the CDR sequences of the light chain variable domain identified by SEQ ID NO:38
  i.
    i. three heavy chain CDR sequences with at most 10 amino acid changes compared to the CDR sequences of the heavy chain variable domain identified by SEQ ID NO:39 and
    ii. three light chain CDR sequences with at most 10 amino acid changes compared to the CDR sequences of the light chain variable domain identified by SEQ ID NO:40,
  j.
    i. three heavy chain CDR sequences with at most 10 amino acid changes compared to the CDR sequences of the heavy chain variable domain identified by SEQ ID NO:41 and
    ii. three light chain CDR sequences with at most 10 amino acid changes compared to the CDR sequences of the light chain variable domain identified by SEQ ID NO:42,
  k.
    i. three heavy chain CDR sequences with at most 10 amino acid changes compared to the CDR sequences of the heavy chain variable domain identified by SEQ ID NO:43 and
    ii. three light chain CDR sequences with at most 10 amino acid changes compared to the CDR sequences of the light chain variable domain identified by SEQ ID NO:44 or
  l.
  m.
    i. three heavy chain CDR sequences with at most 10 amino acid changes compared to the CDR sequences of the heavy chain variable domain identified by SEQ ID NO:51 and
    ii. three light chain CDR sequences with at most 10 amino acid changes compared to the CDR sequences of the light chain variable domain identified by SEQ ID NO:52 or
  n.
    i. three heavy chain CDR sequences with at most 10 amino acid changes compared to the CDR sequences of the heavy chain variable domain identified by SEQ ID NO:53 and three light chain CDR sequences with at most 10 amino acid changes compared to the CDR sequences of the light chain variable domain identified by SEQ ID NO:54 o.
i. three heavy chain CDR sequences with at most 10 amino acid changes compared to the CDR sequences of the heavy chain variable domain identified by SEQ ID NO:55 and
ii. three light chain CDR sequences with at most 10 amino acid changes compared to the CDR sequences of the light chain variable domain identified by SEQ ID NO:56 p.
i. three heavy chain CDR sequences with at most 10 amino acid changes compared to the CDR sequences of the heavy chain variable domain identified by SEQ ID NO:57 and
ii. three light chain CDR sequences with at most 10 amino acid changes compared to the CDR sequences of the light chain variable domain identified by SEQ ID NO:58, q.
i. three heavy chain CDR sequences with at most 10 amino acid changes compared to the CDR sequences of the heavy chain variable domain identified by SEQ ID NO:59 and
ii. three light chain CDR sequences with at most 10 amino acid changes compared to the CDR sequences of the light chain variable domain identified by SEQ ID NO:60, r.
i. three heavy chain CDR sequences with at most 10 amino acid changes compared to the CDR sequences of the heavy chain variable domain identified by SEQ ID NO:61 and
ii. three light chain CDR sequences with at most 10 amino acid changes compared to the CDR sequences of the light chain variable domain identified by SEQ ID NO:62 or s.
i. three heavy chain CDR sequences with at most 10 amino acid changes compared to the CDR sequences of the heavy chain variable domain identified by SEQ ID NO:63 and
ii. three light chain CDR sequences with at most 10 amino acid changes compared to the CDR sequences of the light chain variable domain identified by SEQ ID NO:64.

98. The antibody or antigen-binding fragment thereof according to embodiment 97, wherein the three heavy chain CDR sequences have at most 9, such as 8, such as 7 or such as 6 amino acid changes compared to the CDRs of the identified SEQ IDs.

99. The antibody or antigen-binding fragment thereof according to embodiment 97, wherein the three heavy chain CDR sequences have at most 5, such as 4, such as 3, such as 2 or at most 1 amino acid changes compared to the CDRs of the identified SEQ IDs.

100. The antibody or antigen-binding fragment thereof according to embodiment 97, wherein the three light chain CDR sequences have at most 9, such as 8, such as 7 or such as 6 amino acid changes compared to the CDRs of the identified SEQ IDs.

101. The antibody or antigen-binding fragment thereof according to embodiment 97, wherein the three light chain CDR sequences have at most 5, such as 4, such as 3, such as 2 or at most 1 amino acid changes compared to the CDRs of the identified SEQ IDs.

102. The antibody or antigen-binding fragment thereof according to any of the previous embodiments, wherein the antibody or antigen-binding fragment thereof comprises
a. the CDR sequences of the heavy chain variable domain identified by SEQ ID NO:21 and the CDR sequences of the light chain variable domain identified by SEQ ID NO:22,
b. the CDR sequences of the heavy chain variable domain identified by SEQ ID NO:25 and the CDR sequences of the light chain variable domain identified by SEQ ID NO:26,
c. the CDR sequences of the heavy chain variable domain identified by SEQ ID NO:27 and the CDR sequences of the light chain variable domain identified by SEQ ID NO:28,
d. the CDR sequences of the heavy chain variable domain identified by SEQ ID NO:29 and the CDR sequences of the light chain variable domain identified by SEQ ID NO:30,
e. the CDR sequences of the heavy chain variable domain identified by SEQ ID NO:31 and the CDR sequences of the light chain variable domain identified by SEQ ID NO:32,
f. the CDR sequences of the heavy chain variable domain identified by SEQ ID NO:33 and the CDR sequences of the light chain variable domain identified by SEQ ID NO:34,
g. the CDR sequences of the heavy chain variable domain identified by SEQ ID NO:35 and the CDR sequences of the light chain variable domain identified by SEQ ID NO:36,
h. the CDR sequences of the heavy chain variable domain identified by SEQ ID NO:37 and the CDR sequences of the light chain variable domain identified by SEQ ID NO:38,
i. the CDR sequences of the heavy chain variable domain identified by SEQ ID NO:39 and the CDR sequences of the light chain variable domain identified by SEQ ID NO:40,
j. the CDR sequences of the heavy chain variable domain identified by SEQ ID NO:41 and the CDR sequences of the light chain variable domain identified by SEQ ID NO:42,
k. the CDR sequences of the heavy chain variable domain identified by SEQ ID NO:43 and the CDR sequences of the light chain variable domain identified by SEQ ID NO:44,
l. the CDR sequences of the heavy chain variable domain identified by SEQ ID NO:51 and the CDR sequences of the light chain variable domain identified by SEQ ID NO:52,
m. the CDR sequences of the heavy chain variable domain identified by SEQ ID NO:53 and the CDR sequences of the light chain variable domain identified by SEQ ID NO:54,
n. the CDR sequences of the heavy chain variable domain identified by SEQ ID NO:55 and the CDR sequences of the light chain variable domain identified by SEQ ID NO:56,
o. the CDR sequences of the heavy chain variable domain identified by SEQ ID NO:57 and the CDR sequences of the light chain variable domain identified by SEQ ID NO:58, p. the CDR sequences of the heavy chain variable domain identified by SEQ ID NO:59 and the CDR sequences of the light chain variable domain identified by SEQ ID NO:60,
q. the CDR sequences of the heavy chain variable domain identified by SEQ ID NO:61 and the CDR sequences of the light chain variable domain identified by SEQ ID NO:62 or
r. the CDR sequences of the heavy chain variable domain identified by SEQ ID NO:63 and the CDR sequences of the light chain variable domain identified by SEQ ID NO:64.

103. The antibody or antigen-binding fragment thereof according to any of the previous embodiments, wherein the antibody or antigen-binding fragment thereof comprises a heavy chain variable domain and a light chain variable domain identified by
    a. SEQ ID NO:21 and 22,
    b. SEQ ID NO:25 and 26,
    c. SEQ ID NO:27 and 28,
    d. SEQ ID NO:29 and 30,
    e. SEQ ID NO:31 and 32,
    f. SEQ ID NO:33 and 34,
    g. SEQ ID NO:35 and 36,
    h. SEQ ID NO:37 and 38,
    i. SEQ ID NO:39 and 40,
    j. SEQ ID NO:41 and 42,
    k. SEQ ID NO:43 and 44,
    l. SEQ ID NO:51 and 52,
    m. SEQ ID NO:53 and 54,
    n. SEQ ID NO:55 and 56,
    o. SEQ ID NO:57 and 58,
    p. SEQ ID NO:59 and 60,
    q. SEQ ID NO:61 and 62 or
    r. SEQ ID NO:63 and 64, respectively.

104. The antibody or antigen-binding fragment thereof according to embodiment 57, wherein the antibody or antigen-binding fragment thereof belong to "Bin D".

105. The antibody or antigen-binding fragment thereof according to embodiment 57, wherein the antibody or antigen-binding fragment thereof competes with a reference antibody wherein the reference antibody comprises a heavy chain variable domain identified by SEQ ID NO:47 and a light chain variable domain identified by SEQ ID NO:48.

106. The antibody according to the previous embodiment, wherein the reference antibody is a Fab.

107. The antibody or antigen-binding fragment thereof according to any of the previous embodiments, wherein the antibody or antigen-binding fragment thereof comprises
    a. a heavy chain variable domain at least 90% identical to the sequence identified by SEQ ID NO:47 and a light chain variable domain at least 90% identical to the sequence identified by SEQ ID NO:48,
    b. a heavy chain variable domain at least 90% identical to the sequence identified by SEQ ID NO:45 and a light chain variable domain at least 90% identical to the sequence identified by SEQ ID NO:46,
    c. a heavy chain variable domain at least 90% identical to the sequence identified by SEQ ID NO:51 and a light chain variable domain at least 90% identical to the sequence identified by SEQ ID NO:52 or
    d. a heavy chain variable domain at least 90% identical to the sequence identified by SEQ ID NO:61 and a light chain variable domain at least 90% identical to the sequence identified by SEQ ID NO:62.

108. The antibody or antigen-binding fragment thereof according to embodiment 107, wherein in the heavy chain variable domain is at least 92, 94, 96 or 98% identical to the identified SEQ IDs.

109. The antibody or antigen-binding fragment thereof according to embodiment 107, wherein in the light chain variable domain is at least 92, 94, 96 or 98% identical to the identified SEQ IDs.

110. The antibody or antigen-binding fragment thereof according to embodiment 108 and 109, wherein both the heavy chain variable domain and the light chain variable domain are at least 92, 94, 96 or 98% identical to the identified SEQ IDs.

111. The antibody or antigen-binding fragment thereof according to any of the previous embodiments, wherein the antibody or antigen-binding fragment thereof comprises
    a.
        i. three heavy chain CDR sequences with at most 10 amino acid changes compared to the CDR sequences of the heavy chain variable domain identified by SEQ ID NO:47 and
        ii. three light chain CDR sequences with at most 10 amino acid changes compared to the CDR sequences of the light chain variable domain identified by SEQ ID NO:48,
    b.
        i. three heavy chain CDR sequences with at most 10 amino acid changes compared to the CDR sequences of the heavy chain variable domain identified by SEQ ID NO:45 and
        ii. three light chain CDR sequences with at most 10 amino acid changes compared to the CDR sequences of the light chain variable domain identified by SEQ ID NO:46,
    c.
        i. three heavy chain CDR sequences with at most 10 amino acid changes compared to the CDR sequences of the heavy chain variable domain identified by SEQ ID NO:51 and
        ii. three light chain CDR sequences with at most 10 amino acid changes compared to the CDR sequences of the light chain variable domain identified by SEQ ID NO:52 or
    d.
        i. three heavy chain CDR sequences with at most 10 amino acid changes compared to the CDR sequences of the heavy chain variable domain identified by SEQ ID NO:61 and
        ii. three light chain CDR sequences with at most 10 amino acid changes compared to the CDR sequences of the light chain variable domain identified by SEQ ID NO:62.

112. The antibody or antigen-binding fragment thereof according to embodiment 111, wherein the three heavy chain CDR sequences have at most 9, such as 8, such as 7 or such as 6 amino acid changes compared to the CDRs of the identified SEQ IDs.

113. The antibody or antigen-binding fragment thereof according to embodiment 111, wherein the three heavy chain CDR sequences have at most 5, such as 4, such as 3, such as 2 or at most 1 amino acid changes compared to the CDRs of the identified SEQ IDs.

114. The antibody or antigen-binding fragment thereof according to embodiment 111, wherein the three light chain CDR sequences have at most 9, such as 8, such as 7 or such as 6 amino acid changes compared to the CDRs of the identified SEQ IDs.

115. The antibody or antigen-binding fragment thereof according to embodiment 111, wherein the three light chain CDR sequences have at most 5, such as 4, such as 3, such as 2 or at most 1 amino acid changes compared to the CDRs of the identified SEQ IDs.

116. The antibody or antigen-binding fragment thereof according to any of the previous embodiments, wherein the antibody or antigen-binding fragment thereof comprises
    a. the CDR sequences of the heavy chain variable domain identified by SEQ ID NO:47 and the CDR sequences of the light chain variable domain identified by SEQ ID NO:48,
    b. the CDR sequences of the heavy chain variable domain identified by SEQ ID NO:45 and the CDR sequences of the light chain variable domain identified by SEQ ID NO:46,
    c. the CDR sequences of the heavy chain variable domain identified by SEQ ID NO:51 and the CDR sequences of the light chain variable domain identified by SEQ ID NO:52 or
    d. the CDR sequences of the heavy chain variable domain identified by SEQ ID NO:61 and the CDR sequences of the light chain variable domain identified by SEQ ID NO:62.

117. The antibody or antigen-binding fragment thereof according to any of the previous embodiments, wherein the antibody or antigen-binding fragment thereof comprises
    a. a heavy chain variable domain identified by SEQ ID NO:47 and a light chain variable domain identified by SEQ ID NO:48,
    b. a heavy chain variable domain identified by SEQ ID NO:45 and a light chain variable domain identified by SEQ ID NO:46,
    c. a heavy chain variable domain identified by SEQ ID NO:51 and a light chain variable domain identified by SEQ ID NO:52 or
    d. a heavy chain variable domain identified by SEQ ID NO:61 and a light chain variable domain identified by SEQ ID NO:62.

118. The antibody or antigen-binding fragment thereof according to embodiment 57, wherein the antibody or antigen-binding fragment thereof belongs "Bin E".

119. The antibody or antigen-binding fragment thereof according to embodiment 57, wherein the antibody or antigen-binding fragment thereof competes with a reference antibody wherein the reference antibody comprises a heavy chain variable domain identified by SEQ ID NO:49 and a light chain variable domain identified by SEQ ID NO:50.

120. The antibody according to the previous embodiment, wherein the reference antibody is a Fab.

121. The antibody or antigen-binding fragment thereof according to any of the previous embodiments, wherein the antibody or antigen-binding fragment thereof comprises a heavy chain variable domain at least 90% identical to the sequence identified by SEQ ID NO:49 and a light chain variable domain at least 90% identical to the sequence identified by SEQ ID NO:50.

122. The antibody or antigen-binding fragment thereof according to embodiment 121, wherein in the heavy chain variable domain is at least 92, 94, 96 or 98% identical to the identified SEQ ID.

123. The antibody or antigen-binding fragment thereof according to embodiment 121, wherein in the light chain variable domain is at least 92, 94, 96 or 98% identical to the identified SEQ ID.

124. The antibody or antigen-binding fragment thereof according to embodiment 122 and 123, wherein both the heavy chain variable domain and the light chain variable domain are at least 92, 94, 96 or 98% identical to the identified SEQ IDs.

125. The antibody or antigen-binding fragment thereof according to any of the previous embodiments, wherein the antibody or antigen-binding fragment thereof comprises
    a. three heavy chain CDR sequences with at most 10 amino acid changes compared to the CDR sequences of the heavy chain variable domain identified by SEQ ID NO:49 and
    b. three light chain CDR sequences with at most 10 amino acid changes compared to the CDR sequences of the light chain variable domain identified by SEQ ID NO:50.

126. The antibody or antigen-binding fragment thereof according to embodiment 125, wherein the three heavy chain CDR sequences have at most 9, such as 8, such as 7 or such as 6 amino acid changes compared to the CDRs of the identified SEQ IDs.

127. The antibody or antigen-binding fragment thereof according to embodiment 125, wherein the three heavy chain CDR sequences have at most 5, such as 4, such as 3, such as 2 or at most 1 amino acid changes compared to the CDRs of the identified SEQ IDs.

128. The antibody or antigen-binding fragment thereof according to embodiment 125, wherein the three light chain CDR sequences have at most 9, such as 8, such as 7 or such as 6 amino acid changes compared to the CDRs of the identified SEQ IDs.

129. The antibody or antigen-binding fragment thereof according to embodiment 125, wherein the three light chain CDR sequences have at most 5, such as 4, such as 3, such as 2 or at most 1 amino acid changes compared to the CDRs of the identified SEQ IDs.

130. The antibody or antigen-binding fragment thereof according to any of the previous embodiments, wherein the antibody or antigen-binding fragment thereof comprises the CDR sequences of the heavy chain variable domain identified by SEQ ID NO:49 and the CDR sequences of the light chain variable domain identified by SEQ ID NO:50.

131. The antibody or antigen-binding fragment thereof according to any of the previous embodiments, wherein the antibody or antigen-binding fragment thereof comprises a heavy chain variable domain identified by SEQ ID NO:49 and a light chain variable domain identified by SEQ ID NO:50.

132. A multispecific antibody or antigen-binding fragment thereof capable of binding to FIX/FIXa and FX/FXa.

133. The multispecific antibody or antigen-binding fragment thereof according to embodiment 132, wherein the antibody comprises an antigen-binding fragment according to any of the previous embodiments 1-131.

134. The multispecific antibody or antigen-binding fragment thereof according to embodiment 132, wherein the antibody comprises an antigen-binding fragment according to any of the previous embodiments 2-30.

135. The multispecific antibody or antigen-binding fragment thereof according to embodiment 132, wherein the antibody comprises an antigen-binding fragment according to any of the previous embodiment 31-52.
136. The multispecific antibody or antigen-binding fragment thereof according to embodiment 132, wherein the antibody comprises an antigen-binding fragment according to any of the previous embodiments 57-131.
137. The multispecific antibody or antigen-binding fragment thereof according to embodiment 132, wherein the antibody comprises an antigen-binding fragment according to any of the previous embodiments 58-75.
138. The multispecific antibody or antigen-binding fragment thereof according to embodiment 132, wherein the antibody comprises an antigen-binding fragment according to any of the previous embodiments 76-89.
139. The multispecific antibody or antigen-binding fragment thereof according to embodiment 132, wherein the antibody comprises an antigen-binding fragment according to any of the previous embodiments 90-103.
140. The multispecific antibody or antigen-binding fragment thereof according to embodiment 132, wherein the antibody comprises an antigen-binding fragment according to any of the previous embodiments 104-117.
141. The multispecific antibody or antigen-binding fragment thereof according to embodiment 132, wherein the antibody comprises an antigen-binding fragment according to any of the previous embodiments 118-131
142. The multispecific antibody or antigen-binding fragment thereof according to embodiment 132, wherein the antibody comprises an antigen-binding fragment according to any of the previous embodiments 1-56 and an antigen-binding fragment according to any of the previous embodiments 57-131.
143. The multispecific antibody or antigen-binding fragment thereof according to embodiment 132, wherein the antibody comprises an antigen-binding fragment according to any of the previous embodiments 2-30 and an antigen-binding fragment according to any of the previous embodiments 58-75.
144. The multispecific antibody or antigen-binding fragment thereof according to embodiment 132, wherein the antibody comprises an antigen-binding fragment according to any of the previous embodiments 2-30 and an antigen-binding fragment according to any of the previous embodiments 76-89.
145. The multispecific antibody or antigen-binding fragment thereof according to embodiment 132, wherein the antibody comprises an antigen-binding fragment according to any of the previous embodiments 2-30 and an antigen-binding fragment according to any of the previous embodiments 90-103.
146. The multispecific antibody or antigen-binding fragment thereof according to embodiment 132, wherein the antibody comprises an antigen-binding fragment according to any of the previous embodiments 31-52 an antigen-binding fragment according to any of the previous embodiments 58-75.
147. The multispecific antibody or antigen-binding fragment thereof according to embodiment 132, wherein the antibody comprises an antigen-binding fragment according to any of the previous embodiments 31-52 and an antigen-binding fragment according to any of the previous embodiments 76-89.
148. The multispecific antibody or antigen-binding fragment thereof according to embodiment 132, wherein the antibody comprises an antigen-binding fragment according to any of the previous embodiments 31-52 and an antigen-binding fragment according to any of the previous embodiments 90-103.
149. The multispecific antibody or antigen-binding fragment thereof according to embodiment 132 wherein the antibody is a bispecific antibody capable of specifically binding FIX/FIXa and FX/FXa wherein the binding domains are derived the mAb pairs consisting of: mAb1-1371/mAb1-1307, mAb1-6705/mAb1-1307, mAb1-1371/mAb0-1886, mAb1-7441/mAb0-1886, mAb1-7447/mAb0-1886, mAb1-7481/mAb0-1886, mAb1-1371/mAb0-1998, mAb1-6716/mAb0-1998, mAb1-6723/mAb0-1998, mAb1-6730/mAb0-1998, mAb1-6731/mAb0-1998, mAb1-6737/mAb0-1998, mAb1-6754/mAb0-1998, mAb1-7378/mAb0-1998, mAb1-7441/mAb0-1998, mAb1-7447/mAb0-1998, mAb/mAb0-1998, mAb1-6723/mAb1-1307, mAb1-6723/mAb0-1886, mAb1-6705/mAb0-1886, mAb1-7481/mAb0-1998 and mAb1-6705/mAb0-1998.
150. The antibody or antigen-binding fragment thereof according to any one of embodiments 132 to 149 wherein the antibody is a procoagulant bispecific antibody.
151. The antibody or antigen-binding fragment thereof according to any one of embodiments 132 to 149 wherein the antibody is a bispecific antibody capable of increasing the procoagulant activity of FIXa.
152. The antibody or antigen-binding fragment thereof according to any of embodiments 132 to 149 wherein the antibody is a bispecific antibody capable of increasing the enzymatic activity of FIXa towards FX.
153. The antibody or antigen-binding fragment thereof according to any of embodiments 132 to 149 wherein the antibody is a bispecific antibody capable of functionally substituting for FVIII and/or FVIIIa.
154. A multispecific antibody capable of stimulating the enzymatic activity of FIXa towards FX comprising a first antigen-binding site recognizing FIX (SEQ ID NO:1) or the activated form thereof (FIXa), and a second antigen-binding site recognizing FX (SEQ ID NO:2) or the activated form thereof (FXa) wherein
    a) the first antigen-binding site comprises the CDRs of an antibody selected from the group consisting of: mAb1-5743, mAb1-6584, mAb1-8768, mAb1-6037, mAb1-6081, mAb1-4857, mAb1-8780, mAb1-9016, mAb1-9015, mAb1-8467, mAb1-5783, or mAb1-5781, and
    b) the second antigen-binding site comprises the CDRs of an antibody selected from the group consisting of: mAb1-6738, mAb1-6463, mAb1-6723, mAb1-7503, or mAb1-6097.
155. A multispecific antibody capable of stimulating the enzymatic activity of FIXa towards FX comprising
    a first polypeptide recognizing FIX/FIXa, and
    a second polypeptide recognizing FX/FXa wherein
    a) the first polypeptide comprises the heavy chain variable domain and light chain variable domain of mAb1-5743, mAb1-6584, mAb1-8768, mAb1-6037, mAb1-6081, mAb1-4857, mAb1-8780, mAb1-9016, mAb1-9015, mAb1-8467, mAb1-5783, or mAb1-5781, and
    b) the second polypeptide comprises the heavy chain variable domain and light chain variable domain of mAb1-6738, mAb1-6463, mAb1-6723, mAb1-7503, or mAb1-6097.
156. The antibody according to any one of embodiments 154 or 155 wherein the antibody is a bispecific antibody.

157. The antibody according to any one of embodiments 150-156 wherein the stimulation of the enzymatic activity of FIXa towards FX is determined in a FXa generation assay as described herein using a monovalent one-armed anti-FIX/FIXa antibody where in the stimulation index is at least 94, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 3000, 4000 or 5000-fold when measured using an one-armed antibody concentration resulting in at least 80% saturation of FIXa.

158. A multispecific antibody capable of stimulating the enzymatic activity of FIXa towards FX comprising
a first antigen-binding site recognizing FIX (SEQ ID NO:1) or the activated form thereof (FIXa), and a second antigen-binding site recognizing FX (SEQ ID NO:2) or the activated form thereof (FXa), wherein
the first antigen-binding site is capable of specifically binding an epitope comprising amino acid residue R338 of FIX/FIXa, and
wherein the second antigen-binding site is capable of binding in the EGF-2 domain and/or catalytic subunit of FX/FXa.

159. The multispecific antibody according to embodiment 158 wherein the first antigen-binding site is capable of specifically binding an epitope comprising amino acid residues R338 and K341 of FIX/FIXa.

160. The multispecific antibody according to embodiment 159 wherein the first antigen-binding site is capable of specifically binding an epitope comprising amino acid residues L337, R338, S339, T340, K341 and T343 of FIX/FIXa.

161. A multispecific antibody capable of stimulating the enzymatic activity of FIXa towards FX comprising a first antigen-binding site recognizing FIX (SEQ ID NO:1) or the activated form thereof FIXa, and a second antigen-binding site recognizing FX (SEQ ID NO:2) or the activated form thereof (FXa)
wherein
the first antigen-binding site is capable of specifically binding an epitope comprising amino acid residues D332, R333, L337 and R338 of FIX/FIXa, and
wherein the second antigen-binding site is capable of binding in the EGF-2 domain and/or catalytic subunit of FX/FXa.

162. The multispecific antibody according to embodiment 161 wherein the first antigen-binding site is capable of specifically binding an epitope comprising amino acid residues K301, D332, R333, A334, T335, R338, N346 of FIX/FIXa.

163. A multispecific antibody capable of stimulating the enzymatic activity of FIXa towards FX comprising
a first antigen-binding site recognizing FIX/FIXa, and
a second antigen-binding site recognizing FX/FXa
wherein
the first antigen-binding site is capable of specifically binding an epitope comprising amino acid residues H257, K293 and N406 of FIX/FIXa, and
wherein the second antigen-binding site is capable of binding in the EGF-2 domain and/or catalytic subunit of FX/FXa.

164. The antibody according to any one of embodiments 1-56 and 132-156 wherein the stimulation of the enzymatic activity of FIXa towards FX is measured in a FXa generation assay as described herein using a monovalent one-armed anti-FIX/FIXa antibody wherein the stimulation index is at least 94, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 3000, 4000 or 5000 fold when measured using an one-armed antibody concentration resulting in at least 80% saturation of FIXa.

165. The antibody according to any one of embodiments 1-56 and 132-156 wherein the stimulation of the enzymatic activity of FIXa towards FX is measured in a FXa generation assay as described herein using a monovalent one-armed anti-FIX/FIXa antibody wherein the stimulation index is between 50 and 5000 fold, such as 94 to 2500 fold, such as 100 to 2500 fold, such as 200 to 2500 fold, such as 300 to 2500 fold, such as 400 to 2500 fold, such as 500 to 2500 fold, such as 600 to 2500 fold, such as 700 to 2500 fold, such as 800 to 2500 fold, such as 500 to 2500 fold, such as 600 to 2500 fold, such as 700 to 2500 fold, such as 800 to 2500 fold, such as 900 to 2500 fold, such as 1000 to 2500 fold or such as 1500 to 2500 fold when measured using an one-armed antibody concentration resulting in at least 80% saturation of FIXa.

166. The antibody according to any one of the previous embodiments wherein the antibody is a procoagulant antibody.

167. The antibody according to any one of the previous embodiments wherein said antibody functionally substitutes for FVIII and/or FVIIIa.

168. The antibody according to any one of the previous embodiments wherein the antibody is a bispecific antibody.

169. The antibody according to any one of the previous embodiments wherein the antibody isotype is IgG1, IgG2, IgG3 or IgG4 or a combination thereof.

170. An antibody according to any one of embodiments 57-131 wherein the light chain variable domain of said antibody or antigen-binding fragment thereof comprises amino acid residues R57, R96 (SEQ ID NO:22) and wherein the heavy chain variable domain of said antibody comprises amino acid residues W33, D52, D55, H100, Y101, Y102, H103 (SEQ ID NO:21).

171. The antibody or antigen-binding fragment thereof according to any of the previous embodiments for use in a method of treatment of a coagulopathy or blood coagulation disorder 172. A pharmaceutical composition comprising an antibody or antigen-binding fragment thereof according to any of the previous embodiments for the treatment of a coagulopathy or blood coagulation disorder.

173. A method of treating a subject suffering from a coagulopathy blood coagulation disorder, comprising administering to said subject an antibody or antigen-binding fragment thereof according to any of the previous embodiments.

174. A method according to embodiment 173 wherein the coagulopathy or blood coagulation disorder is haemophilia A or haemophilia A with inhibitors.

EXAMPLES

List of Abbreviations

ACN: Acetonitrile
CDR: Complementarity Determining Region
EGR-CK: EGR-chloromethylketone
LC-MS Liquid chromatography-mass spectrometry
FACS: Fluorescence-activated cell sorting
FIX: Coagulation Factor IX FIXa: Coagulation Factor IXa
FX: Coagulation Factor X
FXa: Coagulation Factor Xa
HA: Haemophilia A
HA-PPP: HA-induced human platelet-poor plasma
HA-PRP: HA-induced human platelet-rich plasma
hFIXa: human Coagulation Factor IXa
ITC: Isothermal Titration Calorimetry
MACS: Magnetic-activated cell sorting
OA: One-armed
PCR: Polymerase Chain Reaction
SPR: Surface Plasmon Resonance Example 1: Development of Factor IX/FIXa Fab and mAb Expression Plasmids FIX/FIXa binding antibodies as disclosed herein were identified using various antibody development methods. In order to generate a diverse set of antibodies targeting FIXa and FX, immunisations of mice and rabbits as well as selections from phage display and Adimab yeast display were performed.

Adimab Yeast Display

The Adimab platform is a yeast display system encompassing a fully human naïve IgG1/kappa library with a diversity of $10^{10}$ and covering 20 out of 42 VH families. The utilized antibody phage display platform is a proprietary fully human Fab display library. The library has a size of $10^{10}$ and was constructed by a combinational approach utilizing chemical synthesis of the light chain, as well as the heavy chain CDR1 and CDR2, complemented with PCR amplification of the heavy chain CDR3 from human peripheral blood mononuclear cells. The antibody selection process is directed using MACS and FACS based methods which allow monitoring of applied selection criteria in real time. Since selections are based on MACS and FACS, labelled antigens (e.g. biotin) are needed. Selection campaigns were performed using biotin-labelled active-site inhibited hFIXa (FIXa-EGR-biotin), or antibody mediated immobilization of hFIXa. Hits were evaluated for binding using Bio-layer interferometry (Octet fortebio systems).

Phage Display

To maximise coverage of epitope diversity, different panning strategies were explored, including panning using biotinylated FIXa-EGR, FX, active-site inhibited FXa, or antigen capture using anti-FIXa antibodies. Initial hits were identified by phage ELISA. After sequence analysis, unique hits were cloned, expressed as IgG1, and ranked using SPR (Biacore) or Bio-layer interferometry (Octet fortebio systems).

In Vivo Platforms

For generation of fully human antibodies in mice, Kymouse™ mice HK and HL 1.0 (utilizing kappa and lambda chains, respectively) were used. Additional immunisations were carried out in wild-type mice and rabbits in order to maximise antibody diversity.

Generation of anti-FIXa Antibodies

Mice or rabbits were immunized with FIXa, FIXa-EGR, or FX using standard protocols. Antibodies generated in mice or rabbits were screened in ELISA. FIXa binding rabbit B-cells were FACS-sorted using randomly biotinylated FIXa-EGR. Antibody hits from the rabbits and mice were either recombinantly expressed (rabbit mAbs) or propagated (mouse hybridomas) and antibodies were subsequently small scale purified.

Generation of Anti-FX Antibodies

Kymouse mice and rabbits were immunised with FX using standard or Repetitive Immunization at Multiple Sites (RIMMS) protocols. Rabbit B-cells were isolated by FACS sorting using randomly biotinylated FX. Anti-FX mAbs from fusions and sortings were screened using ELISA and Octet fortebio systems.

Sequencing of Kymouse and wt Mouse Derived Antibodies

Anti-FIXa and anti-FX antibody producing hybridomas derived from Kymouse mice or wt mice were sequenced and expressed in HEK293 cells using standard techniques. Expressed antibodies were evaluated for binding using Octet fortebio systems.

Resulting variable domain ($V_H$ and $V_L$) encoding DNA sequences of selected antibodies were inserted into a pTT-based mammalian expression vector (Durocher et al (2002) Nucleic Acid Res. 30: E9) or into a pcDNA3.4 mammalian expression vector (Invitrogen) containing antibody constant region encoding DNA sequences. For pTT/pcDNA3.4 mAb expression vectors, the $V_H$ and $V_L$ DNA sequences were inserted in-frame with human IgG1 or IgG$_4$ S228P ($C_H$1 $C_H$2$C_H$3) or human $C_L$ kappa constant region encoding DNA sequences, respectively. For the corresponding pTT/pcDNA3.4 Fab expression vectors the $V_H$ DNA sequences were inserted in-frame with human IgG, $C_H$1 encoding DNA sequences. For the 224F3 reference compound used in Example 6, 8 and 18 below, the 224F3 $V_H$ and $V_L$ sequences were obtained from EP1660536 B1 (SEQ ID NO:1 and 2, respectively). 224F3 $V_H$ and $V_L$ encoding DNA sequences were inserted into a pTT5/pcDNA3.4-based mammalian expression vector in-frame with human IgG1 ($C_H$1$C_H$2$C_H^3$) or human $C_L$ kappa constant region encoding DNA sequences, respectively.

All expression vectors included a 5'end DNA sequence containing a kozak sequence and a DNA sequence encoding a signal peptide in-frame with the antibody encoding DNA sequences.

Example 2: Recombinant Expression of Antibodies and Antibody Fab Fragments

Antibodies and antibody Fab fragments were expressed using transient transfection of HEK293 suspension cells (293Expi, Invitrogen) essentially following manufacturer's instructions. 293Expi cells were typically subcultivated every 3-4 days in Expi293F expression medium (Invitrogen, catalogue number A1435104) supplemented with 1% P/S (GIBCO catalogue number 15140-122). Expi293F cells were transfected at a cell density of 2.5-3 mill/mL using Expifectamine. For each litre of Expi293F cells, the transfection was performed by diluting a total of 1 mg of plasmid DNA ($V_H$—$C_H$1 (for Fab) or $V_H$—$C_H$1-$C_H$2-$C_H$3 (for mAb) and LC plasmids in 1:1 ratio) into 50 mL Optimem (GIBCO, cat. no. 51985-026, dilution A) and by diluting 2.7 mL Expifectamine into 50 mL Optimem (dilution B). For Fab and mAb producing co-transfections, $V_H$—$C_H$1 and LC plasmids (Fab) and $V_H$—$C_H$1-$C_H$2-$C_H$3 and LC plasmids (mAb), respectively, were used in a 1:1 ratio. Dilution A and B were mixed and incubated at room temperature for 10-20 minutes. The transfection mix was hereafter added to the Expi293F cells and cells were incubated at 37° C. in a humidified incubator with orbital rotation (85-125 rpm). One day post-transfection, transfected cells were supplemented with 5 ml of ExpiFectamine 293 Transfection Enhancer 1 and 50 ml of ExpiFectamine 293 Transfection Enhancer 2. Cell culture supernatants were typically harvested 4-5 days post-transfection by centrifugation followed by filtration.

Example 3: Fab and Antibody Purification and Characterization

Fab Purification and Characterization

Purification of Fab molecules was conducted as a 2-step process composed of affinity chromatography using a kappaSelect resin (GE Healthcare, cat. no. 17-5458-11) and size-exclusion chromatography using a Superdex200 resin (GE Healthcare, cat. no. 17-1043-04). Purifications were conducted using an ÄktaExplorer chromatography system (GE Healthcare, cat. no. 18-1112-41). The buffer systems used for the affinity purification step were an equilibration buffer composed of 20 mM NaPhosphate pH 7.2, 150 mM NaCl and an elution buffer composed of 10 mM Formic acid pH 3.5 and a pH-adjustment buffer composed of 0.4 M NaPhosphate pH 9.0. Cell supernatants were applied directly without any adjustments onto a pre-equilibrated kappaSelect SuRe column. The column was washed with 10 column volumes of equilibration buffer and the Fab molecules were eluted isocratically in approx. 5 column volumes of elution buffer. The pH of the pooled fractions was adjusted to neutral using the described pH-adjustment buffer immediately after elution. The Fab molecules were further purified and buffer exchanged using said gel filtration resin pre-packed in a column. The running buffer used for size exclusion chromatography was 25 mM HEPES and 150 mM NaCl, pH 7.4. The Fab molecules eluted as single peaks at approx. 0.5 column volumes. Fractions covering the peak were analysed using a size-exclusion High-Performance Liquid Chromatographic (SE-HPLC) method setup on an Agilent LC 1100/1200 system and using a BIOSep-SEC-S3000 300×7.8 mm column (Phenomenex, cat. no. OOH-2146-KO) and a running buffer composed of 200 mM NaPhosphate pH 6.9, 300 mM NaCl and 10% isopropanol. Based on this analysis, fractions were pooled to obtain a homogenous protein preparation. The final preparation eluted as a single symmetric peak at a retention time of approx. 10 min at a flow rate of 1 ml/min.

The purified Fab molecules were further characterized using SDS-PAGE/Coomassie and liquid-chromatography mass spectrometry analyses. The SDS-PAGE/Coomassie analysis was performed using NuPage 4-12% Bis-Tris gels (Invitrogen, cat. no. NP0321 BOX). All Fab molecules displayed expected light chain and heavy chain components. Intact molecular mass determinations were performed using a Liquid Chromatography Electrospray Ionisation Time-of-Flight Mass Spectrometry method setup on an Agilent 6210 instrument and a desalting column MassPREP (Waters, cat. no. USRM10008656). The buffer system used was an equilibration buffer composed of 0.1% Formic acid in LC-MS graded-H$_2$O and an elution buffer composed of 0.1% formic acid in LC-MS graded-ACN. All Fab molecules displayed expected intact molecular masses in accordance with sequence. The final purity was determined based on SE-HPLC analysis. Purity estimates were all between 95-99% for the different Fab fragments. To determine the final protein concentrations, absorbance measurement at 280 nm using a NanoDrop spectrophotometer (Thermo Scientific) was performed and concentrations calculated using specific extinction coefficients for each of the Fab molecules.

Antibody Purification and Characterization

Purification of the antibodies was conducted by affinity chromatography using a Protein A MabSelect SuRe resin (GE Healthcare, cat. no. 17-5438-01). Purifications were conducted using an ÄktaExplorer chromatography system (GE Healthcare, cat. no. 18-1112-41). The buffer systems used for the affinity purification step were an equilibration buffer was composed of 20 mM NaPhosphate pH 7.2, 150 mM NaCl and an elution buffer composed of 10 mM Formic acid pH 3.5 and a pH-adjustment buffer composed of 0.4 M NaPhosphate pH 9.0. Cell supernatants were applied directly without any adjustments onto a pre-equilibrated MabSelect SuRe column. The column was washed with 10 column volumes of equilibration buffer and the antibodies were eluted isocratically in approx. 2-5 column volume of elution buffer. The pH of the pooled fractions was adjusted to neutral using the described pH-adjustment buffer immediately after elution.

The purified antibodies were characterized using SDS-PAGE/Coomassie, size-exclusion high-pressure liquid-chromatography (SE-HPLC) and liquid-chromatography mass spectrometry (LC-MS) analyses. The SDS-PAGE/Coomassie analysis was performed using NuPage 4-12% Bis-Tris gels (Invitrogen, cat. no. NP0321 BOX). Here, all antibodies displayed expected light chain and heavy chain components. Intact molecular mass determinations were performed using a Liquid Chromatography Electrospray Ionisation Time-of-Flight Mass Spectrometry method setup on an Agilent 6210 instrument and a desalting column MassPREP (Waters, cat. no. USRM10008656). The buffer system used was an equilibration buffer composed of 0.1% Formic acid in LC-MS graded-H$_2$O and an elution buffer composed of 0.1% formic acid in LC-MS graded-ACN. Analyses were performed with and without N-Glycosidase F (Roche Diagnostics, cat. no. 11365177001) and reducing agent (i.e. mercaptoethanol or DTT). All antibodies displayed expected intact molecular masses in accordance with sequence and one heavy chain N-glycan. Purity was determined based on SE-HPLC. The final protein purity was analysed based on SE-HPLC method setup on an Agilent LC 1100/1200 system and using a BIOSep-SEC-S3000 300×7.8 mm column (Phenomenex, cat. no. OOH-2146-KO) and a running buffer composed of 200 mM NaPhosphate pH 6.9, 300 mM NaCl and 10% isopropanol. UV280 and fluorescence (Ex 280 nm/Em 354 nm) detectors was used for detection. The antibodies eluted as single symmetric peaks with retention times reflecting the size of the antibodies. Purity estimates were all between 95-99% for the different antibodies. To measure the final protein concentrations, a NanoDrop spectrophotometer (Thermo Scientific) was used together with specific extinction coefficients for each of the antibodies.

Example 4: Binning of Anti-FIXa Stimulating Antibodies

Antibodies selected as capable of stimulating the enzymatic activity of FIXa towards FX were analysed in binning experiments to determine the binding characteristics for the identified antibodies using the method described below.

Method for Binning of Antibodies

Binning experiments were performed using Octet fortebio systems (HTX, Red384) equipped with anti-human IgG sensors (Pall Life Sciences, Menlo Park, CA), and using 8 or 32-channel mode (Red384 and HTX). The binning assays were performed using the classical sandwich epitope binning setup. Briefly, (1) the first antibody was captured by anti-human AHC tips (anti-human IgG Fc capture tips (AHC Part NO:18-5064), (2) non-blocked IgG binding sites on the AHC tips were blocked by human polyclonal IgG (14506

SIGMA), (3) FIXa was bound to the first antibody, (4) the competing antibody was offered to the antibody-antigen complex on the tips, and if no binding of the secondary antibody could be detected, the antibodies were scored as belonging to the same bin.

The analysis identified two different bins, Bin 1 and 2, defined by the antibodies mAb0-1886 and mAb1-1307, respectively.

Binning of Anti-FIX Antibodies.

Selected anti-FIX antibodies were binned against each other, and two different bins (Bin 1 and 2) were identified. Numbers refer to mAb ID, e.g. 0-1998 denotes mAb0-1998.

| Bin 1 mAb0-1886 | Bin 2 mAb1-1307 |
| --- | --- |
| 0-1998 | |
| 0-2000 | |
| 0-2001 | |
| 0-2003 | |
| 1-0985 | |
| 1-0982 | |
| 1-0072 | 1-0072 |
| 1-0073 | 1-0073 |
| | 1-1448 |
| | 1-0970 |

The overview shows that several antibodies were found to belong to Bin 1, including mAb0-1886 and mAb0-1998. Bin 2 was found to include four antibodies in addition to mAb1-1307. Two antibodies, mAb1-0072 and mAb1-0073, were common to Bin 1 and 2.

Variants of Parental Antibodies (Lineages) as Disclosed Herein Share Bins and Epitope (Hot-Spot) Residues with Parental Antibodies Since the antibody variants for which data are provided in the present example do not contain amino acid substitutions on positions shown to be crucial for epitope recognition based on the crystal structures of the parental antibody-FIXa complexes provided in Example 5, a person skilled in the art would understand that the variants as a starting point will belong to the same bin, compete for binding with, and recognize at least the same hot-spot residues in the FIX/FIXa epitope as the antibody from which they originate, i.e. mAb0-1998, mAb0-1886, or mAb1-1307.

Example 5: Crystallization and Epitope Mapping of Anti-FIX/FIXa Antibodies Using X-Ray Crystallography The FIXa protein used for crystallization (Cambridge ProteinWorks, Product Code 10316) is composed of a truncated light chain (residues 85-142 of SEQ ID NO:1) with a non-natural methionine residue attached at the N-terminus as a result of bacterial expression, and a heavy chain containing residues 181-415 of SEQ ID NO:1. The active site of the protease is blocked by EGR-chloromethylketone.

Crystallisation

Fab0-7237:FIXa Crystals of Fab0-7237 (Fab fragment corresponding to mAb0-1886) mixed in a 1:1 molar ratio with the FIXa protein were grown using the hanging drop vapour diffusion technique at 18° C. A protein solution of 0.8 µl 7.5 mg/ml in 20 mM Tris-HCl, pH 7.4, 50 mM NaCl, and 2.5 mM CaCl$_2$ was mixed with an equal volume of 4 M sodium formate as precipitant and incubated over 1 ml precipitant.

Fab0-7238:FIXa

Crystals of Fab0-7238 (Fab fragment corresponding to mAb0-1998) mixed in a 1:1 molar ratio with the FIXa protein were grown using the sitting drop vapour diffusion technique at 18° C. A protein solution of 0.1 µl 6.2 mg/ml in 20 mM Tris-HCl, pH 7.4, 50 mM NaCl, and 2.5 mM CaCl$_2$ was mixed with 0.1 µl of 100 mM sodium cacodylate, pH 6.5 and 1 M tri-sodium citrate as precipitant and incubated over 60 µl precipitant.

Fab0-7236:FIXa

Crystals of Fab0-7236 (Fab fragment corresponding to mAb1-1307) mixed in a 1:1 molar ratio with the FIXa protein were grown using the sitting drop vapour diffusion technique at 18° C. A protein solution of 0.1 µl 6.4 mg/ml in 20 mM Tris-HCl, pH 7.4, 50 mM NaCl, and 2.5 mM CaCl$_2$ was mixed with an equal volume of 0.2 M lithium sulphate, 40 (v/v) % PEG400, and 0.1 M Tris pH, 8.5 as precipitant and incubated over 1 ml precipitant.

Diffraction Data Collection

Fab0-7237:FIXa

The crystal was cryo protected in a solution consisting of 3 M sodium formate, 4% glycerol, 4% ethylene glycol, 4.5% sucrose, and 1% glucose prior to flash cooling in liquid nitrogen. Diffraction data were collected at 100K at the Swiss Light Source beamline X06DA (1.0000 Å wavelength) using a Pilatus2M pixel detector from Dectris. Autoindexing, integration and scaling of the data were performed with programmes from the XDS package (diffracting data statistics are summarised in Table 1).

Fab0-7238:FIXa

The crystal was cryo protected in a solution consisting of 75 mM sodium cacodylate, pH 6.5 and 0.75 M tri-sodium citrate, 4% glycerol, 4% ethylene glycol, 4.5% sucrose, and 1% glucose prior to flash cooling in liquid nitrogen. Diffraction data were collected at 100K at the Swiss Light Source beamline X06DA (1.0000 Å wavelength) using a Pilatus2M pixel detector from Dectris. Autoindexing, integration and scaling of the data were performed with programmes from the XDS package (diffracting data statistics are summarised in Table 1).

Fab0-7236:FIXa

Three crystals were cryo protected in a solution consisting of 0.15 M lithium sulphate, 30 (v/v) % PEG400, and 0.075 M Tris pH, 8.5, 4% glycerol, 4% ethylene glycol, 4.5% sucrose, and 1% glucose prior to flash cooling in liquid nitrogen. Diffraction data were collected at 100K at the Swiss Light Source beamline X06DA (1.0000 Å wavelength) using a Pilatus2M pixel detector from Dectris. Autoindexing, integration, merging and scaling of the data were performed with programmes from the XDS package (diffracting data statistics are summarised in Table 1).

Structure Determination and Refinement

Fab0-7237:FIXa

The structure was determined by molecular replacement using Phaser as implemented in the programme suite Phenix with the chains H and L of protein data bank entry 4NP4 and chains H and L from protein data bank entry 3KCG. The asymmetric unit contains two Fab:FIXa complexes. The model was refined using steps of Phenix refinement and manual rebuilding in COOT. The refinement statistics are found in Table 1.

Fab0-7238:FIXa

The structure was determined by molecular replacement using Phaser as implemented in the programme suite Phenix with the chains H and L of protein data bank entry 4PUB and chains H and L from protein data bank entry 3KCG. The asymmetric unit contains two Fab:FIXa complexes. The model was refined using steps of Phenix refinement and manual rebuilding in COOT. The refinement statistics are found in Table 1.

Fab0-7236:FIXa

The structure was determined by molecular replacement using Phaser as implemented in the programme suite Phenix with the Fab part of complex structure of Fab0-7238:FIXa complex described above and chains H and L from protein data bank entry 3KCG. The asymmetric unit contains one Fab:FIXa complex. The model was refined using steps of Phenix refinement and manual rebuilding in COOT. The refinement statistics are found in Table 1.

The epitopes of mAb0-1998 and mAb0-1886 were found to be overlapping which corresponds well with the observation that the two antibodies compete for binding to FIX/FIXa (Example 4).

Variants of Parental Antibodies (Lineages) as Disclosed Herein Share Bins and Epitope (Hot-Spot) Residues with Parental Antibodies Since the antibody variants for which data are provided in the Example 4 above and certain examples below do not

TABLE 1

Data collection and refinement statistics

| | Fab0-7237 in complex with Gladomaineless FIXa (WT) EGR-CK inhibited | Fab0-7238 in complex with Gladomaineless FIXa (WT) EGR-CK inhibited | Fab0-7236 in complex with Gladomaineless FIXa (WT) EGR-CK inhibited |
|---|---|---|---|
| Wavelength (Å) | 1.0000 | 1.0000 | 1.0000 |
| Resolution range (Å) | 48.36-2.45 (2.538-2.45) | 45.71-2.05 (2.123-2.05) | 43.64-2.0 (2.071-2.0) |
| Space group | $P6_1$ | C2 | I222 |
| Unit cell (Å, °) | 243.41 243.41 72.29 90 90 120 | 369.38 94.42 60.93 90 98.868 90 | 87.18 96.86 201.38 90 90 90 |
| Total reflections | 927423 (88310) | 443072 (43104) | 1167939 (113684) |
| Number of crystals | 1 | 1 | 3 |
| Unique reflections | 90260 (8982) | 128149 (12523) | 57871 (5716) |
| Multiplicity | 10.3 (9.8) | 3.5 (3.4) | 20.2 (19.9) |
| Completeness (%) | 99.96 (99.94) | 98.73 (97.31) | 99.89 (99.79) |
| Mean I/sigma(I) | 9.98 (1.10) | 13.50 (1.12) | 9.06 (1.26) |
| Wilson B-factor | | 39.05 | 30.10 |
| R-merge | 0.2704 (2.638) | 0.08249 (1.269) | 0.3714 (3.07) |
| R-meas | 0.2847 (2.784) | 0.09768 (1.503) | 0.381 (3.151) |
| R-pim | 0.08848 (0.8856) | 0.05184 (0.7982) | 0.08447 (0.7044) |
| CC½ | 0.991 (0.348) | 0.998 (0.571) | 0.995 (0.595) |
| CC* | 0.998 (0.718) | 1 (0.853) | 0.999 (0.864) |
| Reflections used in refinement | 90261 (8984) | 128040 (12521) | 57825 (5715) |
| Reflections used for R-free | 1928 (199) | 1611 (157) | 1461 (143) |
| R-work | 0.2013 (0.3016) | 0.2242 (0.4200) | 0.1971 (0.3096) |
| R-free | 0.2411 (0.3533) | 0.2607 (0.4969) | 0.2454 (0.3350) |
| CC(work) | 0.904 (0.507) | 0.949 (0.654) | 0.964 (0.755) |
| CC(free) | 0.884 (0.269) | 0.954 (0.435) | 0.938 (0.663) |
| Number of non-hydrogen atoms | 11731 | 11849 | 6132 |
| macromolecules | 11219 | 11196 | 5579 |
| ligands | 52 | 2 | 61 |
| solvent | 460 | 651 | 492 |
| Protein residues | 1465 | 1456 | 720 |
| RMS(bonds) | 0.015 | 0.008 | 0.008 |
| RMS(angles) | 1.22 | 1.15 | 1.13 |
| Ramachandran favored (%) | 90.91 | 95.28 | 96.20 |
| Ramachandran allowed (%) | 7.70 | 4.65 | 3.38 |
| Ramachandran outliers (%) | 1.39 | 0.07 | 0.42 |
| Rotamer outliers (%) | 6.46 | 0.40 | 0.81 |
| Clashscore | 8.48 | 6.71 | 5.39 |
| Average B-factor | 46.41 | 49.46 | 38.01 |
| macromolecules | 46.59 | 49.64 | 37.38 |
| ligands | 56.40 | 79.63 | 69.03 |
| solvent | 41.00 | 46.15 | 41.27 |
| Number of TLS groups | 40 | | |
| Twin refinement | h, -h-k, -l | | |

Determination of Epitopes

Based on the above mAb0-1998, mAb1-1307 and mAb0-1886 were found to bind to different epitopes on FIXa where the epitope is defined as residues having at least one heavy atom within a distance of 3.5 Å from a heavy atom in the antibody.

The mAb0-1998 epitope is located in the 170-loop and comprises the following residues in the protease domain: L337, R338, S339, T340, K341, and T343.

The mAb1-1307 epitope comprises the following residues: H256, H257, N258, K293, R403, Y404, N406, W407, E410 and K411.

The mAb0-1886 epitope is located in the 170-helix and comprises of the following residues in the protease domain: K301, D332, R333, A334, T335, R338 and N346.

contain amino acid substitutions on positions shown to be crucial for epitope recognition based on the crystal structures of the parental antibody-FIXa complexes provided in the present example, a person skilled in the art would understand that the variants as a starting point will belong to the same bin, compete for binding with, and recognize at least the same hot-spot residues in the FIX/FIXa epitope as the antibody from which they originate, i.e. mAb0-1998, mAb0-1886, or mAb1-1307.

Example 6: Activity of Bivalent Anti-FIX/FIXa Antibodies in a FXa Generation Assay The stimulatory effect on the enzymatic activity of FIXa towards FX of bivalent anti-FIX/FIXa antibodies was determined from their ability to promote FX activation by FIXa in the presence of a procoagulant phospholipid membrane according to the principles described by Scheiflinger et al. (2008) J Thromb Haemost, 6:315-322. Given the high activity of anti-FIXa antibody 224F3 among the antibodies identified by Scheiflinger et al. 224F3 was chosen as reference in the following experiments (cf. Example 1 for information on 224F3 construction). The stimulating effect of anti-FIXa antibodies on FIXa mediated activation of FX into FXa was measured in an automated high through-put biochemical assay in 384-well plates. In brief, FIXa was mixed with purified antibody in a four-point 5-fold dose-response. FX/phospholipid (PL) mix was added and FXa generation was measured by adding FXa substrate (Pefaflour) and the substrate hydrolysis rate determined by detecting fluorescence for five minutes on a multi-label reader (PheraSTAR). Relative FIXa stimulatory activity was calculated as the rate of FXa generation from FIXa-antibody complex versus FIXa alone.

Each antibody was tested in a concentration range from 0-200 nM by pre-incubation with 3 nM human plasma-derived FIXa (Haematologic Technologies Inc, USA) and 10 µM 25:75 phosphatidyl serine:phosphatidyl choline phospholipid vesicles (Haematologic Technologies Inc, USA) in assay buffer (50 mM HEPES, 100 mM NaCl, 5 mM $CaCl_2$, 0.1% (w/v) PEG8000, pH 7.3+1 mg/ml BSA) for 10 min before addition of human plasma-derived FX (Haematologic Technologies Inc, USA) to a concentration of 150 nM. Following 10 min activation at room temperature, the reaction (50 µl) was quenched by addition of 25 µl quench buffer (50 mM HEPES, 100 mM NaCl, 60 mM EDTA, 0.1% PEG8000, pH 7.3+1 mg/ml BSA). The amount of FXa generated was then determined by addition of 25 µl 2 mM S-2765 chromogenic substrate (Chromogenix, Sweden) and measurement of chromogenic substrate conversion by absorbance measurement at 405 nm (AOD/min) in a microplate reader. The rate of FXa generation at each antibody concentration was determined from a standard curve made with known amounts of human plasma-derived FXa (Haematologic Technologies Inc, USA).

Table 2 lists the measured FXa generation rates for each antibody at the concentrations tested. From this, peak stimulatory activities were calculated for each antibody as the observed maximum FXa generation rate relative to that of 224F3. This data is presented in Table 3, which shows that antibodies belonging to each of the three families (0-1886, 0-1998, and 1-1307, respectively) have activities that are 10-67 times higher than that observed for 224F3 (Scheiflinger et al.).

TABLE 3

Peak stimulatory activities
Peak stimulatory activities (mean ± SD, n = 2) of anti-FIX/FIXa antibodies relative to 224F3 (Scheiflinger et al.) in the FXa generation assay.

| mAb ID | Antibody family | Peak stimulatory activity relative to 224F3 |
| --- | --- | --- |
| 1-4857 | 0-1998 | 66.5 ± 6.1 |
| 1-4861 | 0-1998 | 21.7 ± 1.2 |
| 1-4707 | 1-1307 | 35.9 ± 2.1 |
| 1-4763 | 1-1307 | 20.0 ± 1.7 |
| 1-4071 | 0-1886 | 10.4 ± 0.2 |
| 1-4624 | 0-1886 | 50.1 ± 2.4 |
| 224F3 | | 1.0 |

Example 7: Preparation of Monovalent (One-Armed) Antibodies

To avoid any potential avidity effects associated with conventional monospecific and bivalent antibodies, e.g. in FXa generation assays (Example 8) and in certain SPR experiments (example 14 and 15), a monovalent one-armed (OA) antibody format was used, as described by Martens et al.: A Novel One-Armed Anti-c-Met Antibody Inhibits Glioblastoma Growth In vivo. *Clin. Cancer Res.* 12, 6144-6152 (2006), where a full heavy chain, a truncated heavy chain (lacking the Fab region) and a light chain are co-expressed. Instead of co-expression of the three chains described by Martens et al. monovalent antibodies were in the present invention prepared using the Duobody® principle as described for bispecific antibodies (Example 10). Thus, monovalent antibodies were prepared by mixing a full monospecific and bivalent antibody and a truncated heavy chain dimer (formally derived from a full antibody by removing the Fab region) and allow exchange of chains to proceed under the same experimental conditions as described in Example 10. Formation of the monovalent antibody requires that the antibody and truncated heavy chain dimer carry appropriate complementary mutations to promote hetero-dimerization, i.e. F405L/K409R for IgG1 and F405L+R409K/WT for IgG4, as described in Example 10.

In case of monovalent antibodies of the IgG1 subtype the truncation of the heavy chain can be from the N-terminus to a position in-between Cys 220 and the upper hinge Cys 226 (EU numbering). A specific example of a truncated IgG1 heavy chain is one where residues 1-220 are truncated.

In case of monovalent antibodies of the IgG4 subtype the truncation of the heavy chain can be from the N-terminus to

TABLE 2

FXa generation rates
FXa generation rates in pM/min (mean ± SD, n = 2) for the listed anti-FIX/FIXa antibodies.
Each antibody was tested in a concentration range from 0-200 nM as indicated in the first column.

| mAb conc. (nM) | 1-4857 | 1-4861 | 1-4707 | 1-4763 | 1-4071 | 1-4624 | 224F3 |
| --- | --- | --- | --- | --- | --- | --- | --- |
| 200 | 1300 ± 136 | 411 ± 39 | 586 ± 23 | 401 ± 25 | 208 ± 1 | 960 ± 10 | 5.5 ± 0.2 |
| 100 | 1262 ± 1 | 364 ± 18 | 581 ± 13 | 375 ± 1 | 198 ± 4 | 1001 ± 28 | 7.2 ± 0.5 |
| 50 | 1192 ± 37 | 352 ± 4 | 629 ± 8 | 369 ± 2 | 173 ± 2 | 989 ± 21 | 9.0 ± 0.2 |
| 25 | 1004 ± 42 | 382 ± 14 | 685 ± 20 | 373 ± 1 | 131 ± 4 | 851 ± 72 | 9.0 ± 3.6 |
| 12.5 | 685 ± 18 | 385 ± 7 | 697 ± 14 | 381 ± 10 | 97 ± 3 | 752 ± 1 | 14.7 ± 0.3 |
| 6.3 | 491 ± 6 | 415 ± 12 | 714 ± 34 | 390 ± 17 | 65 ± 4 | 550 ± 5 | 17.4 ± 0.1 |
| 3.2 | 302 ± 3 | 434 ± 15 | 662 ± 37 | 370 ± 15 | 43 ± 3 | 383 ± 3 | 20.0 ± 0.4 | a position in-between Cys 200 and the upper hinge Cys 226 (EU numbering). A specific example of a truncated IgG4 heavy chain is one where residues 1-214 are truncated.

Example 8: Activity of Monovalent Anti-FIX/FIXa Antibodies in a FXa Generation Assay To avoid any potential avidity effects arising as a consequence of the bivalency of the conventional antibody format, the stimulatory activity of anti-FIX/FIXa antibodies on FIXa enzymatic activity towards FX was determined following reformatting into a monovalent one-armed (OA) antibody format (see Example 8). Tested antibodies are listed in Table 4 below. The monovalent OA version of the anti-FIXa antibody 224F3 (denoted mAb1-1582), also referred to in Example 7, was included for comparison.

The stimulatory activity of OA antibodies was measured in assay buffer (50 mM HEPES, 100 mM NaCl, 5 mM $CaCl_2$, 0.1% (w/v) PEG8000, pH 7.3+1 mg/ml BSA) at fixed concentrations of phosphatidyl serine (PS):phosphatidyl choline (PC) phospholipid vesicles (final concentration of 500 μM; Haematologic Technologies Inc, USA) and plasma-derived FIXa (final concentrations of 0.17, 0.5 or 1 nM; Haematologic Technologies Inc, USA). The concentration of FIXa was chosen to ensure that less than 15% of the substrate FX was converted into FXa. Following pre-incubation in the presence of monovalent OA antibody (final concentrations listed in Table 1), 150 nM plasma-derived FX was added to give a final reaction volume of 50 μl, and activation was allowed to proceed for 20 min at room temperature. The reaction was then quenched by addition of 25 μl quench buffer (50 mM HEPES, 100 mM NaCl, 60 mM EDTA, 0.1% PEG8000, pH 7.3+1 mg/ml BSA) and the amount of FXa generated was determined by further addition of 25 μl 2 mM S-2765 chromogenic substrate (Chromogenix, Sweden) and measurement of chromogenic substrate conversion by absorbance measurement at 405 nm (AOD/min) in a microplate reader. The measured activity was corrected for background activity by subtraction of the signal measured in the same assay but with FIXa and antibody replaced by assay buffer, and then normalized according to the concentration of FIXa present in the assay ($[FIXa]_{total}$). Dividing this number by the similarly normalized rate of FXa generation in the absence of antibody ($A_{FIXa,norm}$), an antibody stimulation index was calculated providing the fold stimulation of FIXa activity by the antibody at the concentration used. Due to slow rate of FXa generation by free FIXa, activation reactions in the absence of antibody were carried out as described above but with 5, 10, or 20 nM FIXa present. Measured activities were then background subtracted and normalized according to the FIXa concentration in the assay. For the calculation of the stimulation index, the average of the three normalized activities of free FIXa was used.

Determination of Stimulation Index

In summary, calculation of the stimulation index can be described as follows

Stimulation index=$((A_{FIXa+OA}-A_{bckg})/[FIXa]_{total})/A_{FIXa,norm}$ where $A_{FIXa+OA}$ is the activity measured in the presence of OA antibody, $A_{bckg}$ is the background activity measured in the absence of FIXa and monovalent antibody, $[FIXa]_{total}$ is the FIXa concentration in the assay, and $A_{FIXa,norm}$ is average normalized activity of free FIXa.

Determination of FIXa saturation

The fraction of FIXa saturated with OA antibody in the assay is determined by the concentrations of FIXa and OA antibody, and the equilibrium dissociation constant ($K_d$) governing their interaction. The latter can be measured by techniques known in the art, such as isothermal titration calorimetry (ITC).

Since the stimulation index will increase as the concentration of OA antibody is increased until saturation of FIXa is reached, the concentration of OA antibody in the assay should be chosen to ensure at least 80% saturation of FIXa in the assay to provide a proper estimate of the stimulation index at full FIXa saturation.

The fraction of FIXa bound to OA antibody at equilibrium ($f_{FIXa+OA}$), can be calculated from the total concentrations of FIXa ($[FIXa]_{total}$) and OA ($[OA]_{total}$) in the assay and the equilibrium dissociation constant ($K_d$) for their interaction using the quadractic binding equation as described by Krishnaswamy et al. (1992) J. Biol. Chem., 267:23696-23706 and detailed in Eq. 1 and 2 below, wherein $[FIXa+OA]_{assay}$ represents the calculated concentration of FIXa-OA antibody complex at equilibrium in the assay $f_{FIXa+OA}$ represents the calculated fraction (in percent) of FIXa, which is bound to OA antibody at equilibrium in the assay $$[FIXa+OA]_{assay} = \frac{([FIXa]_{total}+[OA]_{total}+K_d) - \sqrt{([FIXa]_{total}+[OA]_{total}+K_d)^2 - 4\times[FIXa]_{total}\times[OA]_{total}}}{2} \quad \text{Eq. 1}$$

$$f_{FIXa+OA} = 100\% \times \frac{[FIXa+OA]_{assay}}{[FIXa]_{total}} \quad \text{Eq. 2}$$

The stimulation index for each monovalent OA antibody is provided in Table 4. For all tested antibodies the measured stimulation index was found to be higher than that measured for the monovalent one-armed 224F3 antibody (mAb1-1582).

With a concentration of one-armed 224F3 antibody of 3260 nM in the assay and a $K_d$ for the interaction with FIXa of 0.477 nM as reported by Kerschbaumer et al. (U.S. Pat. No. 7,297,336-B2), more than 95% of FIXa was bound to the one-armed 224F3 antibody in the assay.

TABLE 4

Stimulation of FIXa activity by monovalent one-armed (OA) anti-FIXa antibodies
The anti-FIX mAb ID refers to the ID of the antibody used for reformatting into the OA format. Columns labelled 'OA antibody concentration (nM)' and 'Stimulation index' list the concentration of OA antibody (nM) used in the assay and the corresponding stimulation of FIXa activity measured relative to free FIXa.

| anti-FIX mAb ID | Lineage | OA antibody concentration (nM) | Stimulation Index |
|---|---|---|---|
| 1-7977 | 0-1998 | 800 | 850 |
| 1-8785 | 0-1998 | 800 | 621 |
| 1-8782 | 0-1998 | 1600 | 417 |
| 1-8780 | 0-1998 | 1600 | 1651 |
| 1-8543 | 0-1998 | 1600 | 283 |
| 1-8679 | 0-1998 | 1600 | 918 |
| 1-9016 | 0-1998 | 1600 | 4319 |
| 1-9015 | 0-1998 | 1600 | 1334 |
| 1-9002 | 0-1998 | 800 | 567 |
| 1-9058 | 0-1998 | 1600 | 531 |

TABLE 4-continued

Stimulation of FIXa activity by monovalent one-armed
(OA) anti-FIXa antibodies
The anti-FIX mAb ID refers to the ID of the antibody used
for reformatting into the OA format. Columns labelled
'OA antibody concentration (nM)' and 'Stimulation
index' list the concentration of OA antibody (nM) used
in the assay and the corresponding stimulation of FIXa
activity measured relative to free FIXa.

| anti-FIX mAb ID | Lineage | OA antibody concentration (nM) | Stimulation Index |
|---|---|---|---|
| 1-9134 | 0-1998 | 1600 | 320 |
| 1-8467 | 0-1998 | 1600 | 1020 |
| 1-9285 | 0-1998 | 800 | 732 |
| 1-8459 | 0-1998 | 1600 | 799 |
| 1-5797 | 0-1886 | 474 | 382 |
| 1-5796 | 0-1886 | 900 | 239 |
| 1-5783 | 0-1886 | 264 | 1036 |
| 1-5781 | 0-1886 | 564 | 1219 |
| 1-5754 | 0-1886 | 1478 | 615 |
| 1-6609 | 0-1886 | 800 | 94 |
| 1-6606 | 0-1886 | 800 | 133 |
| 1-6592 | 0-1886 | 800 | 916 |
| 1-6590 | 0-1886 | 800 | 1287 |
| 1-6586 | 0-1886 | 800 | 94 |
| 1-6584 | 0-1886 | 800 | 580 |
| 1-6582 | 0-1886 | 800 | 692 |
| 1-6566 | 0-1886 | 204 | 690 |
| 224F3 (1-1582) | — | 3260 | <10 |

Example 9: Development of anti FX/FXa Fab and mAb expression plasmids Anti-FX/FXa antibodies as disclosed herein were developed using standard antibody development methods and expression plasmids were prepared as described in Example 1 for the anti-FIX/FIXa Fab and mAb expression plasmids. Expression, purification and characterisation of anti-FX/Xa antibodies were likewise performed as described for anti-FIX/FIXa antibodies in Examples 2 and 3.

Example 10: Bispecific Antibodies Prepared by In Vitro Assembly

Bispecific antibodies are generated by in vitro assembly of a first and a second antibody by the Duobody® method (Genmab) described (Labrijn et al. *PNAS* 2013, vol. 110, pp. 5145-5150) for bispecific IgG1 antibodies and using a slightly modified variant for bispecific IgG4 antibodies as detailed in the following.

For IgG1 the heavy chain constant region of the first antibody is IgG1 K409R (anti-FIX/FIXa) and the heavy chain constant region of the second antibody is IgG1 F405L (anti-FX/FXa). The IgG1 may be a IgG1 variant with reduced effector functions, as referred to earlier.

For IgG4 the heavy chain constant region of the first antibody is IgG4 S228P (anti-FIX/FIXa) and the heavy chain constant region of the second antibody is IgG4 S228P F405L R409K (anti-FX). The two parental antibodies are produced as described in Examples 1-3. The Fab arm exchange reaction is carried out in HEPES buffer (pH 7.4) under reducing conditions using 75 mM 2-mercaptoethylamine (2-MEA) and incubation at 30° C. for 3 hours.

Example 11: Procoagulant Activities of Bispecific Antibodies

Pairs of anti-FIXa and anti-hFX antibodies were made into bispecific antibodies by means of the Duobody® technology as described above (Example 10). The bispecific antibodies were tested for procoagulant activity in various assays, such as the FXa generation assays described above (Example 6) and in a Thrombin-Generation Test (TGT) as described in the following paragraph.

Thrombin Generation Test (TGT) Assay

TGT was conducted in an automated HTP 384-well setup using kaolin triggering (Haemonetics Corporation, #6300). In brief, antibodies were added at a concentration of 111 nM (except for mAb1-1371 that was added at 55 nM and mAb1-0021 that was added at 166 nM) to Haemophilia A (HA) plasma (George King). Then kaolin mixed with phospholipids (Rossix, #PL604T) was added, followed by addition of FIIa substrate (FluCa, Thrombinoscope, #TS50.00). Fluorescence was measured on a Perkin Elmer EnVision multi-label plate reader at 1 minute intervals for 2 hours. Peak height was calculated as the maximum value observed in the thrombogram, and then normalized to the peak height observed for a reference anti-FIXa and anti-FX antibody. The reference always included a binding domain from the anti-FX antibody mAb1-2375 (identified by SEQ ID NO:93 and 94), in combination with the FIX domains from each of the three families, represented by mAb1-4707, mAb1-5788 and mAb1-4857. Antibodies were grouped according to their relative TGT-activity as low (0-24%), +(24-50%), ++(50-75%) and +++(>75%), where + is preferred, ++ is more preferred and +++ is most preferred.

Selection of Preferred Combinations of Bispecific Anti-FIXa/Anti-FX Antibodies

A large number of anti-FX antibodies were tested as bispecific antibodies, in combination with anti-FIXa antibody variants belonging to the three lineages mAb1-1307, mAb0-1886 and mAb0-1998. Selected combinations of anti-FIXa/anti-FX pairs showing significant activity in the TGT assay are shown in Table 5.

TABLE 5

Procoagulant activity of bispecific antibodies
Selected pairs of anti-FIXa/anti-FX bispecific
antibodies are listed together with their activity
in the TGT-assay (as described above). Bispecific
antibodies (Duobody) were of the IgG4 sub-type, except
for mAb1-0021, mAb1-1335 and mAb1-0985, which were IgG1.

| FX mAb | FIXa mAb family | Activity | FIXa mAb |
|---|---|---|---|
| 1-6705 | 1-1307 | +++ | 1-4707 |
| 1-6716 | 1-1307 | + | 1-4707 |
| 1-6721 | 1-1307 | + | 1-4707 |
| 1-6723 | 1-1307 | + | 1-4707 |
| 1-6731 | 1-1307 | low | 1-4707 |
| 1-6737 | 1-1307 | + | 1-4707 |
| 1-1371 | 1-1307 | +++ | 1-4707 |
| 1-6705 | 0-1886 | ++ | 1-5788 |
| 1-6716 | 0-1886 | ++ | 1-5788 |
| 1-6723 | 0-1886 | + | 1-5788 |
| 1-6731 | 0-1886 | ++ | 1-5788 |
| 1-6737 | 0-1886 | ++ | 1-5788 |
| 1-7378 | 0-1886 | ++ | 1-5788 |
| 1-7413 | 0-1886 | ++ | 1-5788 |
| 1-7441 | 0-1886 | +++ | 1-5788 |
| 1-7447 | 0-1886 | +++ | 1-5788 |
| 1-7449 | 0-1886 | ++ | 1-5788 |
| 1-7462 | 0-1886 | ++ | 1-5788 |
| 1-7466 | 0-1886 | + | 1-5788 |
| 1-7481 | 0-1886 | +++ | 1-5788 |
| 1-1371 | 0-1886 | +++ | 1-4071 |
| 1-0021 | 0-1886 | low | 1-1335 |
| 1-6705 | 0-1998 | ++ | 1-4857 |
| 1-6716 | 0-1998 | +++ | 1-4857 |
| 1-6723 | 0-1998 | +++ | 1-4857 |
| 1-6730 | 0-1998 | +++ | 1-4857 |

TABLE 5-continued

Procoagulant activity of bispecific antibodies
Selected pairs of anti-FIXa/anti-FX bispecific
antibodies are listed together with their activity
in the TGT-assay (as described above). Bispecific
antibodies (Duobody) were of the IgG4 sub-type, except
for mAb1-0021, mAb1-1335 and mAb1-0985, which were IgG1.

| FX mAb | FIXa mAb family | Activity | FIXa mAb |
|---|---|---|---|
| 1-6731 | 0-1998 | +++ | 1-4857 |
| 1-6737 | 0-1998 | +++ | 1-4857 |
| 1-6754 | 0-1998 | +++ | 1-4857 |
| 1-7378 | 0-1998 | +++ | 1-4857 |
| 1-7388 | 0-1998 | + | 1-4857 |
| 1-7413 | 0-1998 | ++ | 1-4857 |
| 1-7424 | 0-1998 | ++ | 1-4857 |
| 1-7441 | 0-1998 | +++ | 1-4857 |
| 1-7447 | 0-1998 | +++ | 1-4857 |
| 1-7449 | 0-1998 | ++ | 1-4857 |
| 1-7462 | 0-1998 | ++ | 1-4857 |
| 1-7466 | 0-1998 | ++ | 1-4857 |
| 1-7481 | 0-1998 | +++ | 1-4857 |
| 1-7483 | 0-1998 | ++ | 1-4857 |
| 1-7563 | 0-1998 | ++ | 1-4857 |
| 1-7571 | 0-1998 | ++ | 1-4857 |
| 1-7591 | 0-1998 | ++ | 1-4857 |
| 1-1371 | 0-1998 | +++ | 1-4857 |
| 1-0021 | 0-1998 | low | 1-0985 |

As evident from Table 5 the level of activity exhibited by the bispecific antibody is dependent on the specific anti-FIXa/anti-FX combination. For example, the anti-FX antibody mAb1-6723 in combination with the anti-FIXa antibody mAb0-1998 exhibits strong activity (+++), whereas the activity of mAb1-6723 is lower in combination with mAb0-1886 (+) and with mAb1-1307 (+).

Example 12: Binning of Anti-FX Antibodies

Certain anti-FX antibodies showing significant TGT activity in a bispecific antibody format in combination with an anti-hFIXa antibody (Example 11) were binned against each other using the Octet fortebio systems using the same setup as described for anti-FIXa antibodies (Example 4), except for substituting FIXa with FX.

The analysis identified five different bins, Bin A-E, defined by the antibodies mAb1-1371, mAb1-1376, mAb1-6723, mAb1-7447 and mAb1-7449, respectively. Two bins, Bin A and Bin E, are each represented only by a single anti-FX antibody (see Table 6).

A large number of clones were identified in Bin C as competing with mAb1-6723.

TABLE 6

Binning of anti-FX antibodies
A selection of anti-FX antibodies were binned
against each other, and five different bins
(Bin A-E) were identified. Numbers refer to
antibody ID, e.g. 1-6723 denotes mAb1-6723.

| Bin A (1-1371) | Bin B (1-1376) | Bin C (1-6723) | Bin D (1-7447) | Bin E (1-7449) |
|---|---|---|---|---|
|  | 1-6705 |  |  |  |
|  | 1-7388 | 1-7388 |  |  |
|  | 1-7563 | 1-7563 |  |  |
|  |  | 1-6716 |  |  |
|  |  | 1-6721 |  |  |
|  |  | 1-6730 |  |  |
|  |  | 1-6731 |  |  |
|  |  | 1-6737 |  |  |
|  |  | 1-6754 |  |  |
|  |  | 1-7378 |  |  |
|  |  | 1-7413 |  |  |
|  |  | 1-7424 |  |  |
|  |  | 1-7466 |  |  |
|  |  | 1-7481 |  |  |
|  |  | 1-7483 |  |  |
|  |  | 1-7591 |  |  |
|  |  | 1-7462 |  | 1-7462 |
|  |  | 1-7571 |  | 1-7571 |
|  |  |  |  | 1-7441 |

Example 13: Crystallization and Epitope Mapping of Andi-FX Antibody Using X-Ray Crystallography Crystallisation Attempts to crystallize Fab0-8954 (Fab fragment corresponding to mAb1-6723) in complex with FX were unsuccessful, whereas good quality crystals with active-site inhibited FXa were obtained. Thus, crystals of Fab0-8954 mixed in a 1:1 molar ratio with active site inhibited des-gla FXa (human EGR-inhibited Factor Xa gla-domainless (wild-type) bacterial expression, Lot #hGDFXAEGR-022, Cambridge ProteinWorks) were grown using the sitting drop vapour diffusion technique at 18° C. A protein solution of 150 nl 6.7 mg/ml complex in 20 mM Tris-HCl, pH 7.4, 50 mM NaCl, and 2.5 mM $CaCl_2$ was mixed with 50 nl of 0.2 M magnesium acetate, 0.1 M sodium cacodylate, pH 6.5, 20% (w/v) PEG 8000 as precipitant and incubated over 60 μl precipitant.

Diffraction Data Collection

The crystal was cryo-protected by addition of 1 μl of precipitant added 20% of ethylene glycol to the crystallisation drop prior to flash cooling in liquid nitrogen. Diffraction data were collected at 100K at the Swiss Light Source beamline X06DA (1.0000 Å wavelength) using a Pilatus2M pixel detector from Dectris. Autoindexing, integration and scaling of the data were performed with programmes from the XDS package (diffracting data statistics are summarised in Table 7).

Structure Determination and Refinement

The asymmetric unit contains four Fab:FXa complexes as judged from Matthews coefficient analysis. The structure was determined by molecular replacement. Phaser as implemented in the programme suite Phenix was used with the chains H and L of protein data bank entry 5I1K as search model localising four Fabs. These were model built with the correct amino acid sequence using COOT and thereafter refined using Phenix refinement. The refined Fab model was fixed while applying molecular replacement in Molrep from the CCP4 suite with chains A and B from protein data bank entry 1 G2L as search model. Four FXa fragments were found. The model was refined using steps of Phenix refinement and manual rebuilding in COOT. The refinement statistics are found in Table 7.

TABLE 7

| Data collection and refinement statistics | |
|---|---|
| Wavelength (Å) | 1.0000 |
| Resolution range (Å) | 78.09-2.873 (2.976-2.873) |
| Space group | P2$_1$ |
| Unit cell (Å, deg) | 123.3 91.9 156.2 90 90.5 90 |
| Total reflections | 269989 (27782) |
| Unique reflections | 78735 (7779) |
| Multiplicity | 3.4 (3.6) |
| Completeness | 98.44 (98.49) |
| Mean I/sigma(I) | 9.66 (1.23) |
| Wilson B-factor (Å$^2$) | 58.38 |
| R-merge | 0.1398 (1.152) |
| R-meas | 0.166 (1.355) |
| R-pim | 0.0885 (0.7084) |
| CC½ | 0.994 (0.519) |
| CC* | 0.999 (0.826) |
| Reflections used in refinement | 78688 (7778) |
| Reflections used for R-free | 2000 (201) |
| R-work | 0.2093 (0.3449) |
| R-free | 0.2780 (0.4405) |
| CC(work) | 0.929 (0.712) |
| CC(free) | 0.911 (0.270) |
| Number of non-hydrogen atoms | 22125 |
| macromolecules | 22021 |
| ligands | 104 |
| Protein residues | 2868 |
| RMS(bonds) (Å) | 0.012 |
| RMS(angles) (deg) | 1.64 |
| Ramachandran favored (%) | 95.04 |
| Ramachandran allowed (%) | 4.11 |
| Ramachandran outliers (%) | 0.85 |
| Rotamer outliers (%) | 0.16 |
| Clashscore | 12.20 |
| Average B-factor (Å$^2$) | 60.54 |
| macromolecules | 60.55 |
| ligands | 59.50 |

Determination of Epitope

The crystal structure of the Fab0-8954:FXa complex has four copies of the complex in the asymmetric unit and these were analysed separately to identify epitope and paratope using a 3.5 Å cut-off distance.

Residues are included in the epitope for mAb1-6723 if satisfying the 3.5 Å distance criteria in at least one of the four copies of the Fab0-8954:FXa complex in the unit cell. Epitope and paratope residues for mAb1-6723 are listed in table 8.

TABLE 8

Epitope and paratope for mAb1-6723
Epitope residues for mAb1-6723 in the EGF-2
and protease domain of FX/FXa (SEQ ID NO: 2)
are listed in first and second columns,
respectively. Paratope residues in antibody V$_H$
(SEQ ID NO: 21) and V$_L$ (SEQ ID NO: 22)
are listed in columns three and four, respectively.

| Residues in EGF-2 domain | Residues in protease domain | V$_H$ | V$_L$ |
|---|---|---|---|
| H101, E103, R113, T116, L117, A118 and T127 | S227, E228, F229, Y230, E266, R287, L303, P304, E305, L419, K420, D423, R424, M426, K427 and T428 | S25, G26, Y27, S28, F29, T31, W33, D52, S54, D55, F57, S77, H100, Y101, Y102, H103, S104 and E106 | S30, S31, S32, Y33, Y50, S54, R55, R57 and R96 |

Variants of Parental Antibodies (Lineaqes) as Disclosed Herein Share Bins and Epitope (Hot-Spot) Residues with Parental Antibodies.

Since the antibody variants for which data are provided in the examples herein do not contain amino acid substitutions on positions shown to be crucial for epitope recognition based on the crystal structures of the parental antibody-FXa complexes provided in the present example, a person skilled in the art would understand that the variants as a starting point will belong to the same bin, compete for binding with, and recognize at least the same hot-spot residues in the FX/FXa epitope as the antibody from which they originate, i.e. mAb1-6723.

Example 14: Identification of Hot-Spot Residues on FX

Similar to the mapping of hot-spot epitope residues on FIX for mAb1-1307, mAb0-1886 and mAb0-1998, as described in example 15, the data provided in the present example determines the hot-spot epitope residues on FX for mAb1-6723. The FX variants used were single-site alanine variants (except for position 118, which is alanine in the wild-type, where an alanine to serine substitution was introduced) of desGla-desEGF1-FX, corresponding to residues 86-448 of SEQ ID NO:2 with a N-terminal His-tag (HHHHHH, for affinity purification) attached via a short GS-linker (GGGGSGGGGS). The variants covering epitope residues as defined in example 13 are listed in table 9.

TABLE 9

| List of generated desGla-desEGF1-FX variants | | |
|---|---|---|
| Position[1] | Variant | Domain |
| 101 | H101A | EGF2 |
| 103 | E103A | EGF2 |
| 113 | R113A | EGF2 |
| 116 | T116A | EGF2 |
| 117 | L117A | EGF2 |
| 118 | A118S | EGF2 |
| 127 | T127A | EGF2 |
| 227 | S227A | PD |
| 228 | E228A | PD |
| 229 | F229A | PD |
| 230 | Y230A | PD |
| 266 | E266A | PD |
| 287 | R287A | PD |
| 303 | L303A | PD |
| 304 | P304A | PD |
| 305 | E305A | PD |
| 419 | L419A | PD |
| 420 | K420A | PD |
| 423 | D423A | PD |
| 424 | R424A | PD |
| 426 | M426A | PD |
| 427 | K427A | PD |
| 428 | T428A | PD |

[1] According to SEQ ID No: 2
[2] EGF2 and PD refer to second epidermal growth factor-like and protease domains, respectively The wild-type desGla-desEGF1-FX and variants listed in table 9 were expressed in the HEK293 system and purified via affinity chromatography. No expression or poor purity was observed for the L117A, L303A, P304A and M426A variants, and assessment of binding was not possible for those four variants.

Identification of hot-spot epitope residues was done using a Biacore T200 instrument at 25° C. Anti-hIgG Fc antibody from the Human Antibody Capture Kit (GE Healthcare, Catalogue #BR100839) at 2 µg/ml was immobilized on a Series S Sensor Chip CM5 (GE Healthcare, Catalogue #BR100530) using standard amine coupling chemistry. The anti-FX antibody mAb4-6934 (monovalent variant of mAb1-6723) was injected at the flow rate of 5 µL/min for 30 sec and captured by the immobilized anti-hIgG Fc antibody.

Subsequently, 5 μM (with 2 or 3-fold serial dilutions) of the T116A, A118S, T127A, F229A and E226A variants, 10 μM (with 5-fold serial dilutions) of the Y230A variant, and 10 μM (with 2 or 3-fold serial dilutions) WT and H101A, E103A, R113A, S227A, E228A, R287A, E305A, L419A, K420A, D423A, R424A, K427A and T428A variants were injected at the flow rate of 5 μL/min for 90 see to allow for binding to the captured anti-FX antibody followed by a 90 see buffer injection to allow for dissociation of the desGLA-desEGF1-FX variants. The running buffer (also used for diluting the anti-FX antibody and desGLA-desEGF1-hFX variants) contained 10 mM HEPES, 150 mM NaCl, 1 mg/mL BSA and 5 mM $CaCl_2$ (pH 7.4). Regeneration of the sensor chip was achieved using 1 M formic acid. Binding data were analyzed using steady-state fitting according to the 1:1 model in the Biacore Evaluation Software 2.0 supplied by GE Healthcare. Binding data are reported as % binding of FX variants to the anti-FX antibody (monovalent mAb1-6723) relative to binding of the wild-type FX to the anti-FX antibody at 5 or 10 μM FX variants injected and are calculated according to the formula:

$$\text{Binding } (\%) = 100\% \times [(R_{max\_FXvar\_Ab})/(R_{max\_Ab})] / [(R_{max\_FXwt\_Ab})/(R_{max\_Ab})]$$

where $R_{max\_Ab}$ represents the capture level (RU) of the anti-FX antibody, and $R_{max\_FXvar\_Ab}$ and $R_{max\_FXwt\_Ab}$ represent the binding (RU) of FX variants and wild-type at the same concentration (5 μM for all except for Y230A variant, where the concentration was 10 μM) to the captured anti-FX antibody, respectively. Results are shown in table 10.

TABLE 10

Results from SPR analysis
Results from SPR analysis of monovalent variant of mAb1-6723 binding to selected FX variants covering epitope residues for mAb1-6723.

| Variant | Binding (%) |
|---|---|
| WT | 100 |
| H101A | 51 |
| E103A | 71 |
| R113A | 28 |
| T116A | 114 |
| A118S | 102 |
| T127A | 113 |
| S227A | 66 |
| E228A | 80 |
| F229A | 99 |
| Y230A | 1 |
| E266A | 112 |
| R287A | 66 |
| E305A | 97 |
| L419A | 50 |
| K420A | 23 |
| D423A | <1 |
| R424A | <1 |
| K427A | <1 |
| T428A | 81 |

Hot-Spot Residues for mAb1-6723

Hot-spot residues for mAb1-6723 are defined as positions where substitution of the wild-type residue with alanine (or for position 118 substitution of alanine with serine) reduces the binding of the antibody to 30% or less relative to binding of the antibody to wild-type FX at a concentration of 5 μM of WT (or variant) desGLA-desEGF1-FX.

Hot-spot residues for mAb1-6723 (experimentally represented by its monovalent counterpart, mAb 4-6934): R113, Y230, K420, D423, R424 and K427

Example 15: Identification of Hot-Spot Residues on FIX/FIXa

In order to determine residues critical for the interaction (referred to as hot-spot) between the anti-FIX/FIXa Abs, mAb0-1886, mAb0-1998 and mAb1-1307 and FIX, a set of FIX variants was selected based on the crystal structure of FIXa in complex with the corresponding Fab fragments (Fab7237, Fab7238 and Fab7236, respectively). As detailed below the selected FIX variants were transiently expressed in mammalian cells, purified and characterized with respect to their binding to monovalent variants of mAb0-1886, mAb0-1998 and mAb1-1307 using Surface Plasmon Resonance (SPR).

Generation of FIX Mutants

A DNA plasmid, suitable for transient mammalian expression, was constructed with an expression cassette encoding amino acids residues 1-461 of human FIX (uniprot P00740, except for a T194A mutation according to the UNIPROT numbering, corresponding to T148A of SEQ ID NO:1) directly followed by six Histidines (6×His-tag, for affinity purification). The secreted, mature FIX protein chain produced using this construct is identical to the A148 allelic form of human FIX (Anson et al. EMBO J. 1984 3:1053-1060, McGraw et al, Proc Natl Acad Sci USA. 1985 82:2847-2851) except for the addition of the C-terminal His-tag.

Using the construct as template, selected mutations were introduced by PCR. For each single-point mutation listed in Table 11, a forward primer containing the desired amino acid change and a reverse primer without amino acid mutations were designed. These primers were used in a standard PCR reaction with the vector described above as template to amplify the entire vector sequence. Ligation-free cloning was used to join the ends of the resulting amplified DNA fragment into a circular expression plasmid using overlap sequences introduced by the forward and the reverse primers.

The circularized plasmids were transformed into E. coli cells, grown on selective agar plates to form colonies, and the colonies used to start liquid E. coli cultures. After overnight growth of the E. coli cultures, plasmid preparations were performed and the mutants identified by DNA sequencing.

Recombinant protein production was performed by transfecting expi293F cells growing in suspension culture in Expi293 Expression™ medium (ThermoFisher Scientific, cat #A1435101) using the ExpiFectamine™ 293 Transfection Kit (ThermoFisher Scientific, cat #A14525) and plasmid DNA encoding each of the desired variants as well as wild-type FIX (corresponding to SEQ ID NO:1 with C-terminal His-tag). Vitamin K was added to a final concentration of 5 mg/mL at the time of transfection. Transfection Enhancers 1 and 2 from the ExpiFectamine™ 293 Transfection Kit were added the day after transfection. The cell cultures were harvested 5 days after transfection by centrifugation.

The C-terminal His-tag on each FIX variant was used for batch protein purification in a multi-well, robotic setup. Briefly, the harvested cell culture supernatants were adjusted to binding conditions, mixed with Ni Sepharose 6 Fast Flow affinity purification resin (GE Healthcare, cat #17-5318-02, 50 μl sedimented resin/ml cell culture medium) and incubated while shaking for 20 minutes. The resin/supernatant mixes were then transferred to a filter plate and the liquid drawn through the filter plate by application of vacuum. The resin remaining in the filter plate was washed three times before elution in a high-imidazole buffer.

Concentration determination of the purified protein solutions was performed by ELISA, using an anti-FIX antibody for detection and high-purity recombinant wild-type FIX for standard curves.

TABLE 11

List of generated FIX mutants

| Position[1] | Mutation | Domain[2] |
|---|---|---|
| 84 | L84K | EGF2 |
| 84 | L84M | EGF2 |
| 84 | L84E | EGF2 |
| 85 | D85Q | EGF2 |
| 85 | D85K | EGF2 |
| 85 | D85N | EGF2 |
| 87 | T87E | EGF2 |
| 87 | T87I | EGF2 |
| 89 | N89M | EGF2 |
| 89 | N89Q | EGF2 |
| 90 | I90Y | EGF2 |
| 90 | I90A | EGF2 |
| 101 | N101D* | EGF2 |
| 102 | S102A | EGF2 |
| 102 | S102E | EGF2 |
| 102 | S102R | EGF2 |
| 256 | H256F | PD |
| 256 | H256A | PD |
| 257 | H257F | PD |
| 257 | H257A | PD |
| 258 | N258Q | PD |
| 258 | N258A | PD |
| 263 | I263A | PD |
| 292 | D292N | PD |
| 292 | D292S | PD |
| 293 | K293A | PD |
| 294 | E294A | PD |
| 294 | E294Q | PD |
| 301 | K301A | PD |
| 330 | L330A | PD |
| 331 | V331A | PD |
| 331 | V331I | PD |
| 332 | D332A | PD |
| 332 | D332S | PD |
| 333 | R333A | PD |
| 334 | A334L | PD |
| 335 | T335A | PD |
| 337 | L337A | PD |
| 338 | R338A | PD |
| 339 | S339L | PD |
| 339 | S339A* | PD |
| 340 | T340A | PD |
| 341 | K341A | PD |
| 341 | K341E | PD |
| 342 | F342A | PD |
| 343 | T343I | PD |
| 343 | T343A | PD |
| 346 | N346A | PD |
| 346 | N346Q | PD |
| 354 | H354Y | PD |
| 354 | H354A | PD |
| 392 | K392E | PD |
| 392 | K392A | PD |
| 392 | D292A | PD |
| 393 | G393I | PD |
| 395 | Y395A | PD |
| 400 | K400M | PD |
| 400 | K400A | PD |
| 402 | S402A | PD |
| 403 | R403Q | PD |
| 403 | R403A | PD |
| 404 | Y404A* | PD |
| 404 | Y404F | PD |
| 405 | V405A | PD |
| 406 | N406Q | PD |
| 406 | N406A | PD |

TABLE 11-continued

List of generated FIX mutants

| Position[1] | Mutation | Domain[2] |
|---|---|---|
| 410 | E410Q | PD |
| 411 | K411A | PD |

[3] According to SEQ ID NO: 1
[4] EGF2 and PD refer to second epidermal growth factor-like and protease domains, respectively
*Variants marked with an asterisk exhibited very low expression levels and could not be assessed in binding studies Thermal stability of FIX variants To test if introduction of the amino acid substitutions in the FIX variants lead to destabilization and improper folding, the midpoint ($T_m$) of the thermal unfolding transition was determined for the variants.

Purified FIX variants were loaded into standard capillaries (Prometheus NT.48 nanoDSF Grade Standard capillaries, Nanotemper Technologies GmbH, München) and inserted in to the Prometheus NT.48 (Nanotemper Technologies GmbH, München). An excitation intensity of 70% was used and thermal unfolding was followed from 20-90° C. with a heating ramp of 1.5° C./min. Tryptophan fluorescence was measured by excitation at 280 nm and recording emission at 330 nm and 350 nm. $T_m$ of the FIX variants could be determined (except where the protein concentration was below 20 μg/mL, which was the case for FIX N101 D, H256A, L330A S339A, G3931, Y404A and N406Q) from the ratio of fluorescence measured at 350 nm and 330 nm (F350/F330). In all cases, the program PR.ThermControl v2.0.4 (NanoTemper Technologies GmbH, München) could automatically fit $T_m$ by determining the maximum of the first derivative of the F350/F330 unfolding curve. $T_m$ for wild-type FIX was found to be 51° C. and $T_m$ for the variants ranged from 47 to 54° C. demonstrating that no major destabilization was induced by the amino acid substitutions.

SPR Analysis

The FIX variants were characterized with respect to their binding to mAb0-1886, mAb0-1998 and mAb1-1307 using surface plasmon resonance (SPR) by capturing the FIX variant via the C-terminal His-tag. To avoid potential avidity effects associated with a conventional bivalent antibody, i.e. ensure a 1:1 interaction, monovalent variants of mAb0-1886, mAb0-1998 and mAb1-1307, denoted mAb4-0673, mAb4-0004 and mAb3-3279, respectively (prepared as described in Example 7), were used as analytes.

SPR analyses were carried out on Biacore 4000 or Biacore T200 instruments (Biacore AB, Uppsala, Sweden). For the experiments on the T200 instrument the following conditions were applied: measurements were conducted at a temperature of 25° C. Anti-His antibody at 25 μg/ml (R&D Systems, catalogue #MAB050) was immobilized on a CM5 sensor chip using standard amine coupling chemistry. Anti-FIX variants at 25 nM were injected at a flow rate of 10 μl/min for 1 min and were captured via their His-tag by the immobilized anti-His antibody.

Subsequently, 200 nM (with 4-fold serial dilutions), 1600 nM (with 3-fold serial dilutions), and 2000 nM (with 3-fold serial dilution) of mAb4-0004, mAb3-3279 and mAb4-0673, respectively, were injected at a flow rate of 50 μl/min for 5 min to allow for binding to captured FIX variant followed by a 10 min buffer injection allowing for dissociation of the monovalent anti-FIX antibodies. The running buffer used was 20 mM Tris, 150 mM NaCl, 5 mM $CaCl_2$, 0.05% Tween-20, 1 mg/ml BSA, pH 7.4. This was also used for dilution of anti-FIX antibody and FIX samples. Regeneration of the chip was achieved using 10 mM Glycine pH 2.0. Binding data were analysed according to a 1:1 model using BiaEvaluation 4.1 supplied by the manufacturer (Biacore AB, Uppsala, Sweden). A similar experimental set-up was used for the Biacore 4000 instrument.

Initially all FIX variants listed in table 11 were screened using the Biacore 4000 instrument for binding to all three monovalent antibodies, mAb4-0004, mAb3-3279 and mAb4-0673. Binding of the antibodies to FIX variants comprising mutations in positions corresponding to their respective epitope residues (defined by a distance criterion as outlined in example 6) were, as expected, to variable extent perturbed. No significant impact on antibody binding was observed for FIX variants comprising mutations in position not corresponding to their respective epitope residues. In particular, none of the substitutions made in the EGF2 domain had any influence on binding to any of the antibodies (data not shown). A more detailed binding analysis was conducted for residues defined as epitope residues (see example 6) using the Biacore T200 instrument. Results are given in table 12.

Binding data are reported as % binding of the antibody to the FIX variant relative to binding of the antibody to wild-type FIX calculated according to the formula:

$$\text{Binding (\%)} = 100\% \times [(R_{max\_Ab,FIX\_var})/(R_{max\_FIXvar})]/[(R_{max\_Ab,FIX\_wt})/(R_{max\_FIXwt})]$$

where $R_{max\_FIXvar}$ and $R_{max\_FIXwt}$ represent capture level (RU) of FIX variant and wild-type FIX, respectively, and where $R_{max\_Ab,FIX\_var}$ and $R_{max\_Ab,FIX\_wt}$ represent binding (RU) of the antibody to captured FIX variant and wild-type FIX, respectively. Results are shown in table 12.

TABLE 12

Results from SPR analysis
Results from SPR analysis of mAb3-3279, mAb4-0004, and mAb4-0673 (monovalent variants of mAb1-1307, mAb0-1998 and mAb0-1886, respectively) binding to selected FIX variants covering epitope residues for mAb1-1307, mAb0-1998 and mAb0-1886.

| Lineage | Position | Variant | Antibody | Binding (%) |
|---|---|---|---|---|
| 1-1307 | 256 | H256A | mAb3-3279 | 32 |
| 1-1307 | 257 | H257A | mAb3-3279 | 8 |
| 1-1307 | 258 | N258A | mAb3-3279 | 82 |
| 1-1307 | 293 | K293A | mAb3-3279 | 23 |
| 1-1307 | 403 | R403A | mAb3-3279 | 94 |
| 1-1307 | 404 | Y404F | mAb3-3279 | 76 |
| 1-1307 | 406 | N406A | mAb3-3279 | 12 |
| 1-1307 | 410 | E410Q | mAb3-3279 | 39 |
| 1-1307 | 411 | K411A | mAb3-3279 | 71 |
| 1-1307 | WT | WT | mAb3-3279 | 100 |
| 0-1998 | 301 | K301A | mAb4-0004 | 66 |
| 0-1998 | 332 | D332S | mAb4-0004 | 66 |
| 0-1998 | 332 | D332A | mAb4-0004 | 50 |
| 0-1998 | 333 | R333A | mAb4-0004 | 66 |
| 0-1998 | 334 | A334L | mAb4-0004 | 51 |
| 0-1998 | 335 | T335A | mAb4-0004 | 62 |
| 0-1998 | 337 | L337A | mAb4-0004 | 52 |
| 0-1998 | 338 | R338A | mAb4-0004 | 2 |
| 0-1998 | 339 | S339L | mAb4-0004 | 66 |
| 0-1998 | 340 | T340A | mAb4-0004 | 37 |
| 0-1998 | 341 | K341E | mAb4-0004 | 2 |
| 0-1998 | 341 | K341A | mAb4-0004 | 21 |
| 0-1998 | 343 | T343I | mAb4-0004 | 48 |
| 0-1998 | 343 | T343A | mAb4-0004 | 38 |
| 0-1998 | 346 | N346A | mAb4-0004 | 73 |
| 0-1998 | WT | WT | mAb4-0004 | 100 |
| 0-1886 | 301 | K301A | mAb4-0673 | 93 |
| 0-1886 | 332 | D332A | mAb4-0673 | 17 |
| 0-1886 | 333 | R333A | mAb4-0673 | 4 |
| 0-1886 | 334 | A334L | mAb4-0673 | 44 |
| 0-1886 | 335 | T335A | mAb4-0673 | 71 |
| 0-1886 | 337 | L337A | mAb4-0673 | 7 |
| 0-1886 | 338 | R338A | mAb4-0673 | 3 |
| 0-1886 | 339 | S339L | mAb4-0673 | 73 |
| 0-1886 | 340 | T340A | mAb4-0673 | 67 |
| 0-1886 | 341 | K341E | mAb4-0673 | 53 |
| 0-1886 | 341 | K341A | mAb4-0673 | 96 |
| 0-1886 | 343 | T343I | mAb4-0673 | 90 |
| 0-1886 | 343 | T343A | mAb4-0673 | 63 |
| 0-1886 | 346 | N346Q | mAb4-0673 | 94 |
| 0-1886 | 346 | N346A | mAb4-0673 | 51 |
| 0-1886 | WT | WT | mAb4-0673 | 100 |

1) Position according to SEQ ID NO: 1
2) 100% × [($R_{max\_Ab, FIX\_var}$)/($R_{max\_FIXvar}$)]/[($R_{max\_Ab, FIX\_wt}$)/($R_{max\_FIXwt}$)]

Hot-Spot Residues mAb1-1307, mAb0-1998 and mAb0-1886

Hot-spot residues for mAb1-1307, mAb0-1998 and mAb0-1886 are defined as positions were substitution of the wild-type residue with alanine reduces the binding of the antibody to 30% or less relative to binding of the antibody to wild-type FIX.

Hot-spot residues for mAb1-1307 (experimentally represented by mAb3-3279): H257, K293 and N406

Hot-spot residues for mAb0-1998 (experimentally represented by mAb4-0004): R338 and K341

Hot-spot residues for mAb0-1886 (experimentally represented by mAb4-0673): D332, R333, L337 and R338

For both mAb0-1998 and mAb0-1886 the residue contributing most to binding is R338; substitution of R338 with alanine (R338A) in FIX exhibited the largest impact on antibody binding, which was greatly reduced to 2% and 3% for mAb0-1998 and mAb0-1886, respectively, relative to antibody binding to wild-type FIX.

Example 16: Activity of Anti-FIX(a)/FX(a) Bispecific Antibodies in a FXa Generation Assay The procoagulant activity of anti-FIXa/FX bispecific antibodies was determined based on their ability to promote FX activation by FIXa in the presence of a procoagulant phospholipid membrane. The bispecific antibodies (BiAb) tested are listed in table 13 and ACE910 was included for comparison.

The procoagulant activity of each bispecific antibody is reported as fold stimulation relative to FX activation by free FIXa at a given antibody concentration. Bispecific antibodies were tested at 8 concentrations (made by serial three-fold dilutions in assay buffer) by pre-incubation with 125 pM human plasma-derived FIXa (Haematologic Technologies Inc, USA) and 500 µM 25:75 phosphatidyl serine:phosphatidyl choline phospholipid vesicles (Haematologic Technologies Inc, USA) in assay buffer (50 mM HEPES, 100 mM NaCl, 5 mM $CaCl_2$, 0.1% (w/v) PEG8000, pH 7.3+1 mg/ml BSA) for 10 min. Activation was then initiated by addition of human plasma-derived FX (Haematologic Technologies Inc, USA) to a concentration of 25 nM. Following 15 min activation at room temperature, the reaction (50 µl)

was quenched by addition of 25 µl quench buffer (50 mM HEPES, 100 mM NaCl, 60 mM EDTA, 0.1% PEG8000, pH 7.3+1 mg/ml BSA). The amount of FXa generated was determined by addition of 25 µl 2 mM S-2765 chromogenic substrate (Chromogenix, Sweden) and measurement of chromogenic substrate conversion by absorbance measurement at 405 nm (AOD/min) in a microplate reader. Similarly, FX activation by free FIXa was determined at a FIXa concentration of 25 nM and a reaction time of 60 min. The measured activity was normalized according to the concentration of FIXa present in the assay and the reaction time. By dividing this number by the similarly normalized rate of FXa generation in the absence of antibody, fold stimulation by the antibody at a given concentration was calculated.

In summary, calculation of biAb stimulation can be described as follows

BiAb stimulation=$(A_{FIXa+biAb}/([FIXa]_{assay} \times t_{reaction}))/ A_{FIXa,norm}$ where $A_{FIXa+biAb}$ is the activity measured in the presence of bispecific antibody, $[FIXa]_{assay}$ is the FIXa concentration in the assay, $t_{reaction}$ is the reaction time, and $A_{FIXa,norm}$ is the normalized activity of free FIXa.

Table 13 lists the maximum stimulation determined for each bispecific antibody among the 8 antibody concentrations tested as well as the concentration at which maximum stimulation was observed. For all tested bispecific antibodies the maximum stimulation was found to be higher than that measured for ACE910, which was tested at a concentration interval from 0 to 15300 nM.

TABLE 13

Maximum stimulation by bispecific anti-FIXa/FX antibodies

| BiAb antibody ID | FIXa antibody ID (lineage) | FX antibody ID (lineage) | Concentration span tested (nM) | BiAb conc at maximum stimulation (nM) | Maximum stimulation (fold) |
|---|---|---|---|---|---|
| ACE910 | | | 7.5-15300 | 15300 | 808 |
| 5-0057 | 1-8768 (0-1998) | 1-6723 (1-6723) | 1.7-3654 | 1218 | 10754 |
| 5-1409 | 1-8768 (0-1998) | 1-7503 (1-6723) | 1.5-3346 | 1115 | 11041 |
| 4-7687 | 1-6037 (0-1998) | 1-6723 (1-6723) | 1.6-3300 | 1650 | 2493 |
| 4-7756 | 1-6584 (0-1886) | 1-6723 (1-6723) | 0.7-1520 | 1520 | 2597 |
| 4-7758 | 1-6584 (0-1886) | 1-6097 (1-2375) | 0.6-1266 | 633 | 2807 |
| 4-7762 | 1-6584 (0-1886) | 1-6738 (1-2375) | 0.1-109.2 | 109 | 3194 |
| 4-7786 | 1-6081 (0-1998) | 1-6463 (1-2375) | 2.0-4060 | 4060 | 1267 |
| 4-7789 | 1-6584 (0-1886) | 1-6463 (1-2375) | 1.0-2020 | 253 | 3529 |
| 4-5925 | 1-4857 (0-1998) | 1-6723 (1-6723) | 0.7-1600 | 533 | 5195 |

Example 17: Activity of Bispecific Anti-FIX(a)/FX(a) Antibodies in a Thrombin Generation Test (TGT) in Human Haemophilia a Platelet-Poor and Platelet-Rich Mimic Plasma The procoagulant activity of the bispecific antibodies mAb4-7761, mAb4-7762, mAb4-7789, mAb5-0057, and mAb5-1409 (see Table 14) was determined based on their ability to promote thrombin generation in the presence of either a procoagulant synthetic phospholipid membrane or platelets according to the principles described by Hemker et al. (Pathophysiol Haemost Thromb, 2002; 32:249-253). ACE910 was included for comparison. Each antibody (test compound) was tested in a thrombin generation test (TGT) in Haemophilia A (HA) patient pooled platelet-poor plasma (HA-PPP) and/or HA-induced human platelet-rich plasma (HA-PRP).

TABLE 14

Bispecific anti-FIX(a)/FX(a) antibodies

| BiAb antibody ID | Anti-FIX antibody ID (lineage) | Anti-FX antibody ID (lineage) |
|---|---|---|
| 4-7761 | 1-5743 (0-1886) | 1-6738 (1-2375) |
| 4-7762 | 1-6584 (0-1886) | 1-6738 (1-2375) |
| 4-7789 | 1-6584 (0-1886) | 1-6463 (1-2375) |
| 5-0057 | 1-8768 (0-1998) | 1-6723 (1-6723) |
| 5-1409 | 1-8768 (0-1998) | 1-7503 (1-6723) |

Haemophilia A-Induced Human Platelet-Rich Plasma (HA-PRP)

Blood was obtained from healthy consenting donors by venipuncture. Six volumes of blood was collected into 1 volume acid citrate dextrose (ACD; 85 mM sodium citrate, 110 mM dextrose, and 62.3 mM citric acid, pH 4.9), final pH 6.5, and centrifuged for 20 min at 220 g at room temperature (RT). Platelet-rich plasma (PRP) was collected and platelet concentrations were determined with a Medonic CA 620 hematology analyzer (Boule Diagnostics AB, Spanga, Sweden). The red blood cells containing plasma part was centrifuged for another 10 min at 600 g at RT. Platelet-poor plasma (PPP) was collected and used to the dilute PRP to 300,000 platelets/µl. HA conditions were induced by addition of a FVIII-neutralising anti-human FVIII antibody (Sheep anti-Human Factor VIII—5 mg, Haematologic Technologies, VT, USA) to a final concentration of 0.1 mg/ml and rotated gently at 2 rpm for 30 minutes at RT.

Thrombin Generation Test

Thrombin generation tests (TGT) in HA-PRP and HA-PPP (George King Bio-Medical Inc, KS, USA) were performed by standard calibrated automated thrombography using a 96-well plate fluorometer (Fluoroscan Ascent FL, Thermolabsystems, Helsinki, Finland). Reaction mixtures contained 70 µl HA-PRP (300,000 platelets/µl) or HA-PPP, 10 µl test compound dilution (diluted in 20 mM HEPES, 140 mM NaCl, pH 7.4, 2% BSA), 20 µl CAT reagents containing tissue factor (TF) (PRP reagent; TF without synthetic phospholipids, PPP-reagent LOW; TF with synthetic phospholipids, 1 µM TF final, Thrombinoscope BV, Maastricht, the Netherlands) or Thrombin Calibrator (Thrombinoscope BV), and 20 µl of a mixture containing the fluorescently labelled thrombin substrate z-Gly-Gly-Arg-AMC (3 mM) and $CaCl_2$ (90 mM) (Thrombinoscope BV). TGT was performed at up to eight concentrations of test compound (0.3, 1.0, 3, 10, 30, 100, 300, and 900 nM, final plasma concentration) or added buffer (20 mM HEPES, 140 mM NaCl, pH 7.4, 2% BSA) only (representing HA control). The concentration ranges were tested in at least three independent experiments in HA-PPP from the same stock or in blood from four different donors. Normal control levels in TGT were measured using untreated human PRP or CRYOcheck™ pooled normal human PPP plasma (Precision Biologic Inc., Dartmouth, Canada) added buffer (20 mM HEPES, 140 mM NaCl, pH 7.4, 2% BSA) only. The TGT was allowed to proceed for a total of 90 minutes and the TGT parameter Peak Thrombin Height (nM) was analysed by Thrombinoscope software (Thrombinoscope BV).

FIG. 2/Table 15 shows the measured peak thrombin generation rates for each bispecific antibody at the concentrations tested in HA-PPP. The data show that all test compounds increase the peak thrombin formation above the level observed in the absence of antibody, i.e. exhibit procoagulant activity. In addition, thrombin generation levels between 30 and 300 nM for mAb4-7761, mAb4-7762, mAb4-7789, mAb5-0057, and mAb5-1409 are higher than that observed for ACE910, demonstrating to a superior potency. Moreover, thrombin generation levels at 300 to 900 nM of mAb5-0057 and mAb5-1409 are higher than that observed with 900 nM ACE910, demonstrating higher potencies and efficacies of these compounds compared to ACE910.

Figure 3A:
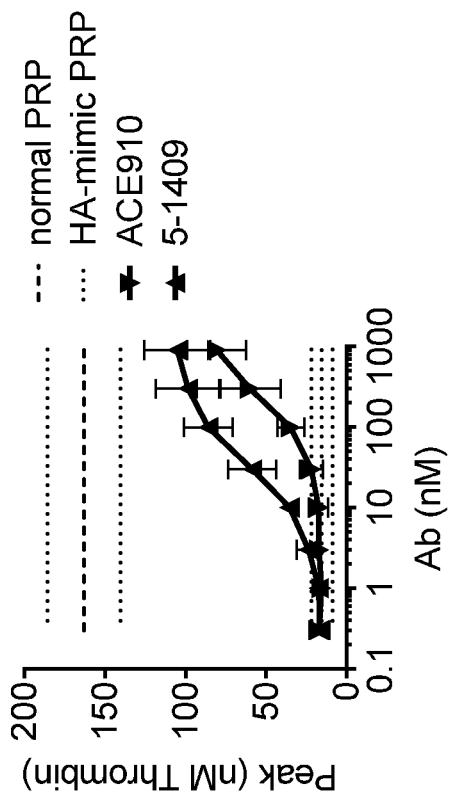
FIG. 3 shows Thrombin generation test (TGT) data from the bispecific antibodies mAb5-0057 (FIG. 3A), mAb5-1409 (FIG. 3B) and ACE910 in human tissue factor activated haemophilia A platelet-rich plasma (HA-PRP). The experiment was performed as described in Example 17. Dotted and stippled lines indicate the peak thrombin level (nM) observed in the absence of anti-FVIII antibody in HA-PRP and normal PRP, respectively, and with their standard deviation indicated by the dotted lines. The profiles of mAb5-0057 (FIG. 3A) and mAb5-1409 (FIG. 3B) are indicated by up-pointing triangles, whereas that of ACE910 is indicated by down-pointing triangles. Results are shown as mean±standard deviation from four independent experiments.
Figure 3B:
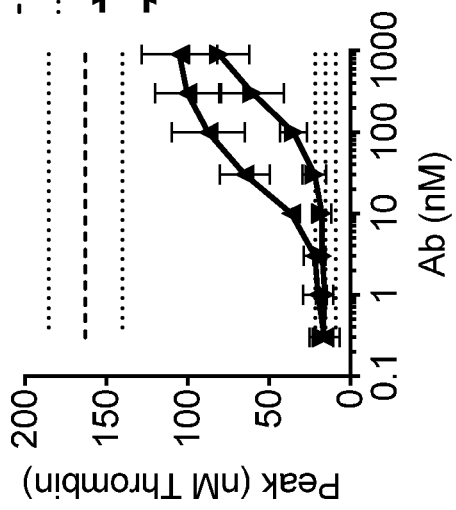

FIG. 3/Table 16 shows the measured peak thrombin generation levels for mAb5-0057 and mAb5-1409 at the concentrations tested in HA-PRP. Under these conditions, mAb5-0057 and mAb5-1409 also display better potencies and efficacies compared to ACE910.

TABLE 15

Thrombin generation test (TGT) of the bispecific antibodies mAb4-7761, mAb47762, mAb4-7789, mAb5-0057, mAb5-1409 and ACE910 Thrombin generation test (TGT) of the bispecific antibodies mAb4-7761, mAb4-7762, mAb4-7789, mAb5-0057, mAb5-1409 and ACE910 in human tissue factor activated haemophilia A platelet-poor plasma (PPP). Mean peak thrombin generation levels ± standard deviation measured at each of the tested compound concentrations in at least three independent experiments in HA-PPP. Exp. A-D refers to independent experiments as described in the FIG. 2 legend.

| Exp. A Compound concentration (nM) | Peak thrombin (mean ± SD in nM) for ACE910 | Peak thrombin (mean ± SD in nM) for mAb4-7761 |
|---|---|---|
| 0 | 19.4 ± 2.3 | 19.4 ± 2.3 |
| 0.3 | 17.2 ± 0.4 | 18.1 ± 2.4 |
| 1 | 18.3 ± 1.4 | 18.9 ± 0.9 |
| 3 | 17.9 ± 2.1 | 21.8 ± 3.7 |
| 10 | 19.3 ± 1.0 | 22.4 ± 1.6 |
| 30 | 20.5 ± 2.3 | 34.0 ± 1.9 |
| 100 | 24.6 ± 2.0 | 51.7 ± 3.7 |
| 300 | 35.9 ± 3.0 | 57.9 ± 1.4 |
| 900 | 54.0 ± 4.7 | |

| Exp. B Compound concentration (nM) | Peak thrombin (mean ± SD in nM) for ACE910 | Peak thrombin (mean ± SD in nM) for mAb4-7762 |
|---|---|---|
| 0 | 8.5 ± 1.2 | 8.5 ± 1.2 |
| 0.3 | 7.7 ± 1.0 | 8.5 ± 1.1 |
| 1 | 7.8 ± 1.0 | 8.9 ± 0.8 |
| 3 | 8.3 ± 1.2 | 9.1 ± 1.2 |
| 10 | 9.8 ± 2.2 | 10.6 ± 0.9 |
| 30 | 9.6 ± 1.0 | 16.4 ± 0.5 |
| 100 | 13.6 ± 1.1 | 31.8 ± 7.0 |
| 300 | 19.5 ± 4.7 | 38.1 ± 0.8 |
| 900 | 39.0 ± 3.1 | |

| Exp. C Compound concentration (nM) | Peak thrombin (mean ± SD in nM) for ACE910 | Peak thrombin (mean ± SD in nM) for mAb4-7789 |
|---|---|---|
| 0 | 7.4 ± 0.1 | 7.4 ± 0.1 |
| 0.3 | 6.6 ± 0.6 | 7.9 ± 0.5 |
| 1 | 8.6 ± 2.1 | 8.0 ± 1.1 |
| 3 | 7.1 ± 0.5 | 8.6 ± 0.5 |
| 10 | 9.2 ± 2.2 | 10.6 ± 0.8 |
| 30 | 9.5 ± 0.9 | 18.6 ± 4.5 |
| 100 | 12.1 ± 1.5 | 28.2 ± 1.4 |
| 300 | 20.7 ± 7.9 | 31.5 ± 1.9 |
| 900 | 34.5 ± 3.4 | 19.5 ± 1.2 |

| Exp. D Compound concentration (nM) | Peak thrombin (mean ± SD in nM) for ACE910 | Peak thrombin (mean ± SD in nM) for mAb5-0057 | Peak thrombin (mean ± SD in nM) for 51409 |
|---|---|---|---|
| 0 | 20.7 ± 7.8 | 20.7 ± 7.8 | 20.7 ± 7.8 |
| 0.3 | 26.6 ± 13.2 | 21.7 ± 7.9 | 18.3 ± 7.1 |
| 1 | 21.3 ± 8.9 | 24.5 ± 8.5 | 20.1 ± 8.7 |
| 3 | 23.4 ± 9.9 | 28.7 ± 1.8 | 23.2 ± 10.1 |
| 10 | 25.6 ± 8.6 | 31.2 ± 11.3 | 22.6 ± 5.5 |
| 30 | 26.4 ± 9.3 | 42.9 ± 13.9 | 32.2 ± 12.7 |
| 100 | 32.0 ± 9.9 | 82.6 ± 23.4 | 68.5 24.5 |
| 300 | 46.1 ± 12.3 | 112.3 ± 29.0 | 99.5 27.3 |
| 900 | 71.6 ± 18.4 | 119.7 ± 26.7 | 104.0 30.2 |

TABLE 16

Thrombin generation test (TGT) of the bispecific
antibodies mAb5-0057, mAb5-1409 and ACE910
Thrombin generation test (TGT) of the bispecific
antibodies mAb5-0057, mAb5-1409 and ACE910 in human
tissue factor activated haemophilia A platelet-rich
plasma (PRP). Mean peak thrombin generation ±
standard deviation at each of the tested compound
concentrations from four independent experiments in HA-PRP.

| Compound concentration (nM) | Peak thrombin (mean ± SD in nM) for ACE910 | Peak thrombin (mean ± SD in nM) for mAb5-0057 | Peak thrombin (mean ± SD in nM) for mAb5-1409 |
|---|---|---|---|
| 0 | 15.5 ± 6.6 | 15.5 ± 6.6 | 15.5 ± 6.6 |
| 0.3 | 17.2 ± 7.7 | 16.1 ± 9.2 | 17.2 ± 6.6 |
| 1 | 15.7 ± 5.3 | 19.9 ± 11.4 | 17.4 ± 5.6 |
| 3 | 17.5 ± 6.4 | 21.8 ± 6.5 | 23.7 ± 8.7 |
| 10 | 17.6 ± 6.4 | 36.4 ± 4.9 | 35.6 ± 4.5 |
| 30 | 22.1 ± 6.5 | 65.0 ± 7.1 | 58.8 ± 5.2 |
| 100 | 34.9 ± 9.9 | 87.4 ± 25.3 | 86.0 ± 10.5 |
| 300 | 60.3 ± 16.1 | 100.4 ± 17.6 | 98.6 ± 18.8 |
| 900 | 80.7 ± 11.0 | 105.3 ± 23.8 | 105.3 ± 21.9 |

Figure 4:
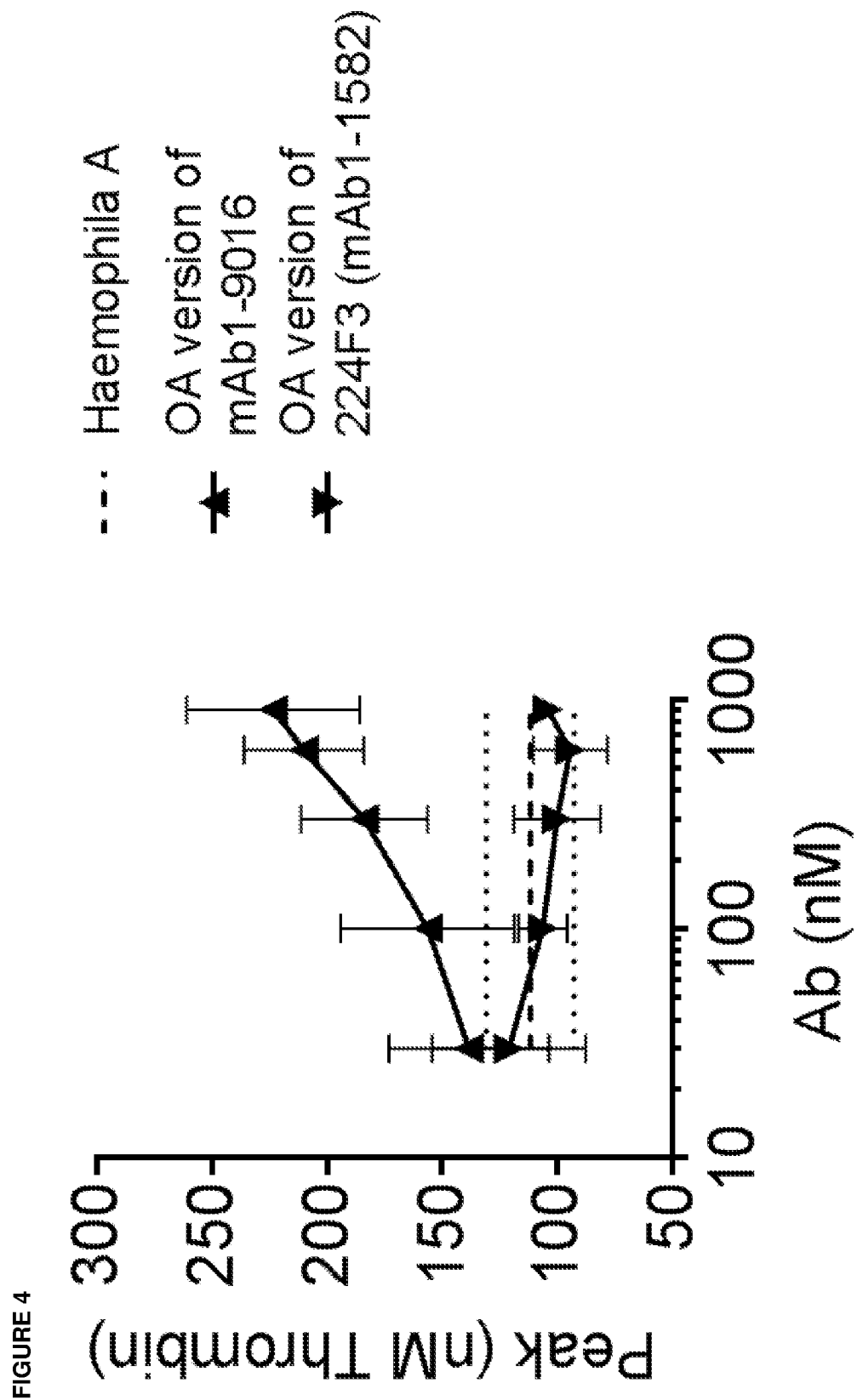
FIG. 4 shows Thrombin generation test (TGT) data from the monovalent one-armed (OA) antibodies of mAb1-9016 and 224F3 in human Factor XIa activated platelet-poor plasma. The experiment was performed as described in Example 18. Stippled lines indicate the average peak thrombin level (nM) observed in the absence of antibody and with its standard deviation (±1 SD) indicated by dotted lines. The profiles of OA versions of mAb1-9016 and 224F3 (mAb1-1582) are indicated by up-pointing and down-pointing triangles, respectively.

Example 18: Activity of Monovalent One-Armed (OA) Anti-FIX/FIXa Antibodies in a Thrombin Generation Test (TGT) in Human Haemophilia a Platelet-Poor Plasma The procoagulant activity of the monovalent one-armed (OA) version of mAb1-9016 was determined based on its ability to promote thrombin generation in the presence of a procoagulant phospholipid membrane according to the principles described by Hemker et al. (2002) Pathophysiol Haemost Thromb, 32:249-253. The one-armed version of the 224F3 antibody (mAb1-1582) was included for comparison. Each antibody (test compound) was tested in a thrombin generation test (TGT) in haemophilia A (HA) patient pooled platelet-poor plasma (HA-PPP) (George King Bio-Medical Inc, KS, USA) by standard calibrated automated thrombography using a 96-well plate fluorometer (Fluoroscan Ascent FL, Thermolabsystems, Helsinki, Finland). Reaction mixtures contained 70 µl HA-PPP, 10 µl test compound (diluted in 20 mM HEPES, 140 mM NaCl, pH 7.4, 2% BSA), 20 µl PRP reagents (synthetic phospholipids, Thrombinoscope BV, Maastricht, the Netherlands) containing activated human plasma-derived factor XI (hFXIa, 8.3 mU/mL final) (Enzyme Research Laboratories, IN, USA) or Thrombin Calibrator (Thrombinoscope BV), and 20 µl of a mixture containing the fluorescent labelled thrombin substrate Z-Gly-Gly-Arg-AMC (3 mM) and $CaCl_2$ (90 mM) (Thrombinoscope BV). TGT was performed at five concentrations of test compound (30, 100, 300, 600 and 900 nM, final plasma concentration) or added buffer (20 mM HEPES, 140 mM NaCl, pH 7.4, 2% BSA) only (representing HA control). The concentration range was tested in two independent experiments in HA-PPP from the same stock. The TGT was allowed to proceed for a total of 90 minutes and the TGT parameter Peak Thrombin Height (nM) was analysed by Thrombinoscope software (Thrombinoscope BV). FIG. 4 and Table 17 shows/lists the measured peak thrombin generation rates for each monovalent one-armed antibody at the concentrations tested. The data show that the OA antibody version of mAb1-9016 increases the peak thrombin formation above the level observed in the absence of antibody, i.e. exhibit procoagulant activity. In addition, thrombin generation induced by the OA antibody version of mAb1-9016 is higher than that observed for the monovalent OA version of the 224F3 antibody (mAb1-1582).

TABLE 17

Measured peak thrombin generation rates
for each monovalent one-armed antibody at the
concentrations tested. Listed is the average
peak thrombin ± standard deviation of
two independent experiments in HA-PPP

| Compound concentration (nM) | Peak thrombin (mean ± SD in nM) for OA of 224F3 (mAb1-1582) | Peak thrombin (mean ± SD in nM) for OA of mAb1-9016 |
|---|---|---|
| 0 | 111.6 ± 19.0 | 111.6 ± 19 |
| 30 | 121.0 ± 33.5 | 138.5 ± 34.9 |
| 100 | 106.2 ± 10.7 | 156.4 ± 37.8 |
| 300 | 100.1 ± 18.9 | 184.0 ± 27.7 |
| 600 | 94.4 ± 16.1 | 210.2 ± 26.1 |
| 900 | 104.0 ± 2.7 | 223.5 ± 37.7 |

Example 19: Binding Affinities Determined by Isothermal Titration Calorimetry (ITC)

Binding affinities for anti-FIX/FIXa and anti-FX/FXa antibodies binding to FIX/FIXa and FX/FXa, respectively, are measured by isothermal titration calorimetry (ITC) by using a PEAQ-ITC calorimeter (Malvern, UK). The experiments are conducted at 37° C. and pH 7.4 using 25 mM Tris, 150 mM NaCl, 5 mM $CaCl_2$ (Tris-buffer). The sample cell (200 µl) contains either FIX, FIXa, FX or FXa and anti-FIX/FIXa and anti-FX/FXa antibodies are injected via the syringe. All proteins are extensively dialyzed in Tris-buffer prior to measurements to secure matched buffer conditions. A thermal equilibration step was followed by a 60-s delay and subsequently an initial 0.2-µl injection of antibody, followed by 14 injections of 2.5 µl of antibody at an interval of 120 s. The stirring speed is maintained at 750 rpm, and the reference power is kept constant at 5-10 µcal/s. The heat associated with each injection of antibody is integrated and plotted against the molar ratio of ligand to macromolecule. The resulting isotherm is fitted to a one-site binding model to obtain the affinity (KD), stoichiometry (n), and enthalpy of interaction (ΔH) using the software provided by the manufacturer. Experiments were performed in duplicated or triplicate.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A multispecific antibody or antigen-binding fragment thereof capable of stimulating the enzymatic activity of FIXa towards FX comprising a first antigen-binding site capable of binding to FIX (SEQ ID NO:1) and/or the activated form thereof (FIXa), and a second antigen-binding site capable of binding to FX (SEQ ID NO:2) and/or the activated form thereof (FXa), comprising
   a. the CDR sequences of the anti-FIX/FIXa antibody heavy chain variable domain identified by SEQ ID NO:177 and the CDR sequences of the anti-FIX/FIXa antibody light chain variable domain identified by SEQ ID NO:178, and the CDR sequences of the anti-FX/FXa heavy chain variable domain identified by SEQ ID NO:179 and the CDR sequences of the anti-FX/FXa light chain variable domain identified by SEQ ID NO:180,
   b. the CDR sequences of the anti-FIX/FIXa antibody heavy chain variable domain identified by SEQ ID NO:181 and the CDR sequences of the anti-FIX/FIXa antibody light chain variable domain identified by SEQ ID NO:182, and the CDR sequences of the anti-FX/FXa heavy chain variable domain identified by SEQ ID NO:183 and the CDR sequences of the anti-FX/FXa light chain variable domain identified by SEQ ID NO:184, or
   c. the CDR sequences of the anti-FIX/FIXa antibody heavy chain variable domain identified by SEQ ID NO:187 and the CDR sequences of the anti-FIX/FIXa antibody light chain variable domain identified by SEQ ID NO:188, and the CDR sequences of the anti-FX/FXa heavy chain variable domain identified by SEQ ID NO:185 and the CDR sequences of the anti-FX/FXa light chain variable domain identified by SEQ ID NO:186.

2. The multispecific antibody or antigen-binding fragment thereof according to claim 1, is a bispecific antibody.

3. A pharmaceutical composition comprising the antibody or antigen-binding fragment thereof according to claim 1.

4. A method of treating a subject suffering from a coagulopathy or blood coagulation disorder, comprising administering to said subject an antibody or antigen-binding fragment thereof according to claim 1, wherein said coagulopathy or blood coagulation disorder is haemophilia A with or without inhibitors.

5. A method of treating a subject suffering from a coagulopathy or blood coagulation disorder, comprising administering to said subject a pharmaceutical composition of claim 3, wherein said coagulopathy or blood coagulation disorder is haemophilia A with or without inhibitors.

* * * * *

SEQUENCE LISTING

<160> NUMBER OF SEQ ID NOS: 202

<210> SEQ ID NO 1

```
<211> LENGTH: 415
<212> TYPE: PRT
<213> ORGANISM: Homo sapiens

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
```

-continued

```
            385                 390                 395                 400
Val Ser Arg Tyr Val Asn Trp Ile Lys Glu Lys Thr Lys Leu Thr
                    405                 410                 415

<210> SEQ ID NO 2
<211> LENGTH: 448
<212> TYPE: PRT
<213> ORGANISM: Homo sapiens

<400> SEQUENCE: 2

Ala Asn Ser Phe Leu Glu Glu Met Lys Lys Gly His Leu Glu Arg Glu
1               5                   10                  15

Cys Met Glu Glu Thr Cys Ser Tyr Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350
```

```
Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
435                 440                 445
```

<210> SEQ ID NO 3
<211> LENGTH: 122
<212> TYPE: PRT
<213> ORGANISM: Homo sapiens

<400> SEQUENCE: 3

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Arg Gly Asp Ile Ile Gly Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
            115                 120
```

<210> SEQ ID NO 4
<211> LENGTH: 107
<212> TYPE: PRT
<213> ORGANISM: Homo sapiens

<400> SEQUENCE: 4

```
Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Phe Leu Ile
            35                  40                  45

Tyr Lys Ala Ser Arg Leu Glu Arg Gly Val Pro Ser Arg Phe Ser Gly
        50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
                100                 105
```

<210> SEQ ID NO 5
<211> LENGTH: 122
<212> TYPE: PRT
<213> ORGANISM: Homo sapiens

<400> SEQUENCE: 5

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Gly Asp Asn Ile Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Glu Arg Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 7
<211> LENGTH: 120
<212> TYPE: PRT
<213> ORGANISM: Homo sapiens

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ser Gly Ile Ser Trp Val Ser Gly Ser Ile Gly Tyr Ala Arg Ser Val

```
                    50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Gly Gln Tyr Asp Glu Asp Ala Gly Met Asp Val Trp Gly Gln
            100                 105                 110

Gly Thr Thr Val Thr Val Ser Ser
        115                 120

<210> SEQ ID NO 8
<211> LENGTH: 106
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Pro Thr Trp Thr
                 85                  90                  95

Phe Gly Gly Gly Thr Lys Val Glu Ile Lys
            100                 105

<210> SEQ ID NO 9
<211> LENGTH: 120
<212> TYPE: PRT
<213> ORGANISM: Homo sapiens

<400> SEQUENCE: 9

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Gly Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Lys Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Gly Gln Tyr Asp Glu Asp Ala Gly Met Asp Val Trp Gly Gln
            100                 105                 110

Gly Thr Thr Val Thr Val Ser Ser
        115                 120

<210> SEQ ID NO 10
<211> LENGTH: 106
<212> TYPE: PRT
```

<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Pro Thr Trp Thr
                85                  90                  95

Phe Gly Gly Gly Thr Lys Val Glu Ile Lys
            100                 105

<210> SEQ ID NO 11
<211> LENGTH: 119
<212> TYPE: PRT
<213> ORGANISM: Homo sapiens

<400> SEQUENCE: 11

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Glu Gly Ala Phe Asp Ile Trp Gly Gln Gly
            100                 105                 110

Thr Met Val Thr Val Ser Ser
        115

<210> SEQ ID NO 12
<211> LENGTH: 112
<212> TYPE: PRT
<213> ORGANISM: Homo sapiens

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Arg Leu Leu His Ser
            20                  25                  30

Thr Gly Tyr Asn Tyr Leu Asn Trp Tyr Leu Gln Lys Pro Gly Gln Ser
        35                  40                  45

Pro Gln Leu Leu Ile Tyr Leu Gly Ser Arg Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu His Ile Pro Tyr Thr Phe Gly Gln Gly Thr Lys Leu Glu Ile Lys
            100                 105                 110

<210> SEQ ID NO 13
<211> LENGTH: 119
<212> TYPE: PRT
<213> ORGANISM: Homo sapiens

<400> SEQUENCE: 13

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Met Ile Asp Pro Thr Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Met Ser Gly Ala Phe Asp Ile Trp Gly Gln Gly
            100                 105                 110

Thr Met Val Thr Val Ser Ser
        115

<210> SEQ ID NO 14
<211> LENGTH: 112
<212> TYPE: PRT
<213> ORGANISM: Homo sapiens

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 15
<211> LENGTH: 122
<212> TYPE: PRT
<213> ORGANISM: Homo sapiens

<400> SEQUENCE: 15

Glu Val Gln Leu Val Glu Ser Gly Gly Gly Leu Val Gln Pro Gly Arg
1               5                   10                  15

```
Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Gly Asp Asn Ile Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 16
<211> LENGTH: 107
<212> TYPE: PRT
<213> ORGANISM: Homo sapiens

<400> SEQUENCE: 16

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 17
<211> LENGTH: 120
<212> TYPE: PRT
<213> ORGANISM: Homo sapiens

<400> SEQUENCE: 17

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Gln Tyr Asp Glu Asp Ala Gly Met Asp Val Trp Gly Gln
            100                 105                 110
```

```
Gly Thr Thr Val Thr Val Ser Ser
            115                 120
```

<210> SEQ ID NO 18
<211> LENGTH: 106
<212> TYPE: PRT
<213> ORGANISM: Homo sapiens

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Pro Thr Trp Thr
                85                  90                  95

Phe Gly Gly Gly Thr Lys Val Glu Ile Lys
            100                 105
```

<210> SEQ ID NO 19
<211> LENGTH: 119
<212> TYPE: PRT
<213> ORGANISM: Homo sapiens

<400> SEQUENCE: 19

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Met Glu Gly Ala Phe Asp Ile Trp Gly Gln Gly
            100                 105                 110

Thr Met Val Thr Val Ser Ser
            115
```

<210> SEQ ID NO 20
<211> LENGTH: 112
<212> TYPE: PRT
<213> ORGANISM: Homo sapiens

<400> SEQUENCE: 20

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Gly Tyr Asn Tyr Leu Asn Trp Tyr Leu Gln Lys Pro Gly Gln Ser
```

```
                35                  40                  45
Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu His Ile Pro Tyr Thr Phe Gly Gln Gly Thr Lys Leu Glu Ile Lys
                100                 105                 110

<210> SEQ ID NO 21
<211> LENGTH: 120
<212> TYPE: PRT
<213> ORGANISM: Homo sapiens

<400> SEQUENCE: 21

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Thr Ser
                 20                  25                  30

Trp Ile Val Trp Val Arg Gln Met Pro Gly Lys Gly Leu Glu Trp Met
             35                  40                  45

Gly Met Ile Asp Pro Ser Asp Ser Phe Thr Ser Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr His Ser Glu Glu Phe Asp Val Trp Gly Gln
                100                 105                 110

Gly Thr Leu Val Thr Val Ser Ser
            115                 120

<210> SEQ ID NO 22
<211> LENGTH: 109
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Arg Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Arg
                 85                  90                  95

Leu Phe Thr Phe Gly Gln Gly Thr Lys Leu Glu Ile Lys
                100                 105

<210> SEQ ID NO 23
<211> LENGTH: 120
<212> TYPE: PRT
```

<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Val Ser Trp Val Arg Gln Ala Pro Gly Lys Gly Leu Glu Trp Val
        35                  40                  45

Ser Thr Leu Tyr Thr Gly Gly Ser Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Thr Trp Glu Leu Leu Ser Ile Val Ala Phe Asp Ile Trp Gly Gln
            100                 105                 110

Gly Thr Met Val Thr Val Ser Ser
        115                 120

<210> SEQ ID NO 24
<211> LENGTH: 112
<212> TYPE: PRT
<213> ORGANISM: Homo sapiens

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Thr Pro Arg Thr Phe Gly Gln Gly Thr Lys Leu Glu Ile Lys
            100                 105                 110

<210> SEQ ID NO 25
<211> LENGTH: 121
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Asn
            20                  25                  30

Tyr Met Ser Trp Val Arg Gln Ala Pro Gly Lys Gly Leu Glu Trp Val
        35                  40                  45

Ser Thr Ile Gly Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Gly Gly Ser Trp Gly Phe Gly Trp Tyr Phe Asp Leu Trp Gly
            100                 105                 110

Arg Gly Thr Leu Val Thr Val Ser Ser
        115                 120
```

<210> SEQ ID NO 26
<211> LENGTH: 109
<212> TYPE: PRT
<213> ORGANISM: Homo sapiens

<400> SEQUENCE: 26

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Gly Ser
            20                  25                  30

Tyr Leu Ala Trp Tyr Gln Gln Lys Pro Gly Gln Ala Pro Arg Leu Leu
        35                  40                  45

Ile Tyr Asp Thr Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser
                85                  90                  95

Pro Gly Thr Phe Gly Gln Gly Thr Lys Leu Glu Ile Lys
            100                 105
```

<210> SEQ ID NO 27
<211> LENGTH: 122
<212> TYPE: PRT
<213> ORGANISM: Homo sapiens

<400> SEQUENCE: 27

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Gly Leu Glu Trp Met
        35                  40                  45

Gly Trp Ile Ser Pro His Asn Gly Asn Thr His Tyr Ala Gln Lys Phe
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Leu Trp Phe Gly Glu Leu Leu Pro Phe Asp Tyr Trp
            100                 105                 110

Gly Gln Gly Thr Leu Val Thr Val Ser Ser
        115                 120
```

<210> SEQ ID NO 28
<211> LENGTH: 108
<212> TYPE: PRT
<213> ORGANISM: Homo sapiens

<400> SEQUENCE: 28

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Phe Leu Ala Trp Tyr Gln Gln Lys Pro Gly Gln Ala Pro Arg Leu Leu
        35                  40                  45

Ile Tyr Ala Val Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Tyr Thr Phe Gly Gln Gly Thr Lys Leu Glu Ile Lys
                100                 105
```

<210> SEQ ID NO 29
<211> LENGTH: 120
<212> TYPE: PRT
<213> ORGANISM: Homo sapiens

<400> SEQUENCE: 29

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Lys Tyr
            20                  25                  30

Trp Ile Gly Trp Val Arg Gln Met Pro Gly Lys Gly Leu Glu Trp Met
        35                  40                  45

Gly Met Ile Asp Pro Thr Asp Ser Tyr Thr Thr Tyr Ser Pro Ser Leu
50                  55                  60

His Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gln Leu Trp Leu Arg Asp Ala Phe Asp Ile Trp Gly Gln
                100                 105                 110

Gly Thr Met Val Thr Val Ser Ser
            115                 120
```

<210> SEQ ID NO 30
<211> LENGTH: 107
<212> TYPE: PRT
<213> ORGANISM: Homo sapiens

<400> SEQUENCE: 30

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Val Gly Ser Asn
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Ala Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Tyr Trp Pro Ala
                85                  90                  95
```

Thr Phe Gly Gly Gly Thr Lys Val Glu Ile Lys
            100                 105

<210> SEQ ID NO 31
<211> LENGTH: 121
<212> TYPE: PRT
<213> ORGANISM: Homo sapiens

<400> SEQUENCE: 31

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Asp Tyr Ser Pro Ser Phe
    50                  55                  60

Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Ser Gln Arg Arg Gly Tyr Leu Asp Ala Phe Asp Ile Trp Gly
            100                 105                 110

Gln Gly Thr Met Val Thr Val Ser Ser
        115                 120

<210> SEQ ID NO 32
<211> LENGTH: 108
<212> TYPE: PRT
<213> ORGANISM: Homo sapiens

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Gly Thr Asp
            20                  25                  30

Leu Ala Trp Tyr Gln Gln Asn Pro Gly Gln Ala Pro Arg Leu Leu Ile
        35                  40                  45

Tyr Ala Ala Ser Ala Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Asn Trp Pro Leu
                85                  90                  95

Tyr Thr Phe Gly Gln Gly Thr Lys Leu Glu Ile Lys
            100                 105

<210> SEQ ID NO 33
<211> LENGTH: 118
<212> TYPE: PRT
<213> ORGANISM: Homo sapiens

<400> SEQUENCE: 33

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met

```
                    35                  40                  45
Gly Met Ile Asp Pro Ser Asp Ser Tyr Thr Thr Tyr Ser Pro Ser Phe
    50                  55                  60

Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Pro Ser Phe Thr Asp His Phe Asp Tyr Trp Gly Gln Gly Thr
            100                 105                 110

Leu Val Thr Val Ser Ser
        115
```

<210> SEQ ID NO 34
<211> LENGTH: 106
<212> TYPE: PRT
<213> ORGANISM: Homo sapiens

<400> SEQUENCE: 34

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Ala Ser Ala Arg Ala Ala Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Asp Asn Trp Pro Ala Thr
                85                  90                  95

Phe Gly Gly Gly Thr Lys Val Glu Ile Lys
            100                 105
```

<210> SEQ ID NO 35
<211> LENGTH: 121
<212> TYPE: PRT
<213> ORGANISM: Homo sapiens

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Ile Ser Trp Val Arg Gln Ala Pro Gly Lys Gly Leu Glu Trp Val
            35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala His Ser Glu Asp Tyr Tyr Asp Ser Ser Gly Phe Asp Tyr Trp Gly
            100                 105                 110

Gln Gly Thr Leu Val Thr Val Ser Ser
        115                 120
```

```
<210> SEQ ID NO 36
<211> LENGTH: 108
<212> TYPE: PRT
<213> ORGANISM: Homo sapiens

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Ala Arg Ala Ala Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Pro
                85                  90                  95

Val Thr Phe Gly Gln Gly Thr Lys Leu Glu Ile Lys
            100                 105

<210> SEQ ID NO 37
<211> LENGTH: 126
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Leu Thr Trp Val Arg Gln Ala Pro Gly Lys Gly Leu Asp Trp Val
        35                  40                  45

Ser Thr Ile Ser Gly Ser Gly Asn Thr Tyr Tyr Ala Asp Ser Val
50                  55                  60

Lys Gly Arg Phe Thr Ile Ser Arg Asp Asn Ser Arg Asn Thr Leu Ser
65                  70                  75                  80

Leu Gln Met Asn Ser Leu Arg Ala Asp Glu Thr Ala Val Tyr Tyr Cys
                85                  90                  95

Ala Lys Gly Gly Phe Ala Ser Ser Gly Arg Tyr Tyr Tyr Tyr Ala
            100                 105                 110

Met Asp Val Trp Gly Gln Gly Thr Thr Val Thr Val Ser Ser
        115                 120                 125

<210> SEQ ID NO 38
<211> LENGTH: 107
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60
```

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 39
<211> LENGTH: 121
<212> TYPE: PRT
<213> ORGANISM: Homo sapiens

<400> SEQUENCE: 39

Gln Ala Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Thr Ser Tyr Asp Gly Ser Asn Glu Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gln Trp Leu Val Pro Asp Asp Ala Phe Asp Ile Trp Gly
            100                 105                 110

Gln Gly Thr Met Val Thr Val Ser Ser
        115                 120

<210> SEQ ID NO 40
<211> LENGTH: 113
<212> TYPE: PRT
<213> ORGANISM: Homo sapiens

<400> SEQUENCE: 40

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Ser Asn Lys Asn Phe Leu Ala Trp Tyr Gln Gln Lys Pro Gly Gln
             35                  40                  45

Pro Pro Asn Leu Ile Ile Tyr Trp Ala Ser Asn Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                 85                  90                  95

Tyr Tyr Asn Thr Pro Pro Thr Phe Gly Gln Gly Thr Lys Val Glu Ile
            100                 105                 110

Lys

<210> SEQ ID NO 41
<211> LENGTH: 123
<212> TYPE: PRT
<213> ORGANISM: Homo sapiens
```

-continued

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Arg Ser Tyr
            20                  25                  30

Gly Ile Ser Trp Leu Arg Gln Ala Pro Gly Gln Gly Leu Glu Trp Met
        35                  40                  45

Gly Trp Ile Ser Ala Tyr Asn Gly Asp Thr Asn Tyr Ala Gln Lys Phe
    50                  55                  60

Gln Gly Arg Val Thr Leu Thr Thr Glu Lys Ser Thr Ser Thr Ala Tyr
65                  70                  75                  80

Met Glu Leu Arg Ser Leu Arg Ser Asp Asp Met Ala Val Tyr Tyr Cys
                85                  90                  95

Ala Lys Glu Asp Ile Ser Ser Arg Trp Ser Pro Asp Thr Phe Asp Ile
            100                 105                 110

Trp Gly Gln Gly Thr Leu Val Thr Val Ser Ser
        115                 120

<210> SEQ ID NO 42
<211> LENGTH: 107
<212> TYPE: PRT
<213> ORGANISM: Homo sapiens

<400> SEQUENCE: 42

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Thr Gly Val Pro Ser Arg Phe Ser Gly
    50                  55                  60

Ser Gly Tyr Gly Thr Glu Phe Thr Leu Thr Ile Ser Ser Leu Gln Ser
65                  70                  75                  80

Asp Asp Phe Ala Thr Tyr Tyr Cys Gln Gln Tyr Asn His Tyr Ser Arg
                85                  90                  95

Thr Phe Gly Gln Gly Thr Lys Leu Glu Ile Lys
            100                 105

<210> SEQ ID NO 43
<211> LENGTH: 124
<212> TYPE: PRT
<213> ORGANISM: Homo sapiens

<400> SEQUENCE: 43

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Asn
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys

```
                    85                  90                  95
Ala Lys Asp Trp Ala Met Val Arg Gly Val Ile Thr Asn Ala Phe Asp
                100                 105                 110
Ile Trp Gly Gln Gly Thr Met Val Thr Val Ser Ser
        115                 120
```

<210> SEQ ID NO 44
<211> LENGTH: 106
<212> TYPE: PRT
<213> ORGANISM: Homo sapiens

<400> SEQUENCE: 44

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Lys Ala Ser Ser Leu Glu Ser Gly Val Pro Ser Arg Phe Ser Gly
50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Phe Asn Arg Tyr Ser Thr
                85                  90                  95
Phe Gly Gln Gly Thr Lys Val Glu Ile Lys
            100                 105
```

<210> SEQ ID NO 45
<211> LENGTH: 120
<212> TYPE: PRT
<213> ORGANISM: Homo sapiens

<400> SEQUENCE: 45

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Asn
            20                  25                  30
Tyr Tyr Tyr Trp Gly Trp Ile Arg Gln Thr Pro Gly Lys Arg Leu Glu
        35                  40                  45
Trp Ile Gly Ser Ile Tyr Tyr Ser Gly Ser Thr Tyr Tyr Asn Pro Ser
50                  55                  60
Leu Lys Ser Arg Val Thr Ile Ser Ile Asp Thr Ser Lys Asn Gln Phe
65                  70                  75                  80
Ser Leu Thr Leu Ser Phe Val Thr Ala Ala Asp Thr Ala Val Tyr Tyr
                85                  90                  95
Cys Ala Arg Glu Ala Glu Arg His Asp Ser Phe Asp Ile Trp Gly Gln
            100                 105                 110
Gly Thr Met Val Thr Val Ser Ser
        115                 120
```

<210> SEQ ID NO 46
<211> LENGTH: 107
<212> TYPE: PRT
<213> ORGANISM: Homo sapiens

<400> SEQUENCE: 46

```
Glu Ile Val Met Thr Gln Ser Pro Val Thr Leu Ser Val Ser Pro Gly
1               5                   10                  15
```

Glu Arg Ala Thr Leu Ser Cys Arg Ala Ser Gln Asn Val Tyr Asn Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Phe Pro Gly Arg Phe Ser Gly
50                      55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Val Trp Pro Phe
                85                  90                  95

Thr Phe Gly Pro Gly Thr Lys Val Asp Ile Lys
            100                 105

<210> SEQ ID NO 47
<211> LENGTH: 120
<212> TYPE: PRT
<213> ORGANISM: Homo sapiens

<400> SEQUENCE: 47

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Tyr Tyr Tyr Trp Gly Trp Ile Arg Gln Thr Pro Gly Lys Gly Leu Glu
            35                  40                  45

Trp Ile Gly Ser Ile Tyr Tyr Ser Gly Ser Thr Tyr Tyr Asn Pro Ser
50                  55                      60

Leu Lys Ser Arg Val Thr Ile Ser Ile Asp Thr Ser Lys Asn Gln Phe
65                  70                  75                  80

Ser Leu Thr Leu Ser Phe Val Thr Ala Ala Asp Thr Ala Val Tyr Tyr
                85                  90                  95

Cys Ala Arg Glu Ala Glu Arg His Asp Ser Phe Asp Leu Trp Gly Gln
            100                 105                 110

Gly Thr Met Val Thr Val Ser Ser
        115                 120

<210> SEQ ID NO 48
<211> LENGTH: 107
<212> TYPE: PRT
<213> ORGANISM: Homo sapiens

<400> SEQUENCE: 48

Glu Ile Val Met Thr Gln Ser Pro Val Thr Leu Ser Val Ser Pro Gly
1               5                   10                  15

Glu Arg Ala Thr Leu Ser Cys Arg Ala Ser Gln Asn Val Tyr Asn Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Gly Arg Phe Ser Gly
50                      55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Val Trp Pro Phe
                85                  90                  95

Thr Phe Gly Pro Gly Thr Lys Val Asp Ile Lys
            100                 105

<210> SEQ ID NO 49
<211> LENGTH: 116
<212> TYPE: PRT
<213> ORGANISM: Homo sapiens

<400> SEQUENCE: 49

Gln Glu Gln Leu Val Glu Ser Gly Gly Asp Val Val Gln Pro Gly Lys
1               5                   10                  15

Ser Leu Arg Leu Ser Cys Thr Thr Ser Gly Phe Thr Phe Ser Phe Tyr
            20                  25                  30

Gly Ile His Trp Val Arg Gln Ala Pro Gly Lys Gly Leu Glu Trp Val
        35                  40                  45

Thr Ser Ile Ser Tyr Asp Gly Thr Asn Lys Tyr Tyr Ala Asp Ser Val
    50                  55                  60

Lys Gly Arg Phe Thr Ile Ser Arg Asp Asn Ser Lys Gly Thr Leu Tyr
65                  70                  75                  80

Leu Gln Met Asp Ser Leu Arg Pro Glu Asp Thr Ala Val Tyr Tyr Cys
                85                  90                  95

Val Lys Asp Ser Arg Gly Met Ala Val Trp Gly Gln Gly Thr Thr Val
            100                 105                 110

Thr Val Ser Ser
        115

<210> SEQ ID NO 50
<211> LENGTH: 112
<212> TYPE: PRT
<213> ORGANISM: Homo sapiens

<400> SEQUENCE: 50

Asp Val Leu Met Thr Gln Ser Pro Leu Phe Leu Pro Val Thr Phe Gly
1               5                   10                  15

Gln Pro Ala Ser Ile Ser Cys Arg Ser Ser Arg Ser Leu Val Tyr Ser
            20                  25                  30

Asp Gly Asn Thr Tyr Val Asn Trp Phe His Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Val Glu Ile Lys
            100                 105                 110

<210> SEQ ID NO 51
<211> LENGTH: 120
<212> TYPE: PRT
<213> ORGANISM: Homo sapiens

<400> SEQUENCE: 51

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Tyr Tyr Trp Gly Trp Ile Arg Gln Thr Pro Gly Lys Gly Leu Glu
        35                  40                  45

```
Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn His Phe
65                  70                  75                  80

Ser Leu Asn Leu Ser Phe Val Thr Ala Ala Asp Thr Ala Val Tyr Tyr
                85                  90                  95

Cys Ala Arg Glu Ala Glu Arg His Asp Thr Phe Asp Ile Trp Gly Gln
            100                 105                 110

Gly Thr Met Val Thr Val Ser Ser
            115                 120

<210> SEQ ID NO 52
<211> LENGTH: 107
<212> TYPE: PRT
<213> ORGANISM: Homo sapiens

<400> SEQUENCE: 52

Glu Ile Val Met Thr Gln Ser Pro Val Thr Leu Ser Val Ser Pro Gly
1               5                   10                  15

Glu Arg Ala Thr Leu Ser Cys Arg Ala Ser Gln Asn Ile Ser Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Gly Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 53
<211> LENGTH: 119
<212> TYPE: PRT
<213> ORGANISM: Homo sapiens

<400> SEQUENCE: 53

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Leu Gly Ser Tyr Glu Phe Asp Tyr Trp Gly Gln Gly
            100                 105                 110

Thr Leu Val Thr Val Ser Ser
            115

<210> SEQ ID NO 54
<211> LENGTH: 112
```

<212> TYPE: PRT
<213> ORGANISM: Homo sapiens

<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Ser Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 55
<211> LENGTH: 117
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Ser Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Ala Thr Ala Val Tyr Tyr Cys
                85                  90                  95

Ala Arg Gly Tyr Tyr Asp Ile Phe Asp Tyr Trp Gly Gln Gly Thr Leu
            100                 105                 110

Val Thr Val Ser Ser
        115

<210> SEQ ID NO 56
<211> LENGTH: 107
<212> TYPE: PRT
<213> ORGANISM: Homo sapiens

<400> SEQUENCE: 56

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Thr Ile Gly Asn Ser
            20                  25                  30

Leu His Trp Tyr Gln Gln Lys Pro Asp Gln Ser Pro Lys Leu Leu Ile
        35                  40                  45

Glu Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ile Ser Leu Glu Ala

```
                 65                  70                  75                  80
Glu Asp Ala Ala Ala Tyr Tyr Cys His Gln Ser Ser Arg Leu Pro Trp
                 85                  90                  95

Thr Phe Gly Gln Gly Thr Lys Val Glu Ile Lys
                100                 105
```

<210> SEQ ID NO 57
<211> LENGTH: 124
<212> TYPE: PRT
<213> ORGANISM: Homo sapiens

<400> SEQUENCE: 57

```
Glu Val Gln Leu Val Gln Ser Gly Ala Glu Val Lys Lys Pro Gly Glu
1               5                   10                  15

Ser Leu Lys Ile Ser Cys Lys Gly Phe Gly Tyr Arg Phe Thr Asp Tyr
                20                  25                  30

Trp Ile Gly Trp Ile Arg Gln Met Pro Gly Lys Gly Leu Glu Trp Met
                35                  40                  45

Gly Ile Ile Tyr Pro Asp Asp Ser Asp Thr Arg Tyr Ser Pro Ser Phe
        50                  55                  60

Gln Gly Gln Val Thr Ile Ser Ala Asp Arg Ser Val Lys Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Ile Ile Gly Thr Arg Asp Tyr Tyr Tyr Gly Met Asp
                100                 105                 110

Val Trp Gly Gln Gly Thr Thr Val Thr Val Ser Ser
                115                 120
```

<210> SEQ ID NO 58
<211> LENGTH: 107
<212> TYPE: PRT
<213> ORGANISM: Homo sapiens

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
                20                  25                  30

Leu Asp Trp Tyr Gln Gln Lys Pro Gly Lys Ala Pro Lys Leu Leu Ile
                35                  40                  45

Tyr Asp Ala Ser Thr Leu Ile Thr Gly Val Pro Ser Arg Phe Ser Gly
        50                  55                  60

Ser Gly Ser Gly Thr Tyr Phe Thr Phe Thr Ile Ser Ser Leu Gln Pro
65                  70                  75                  80

Asp Asp Ile Ala Thr Tyr Tyr Cys Gln His Tyr Asp Asn Leu Pro Phe
                85                  90                  95

Thr Phe Gly Pro Gly Thr Lys Leu Glu Ile Lys
                100                 105
```

<210> SEQ ID NO 59
<211> LENGTH: 124
<212> TYPE: PRT
<213> ORGANISM: Homo sapiens

<400> SEQUENCE: 59

```
Glu Val Gln Leu Val Glu Ser Gly Gly Gly Leu Val Gln Pro Gly Arg
1               5                   10                  15
```

```
Ser Leu Arg Leu Ser Cys Ala Ala Ser Gly Leu Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Gly Gly Ser Lys Glu Tyr Ala Ala Ser Val
 50                      55                  60

Lys Gly Arg Phe Thr Ile Ser Arg Asp Asn Ala Lys Asn Phe Leu Tyr
 65                  70                  75                  80

Leu Gln Met Asn Ser Leu Arg Val Glu Asp Thr Ala Leu Tyr Tyr Cys
                85                  90                  95

Ala Lys Asp Trp Ala Met Val Arg Gly Val Ile Thr Asn Val Phe Asp
            100                 105                 110

Ile Trp Gly Gln Gly Thr Met Val Thr Val Ser Ser
            115                 120

<210> SEQ ID NO 60
<211> LENGTH: 106
<212> TYPE: PRT
<213> ORGANISM: Homo sapiens

<400> SEQUENCE: 60

Ala Ile Gln Met Thr Gln Ser Pro Ser Thr Leu Ser Ala Ser Val Gly
 1               5                  10                  15

Asp Arg Val Thr Ile Thr Cys Arg Ala Ser Gln Thr Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                      55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ser Ser Tyr Ser Thr
                85                  90                  95

Phe Gly Gln Gly Thr Lys Val Glu Ile Lys
            100                 105

<210> SEQ ID NO 61
<211> LENGTH: 119
<212> TYPE: PRT
<213> ORGANISM: Homo sapiens

<400> SEQUENCE: 61

Gln Glu Gln Leu Val Glu Ser Gly Gly Val Val Gln Pro Gly Arg
 1               5                  10                  15

Ser Leu Arg Leu Ser Cys Ala Ala Ser Gly Phe Asn Phe Asn Thr Tyr
            20                  25                  30

Ala Met His Trp Val Arg Gln Ala Pro Gly Lys Gly Leu Glu Trp Val
            35                  40                  45

Thr Val Ile Ser Phe Asp Ser Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Glu Met Asn Ser Leu Lys Pro Glu Asp Thr Ala Ile Tyr Tyr Cys
                85                  90                  95

Val Lys Gly Arg Ser Tyr Tyr Trp Tyr Phe Asp Leu Trp Gly Arg Gly
            100                 105                 110
```

Thr Leu Val Thr Val Ser Ser
        115

<210> SEQ ID NO 62
<211> LENGTH: 112
<212> TYPE: PRT
<213> ORGANISM: Homo sapiens

<400> SEQUENCE: 62

Asn Ile Ile Met Thr Gln Thr Pro Leu Ser Leu Pro Val Ser Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Thr Trp Leu Gln Gln Arg Pro Gly Gln Pro
        35                  40                  45

Pro Arg Leu Leu Ile Tyr Lys Ile Ser Lys Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Thr His Phe Pro His Thr Phe Gly Gly Gly Thr Lys Val Glu Ile Lys
            100                 105                 110

<210> SEQ ID NO 63
<211> LENGTH: 121
<212> TYPE: PRT
<213> ORGANISM: Homo sapiens

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Ser
            20                  25                  30

Ala Met Ser Trp Val Arg Gln Ala Pro Gly Lys Gly Leu Tyr Trp Val
        35                  40                  45

Ser Ala Ile Ser Gly Asn Gly Asp Asn Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Leu Tyr Tyr Cys
                85                  90                  95

Ala Glu Glu Gly Ile Val Val Ala His Asp Ala Phe Glu Ile Trp Gly
            100                 105                 110

Gln Gly Thr Met Val Thr Val Ser Ser
        115                 120

<210> SEQ ID NO 64
<211> LENGTH: 113
<212> TYPE: PRT
<213> ORGANISM: Homo sapiens

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

```
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Ile Arg Glu Ser Gly Val
 50                  55                  60

Pro Asp Arg Ile Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Gly Thr Pro Ile Thr Phe Gly Gln Gly Thr Arg Leu Glu Ile
                100                 105                 110

Lys

<210> SEQ ID NO 65
<211> LENGTH: 109
<212> TYPE: PRT
<213> ORGANISM: Oryctolagus cuniculus

<400> SEQUENCE: 65

Gln Glu Arg Leu Lys Glu Ser Gly Gly Arg Leu Val Thr Pro Gly Thr
 1               5                  10                  15

Pro Leu Thr Leu Thr Cys Thr Ala Gly Gly Ser Asp Ile Ser Val Tyr
                 20                  25                  30

Gly Ile His Trp Val Arg Gln Ala Pro Gly Lys Gly Leu Glu Trp Ile
             35                  40                  45

Gly Trp Ile Gly Ala Gly Gly His Ala Tyr Tyr Ala Arg Trp Ala Val
         50                  55                  60

Gly Arg Phe Thr Ile Ser Arg Thr Ser Thr Thr Val Asp Leu Lys Met
 65                  70                  75                  80

Thr Ser Pro Thr Thr Glu Asp Thr Ala Thr Tyr Phe Cys Ala Ser Ala
                 85                  90                  95

Gly Leu Trp Gly Pro Gly Thr Leu Val Thr Val Ser Ser
                100                 105

<210> SEQ ID NO 66
<211> LENGTH: 112
<212> TYPE: PRT
<213> ORGANISM: Oryctolagus cuniculus

<400> SEQUENCE: 66

Gln Val Leu Thr Gln Thr Glu Ser Pro Val Ser Ala Ala Ile Gly Gly
 1               5                  10                  15

Thr Val Thr Ile Asn Cys Gln Ser Ser Gln Ser Val Val Asn Asp Asn
                 20                  25                  30

Arg Leu Ser Trp Tyr Gln Gln Lys Pro Gly Gln Pro Pro Lys Arg Leu
             35                  40                  45

Ile Tyr Asp Ala Ser Lys Leu Ala Ser Gly Val Pro Ser Arg Phe Lys
         50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Gly Tyr Asp Cys Ser
                 85                  90                  95

Leu Asn Asp Cys Asn Gly Phe Gly Gly Gly Thr Glu Val Val Val Lys
                100                 105                 110

<210> SEQ ID NO 67
<211> LENGTH: 119
<212> TYPE: PRT
```

<213> ORGANISM: Oryctolagus cuniculus

<400> SEQUENCE: 67

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Tyr Thr
            20                  25                  30

Met Gly Trp Val Arg Gln Ala Pro Gly Lys Gly Leu Glu Tyr Ile Gly
        35                  40                  45

Ile Ile Ala Ser Ser Gly His Ala Tyr Tyr Ala Ser Trp Ala Lys Gly
    50                  55                  60

Arg Phe Thr Ile Ser Lys Thr Ser Thr Ala Val Asp Leu Lys Met
65                  70                  75                  80

Thr Ser Leu Thr Thr Glu Asp Thr Ala Thr Tyr Phe Cys Val Arg Ala
            85                  90                  95

Leu Tyr Ser Gly Gly Gly Tyr Trp Pro Gly Gly Phe Trp Gly Pro Gly
            100                 105                 110

Thr Leu Val Thr Val Ser Ser
            115

<210> SEQ ID NO 68
<211> LENGTH: 111
<212> TYPE: PRT
<213> ORGANISM: Oryctolagus cuniculus

<400> SEQUENCE: 68

Ile Val Met Thr Gln Thr Pro Ser Ser Lys Ser Val Pro Val Gly Asp
1               5                   10                  15

Thr Val Thr Ile Asn Cys Gln Ala Ser Lys Ser Val Tyr Ser Asn Asn
            20                  25                  30

Arg Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Arg
    50                  55                  60

Gly Ser Gly Ser Gly Thr Gln Phe Thr Leu Thr Ile Ser Asp Val Val
65                  70                  75                  80

Cys Asp Asp Ala Ala Thr Tyr Tyr Cys Ala Gly Tyr Glu Glu Ser Ile
            85                  90                  95

Asp Asp Asp Thr Ala Phe Gly Gly Gly Thr Glu Val Val Val Lys
            100                 105                 110

<210> SEQ ID NO 69
<211> LENGTH: 122
<212> TYPE: PRT
<213> ORGANISM: Homo sapiens

<400> SEQUENCE: 69

Glu Val Gln Leu Val Glu Ser Gly Gly Gly Leu Val Gln Pro Gly Arg
1               5                   10                  15

Ser Leu Lys Leu Thr Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Gly Asp Asn Ile Gly Tyr Val Glu Ser Val
    50                  55                  60

Lys Gly Arg Phe Thr Ile Ser Arg Asp Asn Asp Lys Asn Ser Leu His
65                  70                  75                  80

Leu Glu Leu Asn Ser Leu Arg Pro Glu Asp Thr Ala Leu Tyr Phe Cys
            85                  90                  95

Ala Lys Ser Tyr Gly Ser Gly Ser Tyr Tyr Asn Ala Phe Asp Ser Trp
            100                 105                 110

Gly Gln Gly Thr Leu Val Thr Val Ser Ser
            115                 120

<210> SEQ ID NO 70
<211> LENGTH: 107
<212> TYPE: PRT
<213> ORGANISM: Homo sapiens

<400> SEQUENCE: 70

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Ser Leu Thr Ile Ser Ser Leu Gln Pro
65              70                  75                  80

Asp Asp Phe Ala Thr Tyr Tyr Cys Leu Glu Tyr Ser Ser Tyr Ile Arg
            85                  90                  95

Thr Phe Gly Gln Gly Thr Lys Val Glu Ile Lys
            100                 105

<210> SEQ ID NO 71
<211> LENGTH: 122
<212> TYPE: PRT
<213> ORGANISM: Homo sapiens

<400> SEQUENCE: 71

Glu Val Gln Leu Val Glu Ser Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Val Pro Gly Lys Gly Leu Glu Trp Val
            35                  40                  45

Ser Gly Ile Ser Trp Asn Ser Asp Asn Ile Gly Tyr Ala Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
            85                  90                  95

Ala Lys Ala Phe Gly Ser Gly Ser Tyr Tyr Asn Gly Phe Asp Tyr Trp
            100                 105                 110

Gly Gln Gly Thr Leu Val Thr Val Ser Ser
            115                 120

<210> SEQ ID NO 72
<211> LENGTH: 107
<212> TYPE: PRT
<213> ORGANISM: Homo sapiens

<400> SEQUENCE: 72

```
Asp Ile Gln Met Thr Gln Ser Pro Ser Thr Leu Ser Ala Ser Ala Gly
1               5                   10                  15

Asp Arg Val Thr Ile Ser Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu Tyr Asn Ser Tyr Ile Arg
                85                  90                  95

Thr Phe Gly Gln Gly Thr Lys Val Glu Ile Lys
            100                 105
```

<210> SEQ ID NO 73
<211> LENGTH: 122
<212> TYPE: PRT
<213> ORGANISM: Homo sapiens

<400> SEQUENCE: 73

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Asp Asn Ile Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ile Glu Asp Thr Ala Leu Tyr Tyr Cys
                85                  90                  95

Ala Lys Ala Phe Gly Ser Gly Ser Tyr Tyr Asn Gly Phe Asp Tyr Trp
            100                 105                 110

Gly Gln Gly Ala Leu Val Thr Val Ser Ser
        115                 120
```

<210> SEQ ID NO 74
<211> LENGTH: 107
<212> TYPE: PRT
<213> ORGANISM: Homo sapiens

<400> SEQUENCE: 74

```
Asp Ile Gln Met Thr Gln Ser Pro Ser Thr Leu Ser Ala Ser Ala Gly
1               5                   10                  15

Asp Arg Val Thr Ile Ser Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu Tyr Asn Ser Tyr Ile Arg
                85                  90                  95
```

```
Thr Phe Gly Gln Gly Thr Lys Val Glu Ile Lys
            100                 105

<210> SEQ ID NO 75
<211> LENGTH: 121
<212> TYPE: PRT
<213> ORGANISM: Mus musculus

<400> SEQUENCE: 75

Gln Val Gln Leu Gln Gln Ser Gly Ala Glu Leu Val Arg Pro Gly Ser
1               5                   10                  15

Ser Val Lys Ile Ser Cys Lys Ala Ser Ala Tyr Glu Phe Ser Lys His
            20                  25                  30

Trp Met Asn Trp Val Lys Gln Arg Pro Gly Gln Gly Leu Glu Trp Val
        35                  40                  45

Gly Gln Ile Tyr Pro Gly Asp Gly Asp Thr Asn Tyr Asn Arg Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Gly Tyr Asp Glu Glu Tyr Tyr Gly Met Asp Tyr Trp Gly
            100                 105                 110

Gln Gly Thr Ser Val Thr Val Ser Ser
        115                 120

<210> SEQ ID NO 76
<211> LENGTH: 107
<212> TYPE: PRT
<213> ORGANISM: Mus musculus

<400> SEQUENCE: 76

Asp Ile Gln Met Thr Gln Ser Pro Ala Ser Leu Ser Ala Ser Val Gly
1               5                   10                  15

Glu Ala Val Thr Ile Thr Cys Arg Val Asn Glu Asn Ile Asp Ser Tyr
            20                  25                  30

Leu Ala Trp Tyr Gln Gln Lys Gln Gly Lys Ser Pro Gln Leu Leu Val
        35                  40                  45

Tyr Ala Ala Thr Leu Leu Ala Asp Gly Val Pro Pro Arg Phe Ser Gly
    50                  55                  60

Ser Gly Ser Gly Thr Gln Phe Ser Leu Lys Ile Asn Ser Leu Gln Ser
65                  70                  75                  80

Glu Asp Val Ala Arg Tyr Phe Cys Gln His Tyr Tyr Ser Thr Pro Trp
                85                  90                  95

Thr Phe Gly Gly Gly Thr Lys Leu Glu Ile Lys
            100                 105

<210> SEQ ID NO 77
<211> LENGTH: 121
<212> TYPE: PRT
<213> ORGANISM: Mus musculus

<400> SEQUENCE: 77

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Lys His
            20                  25                  30

Trp Met Asn Trp Val Lys Gln Arg Pro Gly Gln Gly Leu Glu Trp Ile
```

```
                   35                  40                  45

Gly Gln Ile Tyr Pro Gly Asp Gly Asp Ile Asn Tyr Asn Lys Phe
            50                  55                  60

Lys Gly Lys Ala Thr Leu Thr Ala Asp Lys Ser Ser Thr Ala Tyr
 65                 70                  75                  80

Met Gln Leu Ser Ser Leu Thr Ser Glu Asp Ser Ala Val Tyr Phe Cys
                85                  90                  95

Ala Arg Tyr Gly Tyr Asn Glu Glu Tyr Tyr Gly Leu Asp Tyr Trp Gly
            100                 105                 110

Gln Gly Thr Ser Val Thr Val Ser Ser
            115                 120

<210> SEQ ID NO 78
<211> LENGTH: 107
<212> TYPE: PRT
<213> ORGANISM: Mus musculus

<400> SEQUENCE: 78

Asp Ile Gln Met Thr Gln Ser Pro Ala Ser Leu Ser Ala Ser Val Gly
 1               5                  10                  15

Glu Thr Val Thr Ile Thr Cys Arg Ile Ser Glu Asn Ile Asp Ser Tyr
            20                  25                  30

Leu Ala Trp Tyr Gln Gln Lys Gln Gly Lys Ser Pro Gln Leu Leu Val
            35                  40                  45

Tyr Ala Ala Thr Leu Leu Ala Asp Gly Val Pro Ser Arg Phe Ser Gly
            50                  55                  60

Ser Gly Ser Gly Thr Gln Phe Ser Leu Lys Ile Asn Ser Leu Gln Ser
 65                 70                  75                  80

Glu Asp Val Ala Arg Tyr Phe Cys Gln His Tyr Tyr Ser Thr Pro Trp
                85                  90                  95

Thr Phe Gly Gly Gly Thr Lys Leu Glu Ile Lys
            100                 105

<210> SEQ ID NO 79
<211> LENGTH: 117
<212> TYPE: PRT
<213> ORGANISM: Oryctolagus cuniculus

<400> SEQUENCE: 79

Gln Ser Leu Ala Glu Ser Gly Gly Arg Leu Val Thr Pro Gly Thr Pro
 1               5                  10                  15

Leu Thr Leu Thr Cys Thr Ala Pro Gly Phe Thr Ile Gly Gly Tyr His
            20                  25                  30

Met Ser Trp Val Arg Gln Ala Pro Gly Lys Gly Leu Glu Trp Ile Gly
            35                  40                  45

Leu Ile Asn Asn Gly Gly Ser Thr Ala Tyr Ala Asn Trp Val Lys Gly
            50                  55                  60

Arg Phe Thr Ile Ser Lys Thr Ser Thr Val Asp Leu Lys Leu Thr
 65                 70                  75                  80

Ser Leu Thr Ser Glu Gly Thr Ala Thr Tyr Phe Cys Ala Arg Trp Thr
                85                  90                  95

Gly Tyr Ala Gly Asp Gly Tyr Gly Asp Ile Trp Gly Gln Gly Thr Leu
            100                 105                 110

Val Thr Val Ser Ser
            115
```

<210> SEQ ID NO 80
<211> LENGTH: 111
<212> TYPE: PRT
<213> ORGANISM: Oryctolagus cuniculus

<400> SEQUENCE: 80

Ala Asp Ile Val Met Thr Gln Thr Pro Ala Ser Val Ser Ala Ala Val
1               5                   10                  15

Gly Gly Thr Val Thr Phe Lys Cys Gln Ala Ser Glu Asn Ile Tyr Asn
            20                  25                  30

Leu Leu Ala Trp Tyr Gln Gln Lys Pro Gly Gln Pro Pro Lys Leu Leu
        35                  40                  45

Ile Tyr Asp Ala Phe Asp Leu Ala Ser Gly Val Pro Ser Arg Phe Lys
50                  55                  60

Gly Ser Gly Ser Gly Thr Gln Phe Thr Leu Thr Ile Ser Asp Leu Glu
65                  70                  75                  80

Ser Ala Asp Ala Ala Thr Tyr Tyr Cys Gln Ser Tyr Tyr Tyr Ala Ser
                85                  90                  95

Ser Ser Ser Tyr Pro Phe Gly Gly Gly Thr Glu Val Val Val Lys
            100                 105                 110

<210> SEQ ID NO 81
<211> LENGTH: 122
<212> TYPE: PRT
<213> ORGANISM: Homo sapiens

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Asp Asn Ile Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ile Glu Asp Thr Ala Leu Tyr Tyr Cys
                85                  90                  95

Ala Lys Ala Phe Gly Ser Gly Ser Tyr Tyr Asn Gly Phe Asp Tyr Trp
            100                 105                 110

Gly Gln Gly Ala Leu Val Thr Val Ser Ser
        115                 120

<210> SEQ ID NO 82
<211> LENGTH: 107
<212> TYPE: PRT
<213> ORGANISM: Homo sapiens

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gly Gln Tyr Arg Ser Tyr Ser Arg
                 85                  90                  95

Thr Phe Gly Gly Gly Thr Lys Val Glu Ile Lys
            100                 105
```

<210> SEQ ID NO 83
<211> LENGTH: 122
<212> TYPE: PRT
<213> ORGANISM: Homo sapiens

<400> SEQUENCE: 83

```
Glu Val Gln Leu Val Glu Ser Gly Gly Leu Val Gln Pro Gly Arg
 1               5                  10                  15

Ser Leu Lys Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
             35                  40                  45

Ser Gly Ile Ser Trp Asn Gly Asp Asn Ile Gly Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 84
<211> LENGTH: 107
<212> TYPE: PRT
<213> ORGANISM: Homo sapiens

<400> SEQUENCE: 84

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Leu Gln Tyr Arg Ser Tyr Ser Arg
                 85                  90                  95

Thr Phe Gly Gly Gly Thr Lys Val Glu Ile Lys
            100                 105
```

<210> SEQ ID NO 85
<211> LENGTH: 120
<212> TYPE: PRT
<213> ORGANISM: Oryctolagus cuniculus

<400> SEQUENCE: 85

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ala Tyr Ala
                20                  25                  30

Val Ser Trp Val Arg Gln Ala Pro Gly Lys Gly Leu Glu Trp Ile Gly
            35                  40                  45

Ile Val Ser Ser Ser Asp Phe Thr Tyr Tyr Ala Ser Trp Ala Lys Gly
50                      55                  60

Arg Phe Thr Ile Ser Lys Thr Ser Thr Thr Val Glu Leu Lys Ile Thr
65                  70                  75                  80

Ser Pro Thr Thr Glu Asp Thr Ala Thr Tyr Phe Cys Ala Arg Asp Leu
                85                  90                  95

Asn Tyr Asp Asp Tyr Glu Asn Tyr Tyr Gly Met Asp Pro Trp Gly Pro
            100                 105                 110

Gly Thr Leu Val Thr Val Ser Ser
            115                 120

<210> SEQ ID NO 86
<211> LENGTH: 113
<212> TYPE: PRT
<213> ORGANISM: Oryctolagus cuniculus

<400> SEQUENCE: 86

Asp Val Val Met Thr Gln Thr Pro Ser Ser Val Ser Ala Ala Val Gly
1               5                   10                  15

Gly Thr Val Thr Ile Lys Cys Gln Ser Ser Gln Ser Val Tyr Asn Tyr
                20                  25                  30

Asn Leu Leu Ser Trp Tyr Gln Gln Lys Pro Gly Gln Pro Pro Lys Leu
            35                  40                  45

Leu Ile Tyr Gly Ala Ser Asn Leu Ala Ser Gly Val Pro Asp Arg Phe
50                      55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Ser Phe Asp Asp
                85                  90                  95

Asp Val Asp Tyr Glu Asn Ala Phe Gly Gly Gly Thr Glu Val Val Val
            100                 105                 110

Lys

<210> SEQ ID NO 87
<211> LENGTH: 119
<212> TYPE: PRT
<213> ORGANISM: Oryctolagus cuniculus

<400> SEQUENCE: 87

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Tyr Thr
                20                  25                  30

Met Gly Trp Val Arg Gln Ala Pro Gly Lys Gly Leu Glu Tyr Ile Gly
            35                  40                  45

Ile Ile Ala Ser Ser Gly His Ala Tyr Tyr Ala Ser Trp Ala Lys Gly
50                      55                  60

Arg Phe Thr Ile Ser Lys Thr Ser Ser Thr Ala Val Asp Leu Lys Met
65                  70                  75                  80

Thr Ser Leu Thr Thr Glu Asp Thr Ala Thr Tyr Phe Cys Val Arg Ala

```
                    85                  90                  95

Leu Tyr Ser Gly Gly Gly Tyr Trp Pro Gly Gly Phe Trp Gly Pro Gly
                100                 105                 110

Thr Leu Val Thr Val Ser Ser
            115

<210> SEQ ID NO 88
<211> LENGTH: 110
<212> TYPE: PRT
<213> ORGANISM: Oryctolagus cuniculus

<400> SEQUENCE: 88

Val Met Thr Gln Thr Pro Ser Ser Lys Ser Val Pro Val Gly Asp Thr
1               5                   10                  15

Val Thr Ile Asn Cys Gln Ala Ser Lys Ser Val Tyr Ser Asn Asn Arg
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Arg Gly
    50                  55                  60

Ser Gly Ser Gly Thr Gln Phe Thr Leu Thr Ile Ser Asp Val Val Cys
65                  70                  75                  80

Asp Asp Ala Ala Thr Tyr Tyr Cys Ala Gly Tyr Glu Glu Ser Ile Asp
                85                  90                  95

Asp Asp Thr Ala Phe Gly Gly Gly Thr Glu Val Val Val Lys
                100                 105                 110

<210> SEQ ID NO 89
<211> LENGTH: 119
<212> TYPE: PRT
<213> ORGANISM: Homo sapiens

<400> SEQUENCE: 89

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Glu Gly Ala Phe Asp Ile Trp Gly Gln Gly
                100                 105                 110

Thr Met Val Thr Val Ser Ser
            115

<210> SEQ ID NO 90
<211> LENGTH: 112
<212> TYPE: PRT
<213> ORGANISM: Homo sapiens

<400> SEQUENCE: 90

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Arg Leu Leu His Ser
                20                  25                  30

Thr Gly Tyr Asn Tyr Leu Asn Trp Tyr Leu Gln Lys Pro Gly Gln Ser
            35                  40                  45

Pro Gln Leu Leu Ile Tyr Leu Gly Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu His Ile Pro Tyr Thr Phe Gly Gln Gly Thr Lys Leu Glu Ile Lys
            100                 105                 110

<210> SEQ ID NO 91
<211> LENGTH: 119
<212> TYPE: PRT
<213> ORGANISM: Homo sapiens

<400> SEQUENCE: 91

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
                20                  25                  30

Trp Ile Gly Trp Val Arg Gln Met Pro Gly Lys Gly Leu Glu Trp Met
            35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115

<210> SEQ ID NO 92
<211> LENGTH: 112
<212> TYPE: PRT
<213> ORGANISM: Homo sapiens

<400> SEQUENCE: 92

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
                20                  25                  30

Thr Tyr Tyr Asn Tyr Leu Asn Trp Tyr Leu Gln Lys Pro Gly Gln Ser
            35                  40                  45

Pro Gln Leu Leu Ile Tyr Leu Gly Lys Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 93
<211> LENGTH: 123
<212> TYPE: PRT
<213> ORGANISM: Homo sapiens

<400> SEQUENCE: 93

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
            20                  25                  30
Trp Met Asn Trp Val Arg Gln Ala Pro Gly Lys Gly Leu Glu Trp Val
        35                  40                  45
Gly Arg Ile Lys Arg Lys Thr Asp Gly Gly Thr Thr Asp Tyr Ala Ala
    50                  55                  60
Pro Val Lys Gly Arg Phe Thr Ile Ser Arg Asn Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Thr Asp Gly Ile Ala Val Ala Gly Pro Leu Arg Val Tyr
            100                 105                 110
Trp Gly Gln Gly Thr Leu Val Thr Val Ser Ser
        115                 120
```

<210> SEQ ID NO 94
<211> LENGTH: 113
<212> TYPE: PRT
<213> ORGANISM: Homo sapiens

<400> SEQUENCE: 94

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Val Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Ile Pro Arg Thr Phe Gly Gln Gly Thr Lys Val Glu Ile
            100                 105                 110
Lys
```

<210> SEQ ID NO 95
<211> LENGTH: 119
<212> TYPE: PRT
<213> ORGANISM: Homo sapiens

<400> SEQUENCE: 95

```
Glu Val Gln Leu Val Gln Ser Gly Ala Glu Val Lys Lys Pro Gly Glu
1               5                   10                  15
Ser Leu Arg Ile Ser Cys Lys Gly Ser Gly Tyr Ser Phe Arg Pro Tyr
            20                  25                  30
Trp Ile Gly Trp Val Arg Gln Met Pro Gly Lys Gly Leu Glu Trp Met
```

```
                35                  40                  45
Gly Met Ile Asp Pro Ser Asp Ser Tyr Thr Asp Tyr Gly Pro Ser Phe
            50                  55                  60

Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
                100                 105                 110

Thr Met Val Thr Val Ser Ser
            115

<210> SEQ ID NO 96
<211> LENGTH: 112
<212> TYPE: PRT
<213> ORGANISM: Homo sapiens

<400> SEQUENCE: 96

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Arg Leu Leu His Ser
            20                  25                  30

Thr Gly Tyr Asn Tyr Leu Asn Trp Tyr Leu Gln Lys Pro Gly Gln Ser
        35                  40                  45

Pro Gln Leu Leu Ile Tyr Leu Gly Lys Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
                100                 105                 110

<210> SEQ ID NO 97
<211> LENGTH: 119
<212> TYPE: PRT
<213> ORGANISM: Homo sapiens

<400> SEQUENCE: 97

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Lys Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
                100                 105                 110

Thr Met Val Thr Val Ser Ser
            115
```

```
<210> SEQ ID NO 98
<211> LENGTH: 112
<212> TYPE: PRT
<213> ORGANISM: Homo sapiens

<400> SEQUENCE: 98

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Arg Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 99
<211> LENGTH: 119
<212> TYPE: PRT
<213> ORGANISM: Homo sapiens

<400> SEQUENCE: 99

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115

<210> SEQ ID NO 100
<211> LENGTH: 112
<212> TYPE: PRT
<213> ORGANISM: Homo sapiens

<400> SEQUENCE: 100

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Arg Asn Arg Ala Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 101
<211> LENGTH: 119
<212> TYPE: PRT
<213> ORGANISM: Homo sapiens

<400> SEQUENCE: 101

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

His Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Met Ser Gly Ala Phe Asp Ile Trp Gly Gln Gly
            100                 105                 110

Thr Met Val Thr Val Ser Ser
        115

<210> SEQ ID NO 102
<211> LENGTH: 112
<212> TYPE: PRT
<213> ORGANISM: Homo sapiens

<400> SEQUENCE: 102

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Lys Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 103
<211> LENGTH: 119
<212> TYPE: PRT
<213> ORGANISM: Homo sapiens

<400> SEQUENCE: 103

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Met Ile Asp Pro Thr Asp Ser Tyr Thr Asp Tyr Gly Pro Ser Phe
    50                  55                  60

His Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Arg Ile Met Ser Gly Ala Phe Asp Ile Trp Gly Gln Gly
            100                 105                 110

Thr Met Val Thr Val Ser Ser
            115

<210> SEQ ID NO 104
<211> LENGTH: 112
<212> TYPE: PRT
<213> ORGANISM: Homo sapiens

<400> SEQUENCE: 104

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Ser Arg Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 105
<211> LENGTH: 119
<212> TYPE: PRT
<213> ORGANISM: Homo sapiens

<400> SEQUENCE: 105

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115

<210> SEQ ID NO 106
<211> LENGTH: 112
<212> TYPE: PRT
<213> ORGANISM: Homo sapiens

<400> SEQUENCE: 106

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Arg Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 107
<211> LENGTH: 119
<212> TYPE: PRT
<213> ORGANISM: Homo sapiens

<400> SEQUENCE: 107

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115

<210> SEQ ID NO 108
<211> LENGTH: 112
<212> TYPE: PRT
<213> ORGANISM: Homo sapiens

<400> SEQUENCE: 108

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser

```
                    20                  25                  30

Thr Trp Tyr Asn Tyr Leu Asn Trp Tyr Leu Gln Lys Pro Gly Gln Ser
                35                  40                  45

Pro Gln Leu Leu Ile Tyr Leu Gly Lys Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
                100                 105                 110

<210> SEQ ID NO 109
<211> LENGTH: 119
<212> TYPE: PRT
<213> ORGANISM: Homo sapiens

<400> SEQUENCE: 109

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
                20                  25                  30

Trp Ile Gly Trp Val Arg Gln Met Pro Gly Lys Gly Leu Glu Trp Met
            35                  40                  45

Gly Met Ile Asp Pro Ser Asp Ser Tyr Thr Asp Tyr Gly Pro Ser Phe
        50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
                100                 105                 110

Thr Met Val Thr Val Ser Ser
            115

<210> SEQ ID NO 110
<211> LENGTH: 112
<212> TYPE: PRT
<213> ORGANISM: Homo sapiens

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Thr Trp Tyr Asn Tyr Leu Asn Trp Tyr Leu Gln Lys Pro Gly Gln Ser
                35                  40                  45

Pro Gln Leu Leu Ile Tyr Leu Gly Lys Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
                100                 105                 110
```

```
<210> SEQ ID NO 111
<211> LENGTH: 119
<212> TYPE: PRT
<213> ORGANISM: Homo sapiens

<400> SEQUENCE: 111

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Met Ile Asp Pro Thr Asp Ser Tyr Thr Asp Tyr Gly Pro Ser Phe
    50                  55                  60

His Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Arg Ile Met Ser Gly Ala Phe Asp Ile Trp Gly Gln Gly
            100                 105                 110

Thr Met Val Thr Val Ser Ser
        115

<210> SEQ ID NO 112
<211> LENGTH: 112
<212> TYPE: PRT
<213> ORGANISM: Homo sapiens

<400> SEQUENCE: 112

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Lys Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 113
<211> LENGTH: 119
<212> TYPE: PRT
<213> ORGANISM: Homo sapiens

<400> SEQUENCE: 113

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60
```

```
Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115
```

<210> SEQ ID NO 114
<211> LENGTH: 112
<212> TYPE: PRT
<213> ORGANISM: Homo sapiens

<400> SEQUENCE: 114

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Ser Arg Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110
```

<210> SEQ ID NO 115
<211> LENGTH: 119
<212> TYPE: PRT
<213> ORGANISM: Homo sapiens

<400> SEQUENCE: 115

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115
```

<210> SEQ ID NO 116
<211> LENGTH: 112
<212> TYPE: PRT
<213> ORGANISM: Homo sapiens

<400> SEQUENCE: 116

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Ser Arg Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 117
<211> LENGTH: 119
<212> TYPE: PRT
<213> ORGANISM: Homo sapiens

<400> SEQUENCE: 117

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115

<210> SEQ ID NO 118
<211> LENGTH: 112
<212> TYPE: PRT
<213> ORGANISM: Homo sapiens

<400> SEQUENCE: 118

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu His Ile Pro Tyr Thr Phe Gly Gln Gly Thr Lys Leu Glu Ile Lys
            100                 105                 110

<210> SEQ ID NO 119
<211> LENGTH: 119
<212> TYPE: PRT
<213> ORGANISM: Homo sapiens

<400> SEQUENCE: 119

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Arg Phe Thr Pro Tyr
            20                  25                  30

Trp Ile Gly Trp Val Arg Gln Met Pro Gly Lys Gly Leu Glu Trp Met
        35                  40                  45

Gly Met Ile Asp Pro Thr Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ser Gly Ala Phe Asp Ile Trp Gly Gln Gly
            100                 105                 110

Thr Met Val Thr Val Ser Ser
        115

<210> SEQ ID NO 120
<211> LENGTH: 112
<212> TYPE: PRT
<213> ORGANISM: Homo sapiens

<400> SEQUENCE: 120

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu His Ile Pro Tyr Thr Phe Gly Gln Gly Thr Lys Leu Glu Ile Lys
            100                 105                 110

<210> SEQ ID NO 121
<211> LENGTH: 122
<212> TYPE: PRT
<213> ORGANISM: Homo sapiens

<400> SEQUENCE: 121

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Arg Phe Asp Asp Tyr

```
            20                  25                  30
Ala Met His Trp Val Arg Gln Ala Pro Gly Lys Gly Leu Glu Trp Val
            35                  40                  45

Ser Gly Ile Ser Trp Arg Gly Ala Gln Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 122
<211> LENGTH: 107
<212> TYPE: PRT
<213> ORGANISM: Homo sapiens

<400> SEQUENCE: 122

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Lys Ile Ser Ser Trp
            20                  25                  30

Leu Ala Trp Tyr Gln Gln Lys Pro Gly Lys Ala Pro Lys Phe Leu Ile
            35                  40                  45

Tyr Lys Ala Ser Arg Leu Asp Arg Gly Val Pro Ser Arg Phe Ser Gly
        50                  55                  60

Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Arg Ser Tyr Ile Arg
                85                  90                  95

Thr Phe Gly Gln Gly Thr Lys Val Glu Ile Lys
            100                 105

<210> SEQ ID NO 123
<211> LENGTH: 122
<212> TYPE: PRT
<213> ORGANISM: Homo sapiens

<400> SEQUENCE: 123

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
            35                  40                  45

Ser Gly Ile Ser Trp Arg Gly Asp Ile Ile Gly Tyr Val Lys Ser Val
        50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ile Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
```

<210> SEQ ID NO 124
<211> LENGTH: 107
<212> TYPE: PRT
<213> ORGANISM: Homo sapiens

<400> SEQUENCE: 124

Asp Ile Gln Met Thr Gln Ser Pro Ser Thr Leu Ser Ala Ser Ala Gly
1               5                   10                  15

Asp Arg Val Thr Ile Thr Cys Arg Ala Ser Lys Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Glu Arg Leu Glu Arg Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 125
<211> LENGTH: 122
<212> TYPE: PRT
<213> ORGANISM: Homo sapiens

<400> SEQUENCE: 125

Glu Val Gln Leu Val Glu Ser Gly Gly Leu Val Gln Pro Gly Arg
1               5                   10                  15

Ser Leu Lys Leu Ser Cys Ala Ala Ser Lys Phe Arg Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Ile Gly Tyr Val Asp Ser Val
50                  55                  60

Lys Gly Arg Phe Thr Ile Ser Arg Asp Asn Glu Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 126
<211> LENGTH: 107
<212> TYPE: PRT
<213> ORGANISM: Homo sapiens

<400> SEQUENCE: 126

Asp Ile Gln Met Thr Gln Ser Pro Ser Thr Leu Ser Ala Ser Ala Gly
1               5                   10                  15

Asp Arg Val Thr Ile Thr Cys Arg Ala Ser Lys Ser Ile Ser Ser Trp
            20                  25                  30

Leu Ala Trp Tyr Gln Gln Lys Pro Gly Lys Ala Pro Lys Phe Leu Ile
        35                  40                  45

-continued

Tyr Lys Ala Ser Arg Leu Glu Arg Gly Val Pro Ser Arg Phe Ser Gly
            50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                    85                  90                  95

Thr Phe Gly Gln Gly Thr Lys Val Glu Ile Lys
                100                 105

<210> SEQ ID NO 127
<211> LENGTH: 122
<212> TYPE: PRT
<213> ORGANISM: Homo sapiens

<400> SEQUENCE: 127

Glu Val Gln Leu Val Glu Ser Gly Gly Leu Val Gln Pro Gly Arg
1               5                   10                  15

Ser Leu Lys Leu Ser Cys Ala Ala Ser Lys Phe Arg Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Arg Gly Asp Ile Ile Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 128
<211> LENGTH: 107
<212> TYPE: PRT
<213> ORGANISM: Homo sapiens

<400> SEQUENCE: 128

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Phe Leu Ile
            35                  40                  45

Tyr Lys Ala Ser Arg Leu Glu Arg Asp Val Pro Ser Arg Phe Ser Gly
        50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Arg Ser Tyr Ile Arg
                    85                  90                  95

Thr Phe Gly Gln Gly Thr Lys Val Glu Ile Lys
                100                 105

<210> SEQ ID NO 129
<211> LENGTH: 122
<212> TYPE: PRT
<213> ORGANISM: Homo sapiens

<400> SEQUENCE: 129

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Ile Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 130
<211> LENGTH: 107
<212> TYPE: PRT
<213> ORGANISM: Homo sapiens

<400> SEQUENCE: 130

Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Ile Lys Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Glu Arg Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 131
<211> LENGTH: 122
<212> TYPE: PRT
<213> ORGANISM: Homo sapiens

<400> SEQUENCE: 131

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Lys Gly Tyr Val Asp Ser Val
    50                  55                  60

Lys Gly Arg Phe Thr Ile Ser Arg Asp Asn Ala Lys Asn Ser Leu Tyr
65                  70                  75                  80

```
Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 132
<211> LENGTH: 107
<212> TYPE: PRT
<213> ORGANISM: Homo sapiens

<400> SEQUENCE: 132

```
Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105
```

<210> SEQ ID NO 133
<211> LENGTH: 122
<212> TYPE: PRT
<213> ORGANISM: Homo sapiens

<400> SEQUENCE: 133

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Thr Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 134
<211> LENGTH: 107
<212> TYPE: PRT
<213> ORGANISM: Homo sapiens

<400> SEQUENCE: 134

```
Asp Ile Gln Met Thr Gln Ser Pro Ser Thr Leu Ser Ala Ser Ala Gly
```

```
            1               5                  10                 15
Asp Arg Val Thr Ile Thr Cys Arg Ala Ser Gln Ser Ile Ser Ser Trp
                20                  25                 30

Leu Ala Trp Tyr Gln Gln Lys Pro Gly Lys Ala Pro Lys Phe Leu Ile
        35                  40                 45

Tyr Lys Ala Ser Arg Leu Asp Arg Gly Val Pro Ser Arg Phe Ser Gly
    50                  55                 60

Ser Gly Ser Gly Thr Glu Phe Ser Leu Thr Ile Ser Ser Leu Gln Pro
65                  70                 75                 80

Asp Asp Phe Ala Thr Tyr Tyr Cys Leu Glu Tyr Ser Ser Tyr Ile Arg
                85                 90                  95

Thr Phe Gly Gln Gly Thr Lys Val Glu Ile Lys
                100                105

<210> SEQ ID NO 135
<211> LENGTH: 122
<212> TYPE: PRT
<213> ORGANISM: Homo sapiens

<400> SEQUENCE: 135

Glu Val Gln Leu Val Glu Ser Gly Gly Gly Leu Val Gln Pro Gly Arg
1               5                  10                 15

Ser Leu Lys Leu Ser Cys Ala Ala Ser Gly Phe Thr Phe His Asp Tyr
                20                  25                 30

Ala Met His Trp Val Arg Gln Val Pro Gly Lys Gly Leu Glu Trp Val
        35                  40                 45

Ser Gly Ile Ser Trp Arg Gly Asp Ile Ile Gly Tyr Val Asp Ser Val
    50                  55                 60

Lys Gly Arg Phe Thr Ile Ser Arg Asp Asn Lys Asn Ser Leu Tyr
65                  70                 75                 80

Leu Gln Leu Asn Ser Leu Arg Ala Glu Asp Thr Ala Leu Tyr Tyr Cys
                85                 90                  95

Val Lys Ser Tyr Gly Ser Gly Ser Phe Tyr Asn Ala Phe Asp Ser Trp
                100                105                110

Gly Gln Gly Thr Leu Val Thr Val Ser Ser
            115                120

<210> SEQ ID NO 136
<211> LENGTH: 107
<212> TYPE: PRT
<213> ORGANISM: Homo sapiens

<400> SEQUENCE: 136

Asp Ile Gln Met Thr Gln Ser Pro Ser Thr Leu Ser Ala Ser Ala Gly
1               5                  10                 15

Asp Arg Val Thr Ile Thr Cys Arg Ala Ser Gln Ser Ile Ser Ser Trp
                20                  25                 30

Leu Ala Trp Tyr Gln Gln Lys Pro Gly Lys Ala Pro Lys Phe Leu Ile
        35                  40                 45

Tyr Lys Ala Ser Arg Leu Asp Arg Gly Val Pro Ser Arg Phe Ser Gly
    50                  55                 60

Ser Gly Ser Gly Thr Glu Phe Ser Leu Thr Ile Ser Ser Leu Gln Pro
65                  70                 75                 80

Asp Asp Phe Ala Thr Tyr Tyr Cys Leu Glu Tyr Ser Ser Tyr Ile Arg
                85                 90                  95

Thr Phe Gly Gln Gly Thr Lys Val Glu Ile Lys
```

-continued

```
                100             105

<210> SEQ ID NO 137
<211> LENGTH: 122
<212> TYPE: PRT
<213> ORGANISM: Homo sapiens

<400> SEQUENCE: 137

Glu Val Gln Leu Val Glu Ser Gly Gly Leu Val Gln Pro Gly Arg
1               5                   10                  15

Ser Leu Lys Leu Ser Cys Ala Ala Ser Lys Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Arg Gly Asp Ile Ile Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
            115                 120

<210> SEQ ID NO 138
<211> LENGTH: 107
<212> TYPE: PRT
<213> ORGANISM: Homo sapiens

<400> SEQUENCE: 138

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Phe Leu Ile
            35                  40                  45

Tyr Lys Ala Ser Arg Leu Glu Arg Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
                100                 105

<210> SEQ ID NO 139
<211> LENGTH: 122
<212> TYPE: PRT
<213> ORGANISM: Homo sapiens

<400> SEQUENCE: 139

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45
```

Ser Gly Ile Ser Trp Arg Gly Asp Ile Lys Gly Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 140
<211> LENGTH: 107
<212> TYPE: PRT
<213> ORGANISM: Homo sapiens

<400> SEQUENCE: 140

Asp Ile Gln Met Thr Gln Ser Pro Ser Thr Leu Ser Ala Ser Ala Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Phe Leu Ile
         35                  40                  45

Tyr Lys Ala Ser Arg Leu Glu Arg Gly Val Pro Ser Arg Phe Ser Gly
     50                  55                  60

Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
            100                 105

<210> SEQ ID NO 141
<211> LENGTH: 122
<212> TYPE: PRT
<213> ORGANISM: Homo sapiens

<400> SEQUENCE: 141

Glu Val Gln Leu Val Glu Ser Gly Gly Gly Leu Val Gln Pro Gly Arg
  1               5                  10                  15

Ser Leu Lys Leu Ser Cys Ala Ala Ser Gly Phe Thr Phe Asp Asp Tyr
             20                  25                  30

Ala Met His Trp Val Arg Gln Val Pro Gly Lys Gly Leu Glu Trp Val
         35                  40                  45

Ser Gly Ile Ser Trp Arg Gly Asp Ile Gly Gly Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 142

-continued

```
<211> LENGTH: 107
<212> TYPE: PRT
<213> ORGANISM: Homo sapiens

<400> SEQUENCE: 142

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Glu Arg Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 143
<211> LENGTH: 122
<212> TYPE: PRT
<213> ORGANISM: Homo sapiens

<400> SEQUENCE: 143

Glu Val Gln Leu Val Glu Ser Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Ile Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 144
<211> LENGTH: 107
<212> TYPE: PRT
<213> ORGANISM: Homo sapiens

<400> SEQUENCE: 144

Asp Ile Gln Met Thr Gln Ser Pro Ser Thr Leu Ser Ala Ser Ala Gly
1               5                   10                  15

Asp Arg Val Thr Ile Ser Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Val Pro Ser Arg Phe Ser Gly
50                  55                  60
```

```
Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Asn Ser Tyr Ile Arg
                85                  90                  95

Thr Phe Gly Gln Gly Thr Lys Val Glu Ile Lys
            100                 105

<210> SEQ ID NO 145
<211> LENGTH: 122
<212> TYPE: PRT
<213> ORGANISM: Homo sapiens

<400> SEQUENCE: 145

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Lys Gly Asp Ile Ile Gly Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 146
<211> LENGTH: 107
<212> TYPE: PRT
<213> ORGANISM: Homo sapiens

<400> SEQUENCE: 146

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Glu Trp
                20                  25                  30

Leu Ala Trp Tyr Gln Gln Lys Pro Gly Lys Ala Pro Lys Phe Leu Ile
            35                  40                  45

Tyr Lys Ala Ser Arg Leu Asp Arg Gly Val Pro Ser Arg Phe Ser Gly
        50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 147
<211> LENGTH: 122
<212> TYPE: PRT
<213> ORGANISM: Homo sapiens

<400> SEQUENCE: 147

Glu Val Gln Leu Val Glu Ser Gly Gly Gly Leu Val Gln Pro Gly Arg
```

```
            1               5                  10                 15
Ser Leu Lys Leu Ser Cys Ala Ala Ser Gly Phe Thr Phe Asp Asp Tyr
            20                 25                 30

Ala Met His Trp Val Arg Gln Val Pro Gly Lys Gly Leu Glu Trp Val
            35                 40                 45

Ser Gly Ile Ser Trp Arg Gly Asp Ile Ile Gly Tyr Val Lys Ser Val
            50                 55                 60

Lys Gly Arg Phe Thr Ile Ser Arg Asp Asn Ala Lys Asn Ser Leu Tyr
65                 70                 75                 80

Leu Gln Leu Asn Ser Leu Arg Ile Glu Asp Thr Ala Leu Tyr Tyr Cys
            85                 90                 95

Val Lys Ser Tyr Gly Ser Gly Ser Phe Tyr Asn Ala Phe Asp Ser Trp
            100                105                110

Gly Gln Gly Thr Leu Val Thr Val Ser Ser
            115                120
```

<210> SEQ ID NO 148
<211> LENGTH: 107
<212> TYPE: PRT
<213> ORGANISM: Homo sapiens

<400> SEQUENCE: 148

```
Asp Ile Gln Met Thr Gln Ser Pro Ser Thr Leu Ser Ala Ser Ala Gly
1               5                  10                 15

Asp Arg Val Thr Ile Thr Cys Arg Ala Ser Lys Ser Ile Ser Ser Trp
            20                 25                 30

Leu Ala Trp Tyr Gln Gln Lys Pro Gly Lys Ala Pro Lys Phe Leu Ile
            35                 40                 45

Tyr Lys Ala Ser Arg Leu Glu Arg Gly Val Pro Ser Arg Phe Ser Gly
            50                 55                 60

Ser Gly Ser Gly Thr Glu Phe Ser Leu Thr Ile Ser Ser Leu Gln Pro
65                 70                 75                 80

Asp Asp Phe Ala Thr Tyr Tyr Cys Leu Glu Tyr Ser Ser Tyr Ile Arg
            85                 90                 95

Thr Phe Gly Gln Gly Thr Lys Val Glu Ile Lys
            100                105
```

<210> SEQ ID NO 149
<211> LENGTH: 122
<212> TYPE: PRT
<213> ORGANISM: Homo sapiens

<400> SEQUENCE: 149

```
Glu Val Gln Leu Val Glu Ser Gly Gly Gly Leu Val Gln Pro Gly Arg
1               5                  10                 15

Ser Leu Lys Leu Ser Cys Ala Ala Ser Gly Phe Thr Phe Asp Asp Tyr
            20                 25                 30

Ala Met His Trp Val Arg Gln Val Pro Gly Lys Gly Leu Glu Trp Val
            35                 40                 45

Ser Gly Ile Ser Trp Arg Gly Asp Ile Ile Gly Tyr Val Asp Ser Val
            50                 55                 60

Lys Gly Arg Phe Thr Ile Ser Arg Asp Asn Ala Lys Asn Ser Leu Tyr
65                 70                 75                 80

Leu Gln Leu Asn Ser Leu Arg Ala Glu Asp Thr Ala Leu Tyr Tyr Cys
            85                 90                 95

Val Lys Ser Tyr Gly Ser Gly Ser Phe Tyr Asn Ala Phe Asp Ser Trp
```

```
            100                 105                 110
Gly Gln Gly Thr Leu Val Thr Val Ser Ser
        115                 120

<210> SEQ ID NO 150
<211> LENGTH: 107
<212> TYPE: PRT
<213> ORGANISM: Homo sapiens

<400> SEQUENCE: 150

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Glu Arg Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 151
<211> LENGTH: 120
<212> TYPE: PRT
<213> ORGANISM: Homo sapiens

<400> SEQUENCE: 151

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 152
<211> LENGTH: 109
<212> TYPE: PRT
<213> ORGANISM: Homo sapiens

<400> SEQUENCE: 152

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
            35                  40                  45

Ile Tyr Gly Ala Ser Ser Arg Ala Arg Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Arg
                 85                  90                  95

Leu Phe Thr Phe Gly Gln Gly Thr Lys Leu Glu Ile Lys
            100                 105

<210> SEQ ID NO 153
<211> LENGTH: 122
<212> TYPE: PRT
<213> ORGANISM: Homo sapiens

<400> SEQUENCE: 153

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe Asp Asp Tyr
             20                  25                  30

Ala Met His Trp Val Arg Gln Val Pro Gly Lys Gly Leu Glu Trp Val
         35                  40                  45

Ser Gly Ile Ser Trp Arg Gly Asp Ile Ile Gly Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 154
<211> LENGTH: 107
<212> TYPE: PRT
<213> ORGANISM: Homo sapiens

<400> SEQUENCE: 154

Asp Ile Gln Met Thr Gln Ser Pro Ser Thr Leu Ser Ala Ser Ala Gly
 1               5                  10                  15

Asp Arg Val Thr Ile Thr Cys Arg Ala Ser Gln Ser Ile Ser Glu Trp
             20                  25                  30

Leu Ala Trp Tyr Gln Gln Lys Pro Gly Lys Ala Pro Lys Phe Leu Ile
         35                  40                  45

Tyr Lys Ala Ser Arg Leu Asp Arg Gly Val Pro Ser Arg Phe Ser Gly
     50                  55                  60

Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
            100                 105

<210> SEQ ID NO 155

```
<211> LENGTH: 120
<212> TYPE: PRT
<213> ORGANISM: Homo sapiens

<400> SEQUENCE: 155

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
            115                 120

<210> SEQ ID NO 156
<211> LENGTH: 109
<212> TYPE: PRT
<213> ORGANISM: Homo sapiens

<400> SEQUENCE: 156

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Arg
                85                  90                  95

Leu Phe Thr Phe Gly Gln Gly Thr Lys Leu Glu Ile Lys
            100                 105

<210> SEQ ID NO 157
<211> LENGTH: 120
<212> TYPE: PRT
<213> ORGANISM: Homo sapiens

<400> SEQUENCE: 157

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
50                  55                  60
```

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr His Ser Glu Glu Phe Asp Val Trp Gly Gln
            100                 105                 110

Gly Thr Leu Val Thr Val Ser Ser
            115                 120

<210> SEQ ID NO 158
<211> LENGTH: 109
<212> TYPE: PRT
<213> ORGANISM: Homo sapiens

<400> SEQUENCE: 158

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Arg Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Arg
             85                  90                  95

Leu Phe Thr Phe Gly Gln Gly Thr Lys Leu Glu Ile Lys
            100                 105

<210> SEQ ID NO 159
<211> LENGTH: 119
<212> TYPE: PRT
<213> ORGANISM: Homo sapiens

<400> SEQUENCE: 159

Glu Val Gln Leu Val Gln Ser Gly Ala Glu Val Lys Lys Pro Gly Glu
  1               5                  10                  15

Ser Leu Arg Ile Ser Cys Lys Gly Ser Gly Tyr Ser Phe Arg Pro Tyr
             20                  25                  30

Trp Ile Gly Trp Val Arg Gln Met Pro Gly Lys Gly Leu Glu Trp Met
         35                  40                  45

Gly Met Ile Asp Pro Ser Asp Ser Tyr Thr Asp Tyr Gly Pro Ser Phe
 50                  55                  60

Arg Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Val Arg Ile Arg Ala Gly Ala Phe Asp Ile Trp Gly Gln Gly
            100                 105                 110

Thr Met Val Thr Val Ser Ser
            115

<210> SEQ ID NO 160
<211> LENGTH: 112
<212> TYPE: PRT
<213> ORGANISM: Homo sapiens
```

-continued

<400> SEQUENCE: 160

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Lys Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 161
<211> LENGTH: 123
<212> TYPE: PRT
<213> ORGANISM: Homo sapiens

<400> SEQUENCE: 161

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

His Met Asn Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Ile Ala Val Ala Gly Pro Leu Arg Val Tyr
            100                 105                 110

Trp Gly Gln Gly Thr Leu Val Thr Val Ser Ser
        115                 120

<210> SEQ ID NO 162
<211> LENGTH: 113
<212> TYPE: PRT
<213> ORGANISM: Homo sapiens

<400> SEQUENCE: 162

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln

```
                     85                  90                  95

Tyr Tyr Ser Ile Pro Arg Thr Phe Gly Gln Gly Thr Lys Val Glu Ile
            100                 105                 110

Lys

<210> SEQ ID NO 163
<211> LENGTH: 119
<212> TYPE: PRT
<213> ORGANISM: Homo sapiens

<400> SEQUENCE: 163

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly
            100                 105                 110

Thr Met Val Thr Val Ser Ser
        115

<210> SEQ ID NO 164
<211> LENGTH: 112
<212> TYPE: PRT
<213> ORGANISM: Homo sapiens

<400> SEQUENCE: 164

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Lys Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 165
<211> LENGTH: 123
<212> TYPE: PRT
<213> ORGANISM: Homo sapiens

<400> SEQUENCE: 165

Glu Val Gln Leu Val Glu Ser Gly Gly Gly Leu Val Lys Pro Gly Gly
1               5                   10                  15
```

Ser Leu Arg Leu Ser Cys Ala Ala Ser Gly Phe Thr Phe Ser Asp Ala
            20                  25                  30

Trp Met Asn Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asp Ser Leu Lys Thr Glu Asp Thr Ala Val Tyr
                85                  90                  95

Tyr Cys Thr Thr Asp Gly Ile Ala Val Ala Gly Pro Leu Arg Val Tyr
            100                 105                 110

Trp Gly Gln Gly Thr Leu Val Thr Val Ser Ser
        115                 120

<210> SEQ ID NO 166
<211> LENGTH: 113
<212> TYPE: PRT
<213> ORGANISM: Homo sapiens

<400> SEQUENCE: 166

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Arg Thr Phe Gly Gln Gly Thr Lys Val Glu Ile
            100                 105                 110

Lys

<210> SEQ ID NO 167
<211> LENGTH: 119
<212> TYPE: PRT
<213> ORGANISM: Homo sapiens

<400> SEQUENCE: 167

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ala Gly Ala Phe Asp Ile Trp Gly Gln Gly

```
                    100                 105                 110

Thr Met Val Thr Val Ser Ser
            115

<210> SEQ ID NO 168
<211> LENGTH: 112
<212> TYPE: PRT
<213> ORGANISM: Homo sapiens

<400> SEQUENCE: 168

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Trp Tyr Asn Tyr Leu Asn Trp Tyr Leu Gln Lys Pro Gly Gln Ser
        35                  40                  45

Pro Gln Leu Leu Ile Tyr Leu Gly Lys Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
            100                 105                 110

<210> SEQ ID NO 169
<211> LENGTH: 123
<212> TYPE: PRT
<213> ORGANISM: Homo sapiens

<400> SEQUENCE: 169

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Ile Ala Val Ala Gly Pro Leu Arg Val Tyr
            100                 105                 110

Trp Gly Gln Gly Thr Leu Val Thr Val Ser Ser
            115                 120

<210> SEQ ID NO 170
<211> LENGTH: 113
<212> TYPE: PRT
<213> ORGANISM: Homo sapiens

<400> SEQUENCE: 170

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30
```

Ser Asn Asn Gly Asn Tyr Leu Val Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Ile Pro Arg Thr Phe Gly Gln Gly Thr Lys Val Glu Ile
                100                 105                 110

Lys

<210> SEQ ID NO 171
<211> LENGTH: 122
<212> TYPE: PRT
<213> ORGANISM: Homo sapiens

<400> SEQUENCE: 171

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
                20                  25                  30

Ala Met His Trp Val Arg Gln Val Pro Gly Lys Gly Leu Glu Trp Val
            35                  40                  45

Ser Gly Ile Ser Trp Arg Gly Asp Ile Ile Gly Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
            115                 120

<210> SEQ ID NO 172
<211> LENGTH: 107
<212> TYPE: PRT
<213> ORGANISM: Homo sapiens

<400> SEQUENCE: 172

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Phe Leu Ile
            35                  40                  45

Tyr Lys Ala Ser Arg Leu Asp Arg Gly Val Pro Ser Arg Phe Ser Gly
 50                  55                  60

Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
                100                 105

<210> SEQ ID NO 173
<211> LENGTH: 123
<212> TYPE: PRT
<213> ORGANISM: Homo sapiens

<400> SEQUENCE: 173

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Ile Ala Val Ala Gly Pro Leu Arg Val Tyr
            100                 105                 110

Trp Gly Gln Gly Thr Leu Val Thr Val Ser Ser
        115                 120

<210> SEQ ID NO 174
<211> LENGTH: 113
<212> TYPE: PRT
<213> ORGANISM: Homo sapiens

<400> SEQUENCE: 174

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Gly Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Arg Thr Phe Gly Gln Gly Thr Lys Val Glu Ile
            100                 105                 110

Lys

<210> SEQ ID NO 175
<211> LENGTH: 119
<212> TYPE: PRT
<213> ORGANISM: Homo sapiens

<400> SEQUENCE: 175

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Arg Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Val Arg Ile Arg Ala Gly Ala Phe Asp Ile Trp Gly Gln Gly
                100                 105                 110

Thr Met Val Thr Val Ser Ser
            115

<210> SEQ ID NO 176
<211> LENGTH: 112
<212> TYPE: PRT
<213> ORGANISM: Homo sapiens

<400> SEQUENCE: 176

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Thr Trp Tyr Asn Tyr Leu Asn Trp Tyr Leu Gln Lys Pro Gly Gln Ser
             35                  40                  45

Pro Gln Leu Leu Ile Tyr Leu Gly Lys Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Val
                 85                  90                  95

Leu His Ile Pro Tyr Thr Phe Gly Gln Gly Thr Lys Leu Glu Ile Lys
                100                 105                 110

<210> SEQ ID NO 177
<211> LENGTH: 122
<212> TYPE: PRT
<213> ORGANISM: Homo sapiens

<400> SEQUENCE: 177

Glu Val Gln Leu Val Glu Ser Gly Gly Gly Leu Val Gln Pro Gly Arg
  1               5                  10                  15

Ser Leu Lys Leu Ser Cys Ala Ala Ser Gly Phe Thr Phe His Asp Tyr
                 20                  25                  30

Ala Met His Trp Val Arg Gln Val Pro Gly Lys Gly Leu Glu Trp Val
             35                  40                  45

Ser Gly Ile Ser Trp Arg Gly Asp Ile Ile Gly Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
            115                 120

<210> SEQ ID NO 178

```
<211> LENGTH: 107
<212> TYPE: PRT
<213> ORGANISM: Homo sapiens

<400> SEQUENCE: 178

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
            85                  90                  95

Thr Phe Gly Gln Gly Thr Lys Val Glu Ile Lys
            100                 105

<210> SEQ ID NO 179
<211> LENGTH: 120
<212> TYPE: PRT
<213> ORGANISM: Homo sapiens

<400> SEQUENCE: 179

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 180
<211> LENGTH: 109
<212> TYPE: PRT
<213> ORGANISM: Homo sapiens

<400> SEQUENCE: 180

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Arg
                85                  90                  95

Leu Phe Thr Phe Gly Gln Gly Thr Lys Leu Glu Ile Lys
            100                 105

<210> SEQ ID NO 181
<211> LENGTH: 122
<212> TYPE: PRT
<213> ORGANISM: Homo sapiens

<400> SEQUENCE: 181

Glu Val Gln Leu Val Glu Ser Gly Gly Leu Val Gln Pro Gly Arg
1               5                   10                  15

Ser Leu Lys Leu Ser Cys Ala Ala Ser Gly Phe Thr Phe His Asp Tyr
                20                  25                  30

Ala Met His Trp Val Arg Gln Val Pro Gly Lys Gly Leu Glu Trp Val
            35                  40                  45

Ser Gly Ile Ser Trp Arg Gly Asp Ile Ile Gly Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 182
<211> LENGTH: 107
<212> TYPE: PRT
<213> ORGANISM: Homo sapiens

<400> SEQUENCE: 182

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Phe Leu Ile
            35                  40                  45

Tyr Lys Ala Ser Arg Leu Asp Arg Gly Thr Pro Ser Arg Phe Ser Gly
        50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 183
<211> LENGTH: 120
<212> TYPE: PRT
<213> ORGANISM: Homo sapiens

<400> SEQUENCE: 183

Glu Val Gln Leu Val Gln Ser Gly Ala Glu Val Lys Lys Pro Gly Glu

```
            1               5                   10                  15
Ser Leu Arg Ile Ser Cys Lys Gly Ser Gly Tyr Ser Phe Thr Thr Ser
                20                  25                  30

Trp Ile Val Trp Val Arg Gln Met Pro Gly Lys Gly Leu Glu Trp Met
                35                  40                  45

Gly Met Ile Asp Pro Ser Asp Ser Phe Thr Ser Tyr Ser Pro Ser Phe
            50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
                100                 105                 110

Gly Thr Leu Val Thr Val Ser Ser
                115                 120
```

<210> SEQ ID NO 184
<211> LENGTH: 109
<212> TYPE: PRT
<213> ORGANISM: Homo sapiens

<400> SEQUENCE: 184

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Thr Arg Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Arg
                85                  90                  95

Leu Phe Thr Phe Gly Glu Gly Thr Lys Leu Glu Ile Lys
                100                 105
```

<210> SEQ ID NO 185
<211> LENGTH: 123
<212> TYPE: PRT
<213> ORGANISM: Homo sapiens

<400> SEQUENCE: 185

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
                20                  25                  30

Trp Met Asn Trp Val Arg Gln Ala Pro Gly Lys Gly Leu Glu Trp Val
                35                  40                  45

Gly Arg Ile Lys Arg Lys Thr Asp Gly Gly Thr Thr Asp Tyr Ala Ala
            50                  55                  60

Pro Val Lys Gly Arg Phe Thr Ile Ser Arg Asp Asp Ser Lys Asn Thr
65                  70                  75                  80

Leu Tyr Leu Gln Met Asp Ser Leu Lys Thr Glu Asp Thr Ala Val Tyr
                85                  90                  95

Tyr Cys Thr Thr Asp Gly Ile Ala Val Ala Gly Pro Leu Arg Val Tyr
```

```
            100                 105                 110
Trp Gly Gln Gly Thr Leu Val Thr Val Ser Ser
        115                 120

<210> SEQ ID NO 186
<211> LENGTH: 113
<212> TYPE: PRT
<213> ORGANISM: Homo sapiens

<400> SEQUENCE: 186

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Arg Thr Phe Gly Gln Gly Thr Lys Val Glu Ile
            100                 105                 110

Lys

<210> SEQ ID NO 187
<211> LENGTH: 119
<212> TYPE: PRT
<213> ORGANISM: Homo sapiens

<400> SEQUENCE: 187

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Arg Pro Tyr
            20                  25                  30

Trp Ile Gly Trp Val Arg Gln Met Pro Gly Lys Gly Leu Glu Trp Met
        35                  40                  45

Gly Met Ile Asp Pro Ser Asp Ser Tyr Thr Asp Tyr Gly Pro Ser Phe
    50                  55                  60

Glu Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Arg Ile Arg Ser Gly Ala Phe Asp Ile Trp Gly Gln Gly
            100                 105                 110

Thr Met Val Thr Val Ser Ser
        115

<210> SEQ ID NO 188
<211> LENGTH: 112
<212> TYPE: PRT
<213> ORGANISM: Homo sapiens

<400> SEQUENCE: 188

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Arg Leu Leu His Arg
            20                  25                  30

Thr Gly Tyr Asn Tyr Leu Asn Trp Tyr Leu Gln Lys Pro Gly Gln Ser
        35                  40                  45

Pro Gln Leu Leu Ile Tyr Leu Gly Ser Arg Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu His Ile Pro Tyr Thr Phe Gly Gln Gly Thr Lys Leu Glu Ile Lys
                100                 105                 110
```

<210> SEQ ID NO 189
<211> LENGTH: 5
<212> TYPE: PRT
<213> ORGANISM: Artificial Sequence
<220> FEATURE:
<223> OTHER INFORMATION: Synthetic

<400> SEQUENCE: 189

```
Asp Tyr Ala Met His
1               5
```

<210> SEQ ID NO 190
<211> LENGTH: 17
<212> TYPE: PRT
<213> ORGANISM: Artificial Sequence
<220> FEATURE:
<223> OTHER INFORMATION: Synthetic

<400> SEQUENCE: 190

```
Gly Ile Ser Trp Arg Gly Asp Ile Ile Gly Tyr Val Asp Ser Val Lys
1               5                   10                  15

Gly
```

<210> SEQ ID NO 191
<211> LENGTH: 13
<212> TYPE: PRT
<213> ORGANISM: Artificial Sequence
<220> FEATURE:
<223> OTHER INFORMATION: Synthetic

<400> SEQUENCE: 191

```
Ser Tyr Gly Ser Gly Ser Phe Tyr Asn Ala Phe Asp Ser
1               5                   10
```

<210> SEQ ID NO 192
<211> LENGTH: 11
<212> TYPE: PRT
<213> ORGANISM: Artificial Sequence
<220> FEATURE:
<223> OTHER INFORMATION: Synthetic

<400> SEQUENCE: 192

```
Arg Ala Ser Gln Ser Ile Ser Ser Trp Leu Ala
1               5                   10
```

<210> SEQ ID NO 193
<211> LENGTH: 7
<212> TYPE: PRT
<213> ORGANISM: Artificial Sequence
<220> FEATURE:
<223> OTHER INFORMATION: Synthetic

<400> SEQUENCE: 193

Lys Ala Ser Arg Leu Asp Arg
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic

<400> SEQUENCE: 194

Leu Glu Tyr Ser Ser Tyr Ile Arg Thr
1               5

<210> SEQ ID NO 195
<211> LENGTH: 5
<212> TYPE: PRT
<213> ORGANISM: Artificial Sequence
<220> FEATURE:
<223> OTHER INFORMATION: Synthetic

<400> SEQUENCE: 195

Thr Ser Trp Ile Val
1               5

<210> SEQ ID NO 196
<211> LENGTH: 17
<212> TYPE: PRT
<213> ORGANISM: Artificial Sequence
<220> FEATURE:
<223> OTHER INFORMATION: Synthetic

<400> SEQUENCE: 196

Met Ile Asp Pro Ser Asp Ser Phe Thr Ser Tyr Ser Pro Ser Phe Gln
1               5                   10                  15

Gly

<210> SEQ ID NO 197
<211> LENGTH: 11
<212> TYPE: PRT
<213> ORGANISM: Artificial Sequence
<220> FEATURE:
<223> OTHER INFORMATION: Synthetic

<400> SEQUENCE: 197

Leu His Tyr Tyr His Ser Glu Glu Phe Asp Val
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Synthetic

<400> SEQUENCE: 198

Arg Ala Ser Gln Ser Val Ser Ser Ser Tyr Leu Ala
1               5                   10

<210> SEQ ID NO 199
<211> LENGTH: 7
<212> TYPE: PRT
<213> ORGANISM: Artificial Sequence
<220> FEATURE:

```
<223> OTHER INFORMATION: Synthetic

<400> SEQUENCE: 199

Gly Ala Ser Ser Arg Ala Arg
1               5

<210> SEQ ID NO 200
<211> LENGTH: 10
<212> TYPE: PRT
<213> ORGANISM: Artificial Sequence
<220> FEATURE:
<223> OTHER INFORMATION: Synthetic

<400> SEQUENCE: 200

Gln Gln Phe Gly Ser Ser Arg Leu Phe Thr
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Synthetic

<400> SEQUENCE: 201

Arg Ala Ser Gln Ser Ile Ser Ser Trp Leu Ala
1               5                   10

<210> SEQ ID NO 202
<211> LENGTH: 7
<212> TYPE: PRT
<213> ORGANISM: Artificial Sequence
<220> FEATURE:
<223> OTHER INFORMATION: Synthetic

<400> SEQUENCE: 202

Gly Ala Ser Ser Arg Thr Arg
1               5
```